US010927069B2

(12) United States Patent
Imig et al.

(10) Patent No.: US 10,927,069 B2
(45) Date of Patent: Feb. 23, 2021

(54) DIABETES AND METABOLIC SYNDROME TREATMENT WITH A NOVEL DUAL MODULATOR OF SOLUBLE EPOXIDE HYDROLASE AND PEROXISOME PROLIFERATOR-ACTIVATED RECEPTORS

(71) Applicants: The Medical College of Wisconsin, Inc., Milwaukee, WI (US); Johann Wolfgang Goethe-Universitat Frankfurt, Frankfurt am Main (DE)

(72) Inventors: John David Imig, Pewaukee, WI (US); Md. Abdul Hye Khan, Milwaukee, WI (US); Eugen Proschak, Frankfurt am Main (DE); Rene Blocher, Frankfurt am Main (DE)

(73) Assignees: The Medical College of Wisconsin, Inc., Milwaukee, WI (US); Johann Wolfgang Goethe-Universitat Frankfurt, Frankfurt am Main (DE)

( * ) Notice: Subject to any disclaimer, the term of this patent is extended or adjusted under 35 U.S.C. 154(b) by 0 days.

(21) Appl. No.: 15/737,970

(22) PCT Filed: Jul. 1, 2016

(86) PCT No.: PCT/US2016/040708

§ 371 (c)(1),
(2) Date: Dec. 19, 2017

(87) PCT Pub. No.: WO2017/004525

PCT Pub. Date: Jan. 5, 2017

(65) Prior Publication Data

US 2018/0297936 A1 Oct. 18, 2018

Related U.S. Application Data

(60) Provisional application No. 62/188,010, filed on Jul. 2, 2015.

(51) Int. Cl.

| | |
|---|---|
| ***C07C 233/66*** | (2006.01) |
| ***C07C 233/73*** | (2006.01) |
| ***C07C 233/65*** | (2006.01) |
| ***A61P 3/10*** | (2006.01) |
| ***A61K 9/00*** | (2006.01) |
| ***A61M 25/01*** | (2006.01) |
| ***A61B 5/06*** | (2006.01) |
| ***A61M 25/00*** | (2006.01) |
| ***A61B 18/14*** | (2006.01) |
| *A61B 18/00* | (2006.01) |
| *A61B 5/00* | (2006.01) |
| *A61B 34/20* | (2016.01) |

(52) U.S. Cl.
CPC ............ *C07C 233/66* (2013.01); *A61B 5/062* (2013.01); *A61B 18/1492* (2013.01); *A61K 9/0053* (2013.01); *A61M 25/0012* (2013.01); *A61M 25/0127* (2013.01); *A61P 3/10* (2018.01); *C07C 233/65* (2013.01); *C07C 233/73* (2013.01); *A61B 5/6852* (2013.01); *A61B 2018/00029* (2013.01); *A61B 2018/00577* (2013.01); *A61B 2034/2051* (2016.02)

(58) Field of Classification Search
None
See application file for complete search history.

(56) References Cited

FOREIGN PATENT DOCUMENTS

| | | |
|---|---|---|
| CN | 102643248 A | 8/2012 |
| WO | 0244127 A1 | 6/2002 |
| WO | WO0244127 * | 6/2002 |

OTHER PUBLICATIONS

Ito et al., A medium-term rat liver bioassay for rapid in vivo detection of carcinogenic potential of chemicals. Cancer Science, 2003, 94, 3-8.*
Chinese First Office Action dated Jan. 2, 2020.

* cited by examiner

*Primary Examiner* — Kamal A Saeed
(74) *Attorney, Agent, or Firm* — Boyle Fredrickson S.C.

(57) ABSTRACT

N-benzylbenzamides that act as dual soluble soluble epoxide hydrolase (sEH)/peroxisome proliferator-activated receptor γ (PPARγ) modulators and are useful as medications in the treatment of Metabolic Syndrome (MetS) cluster diseases, including diabetes. Methods of making and using the same are further provided.

22 Claims, 30 Drawing Sheets

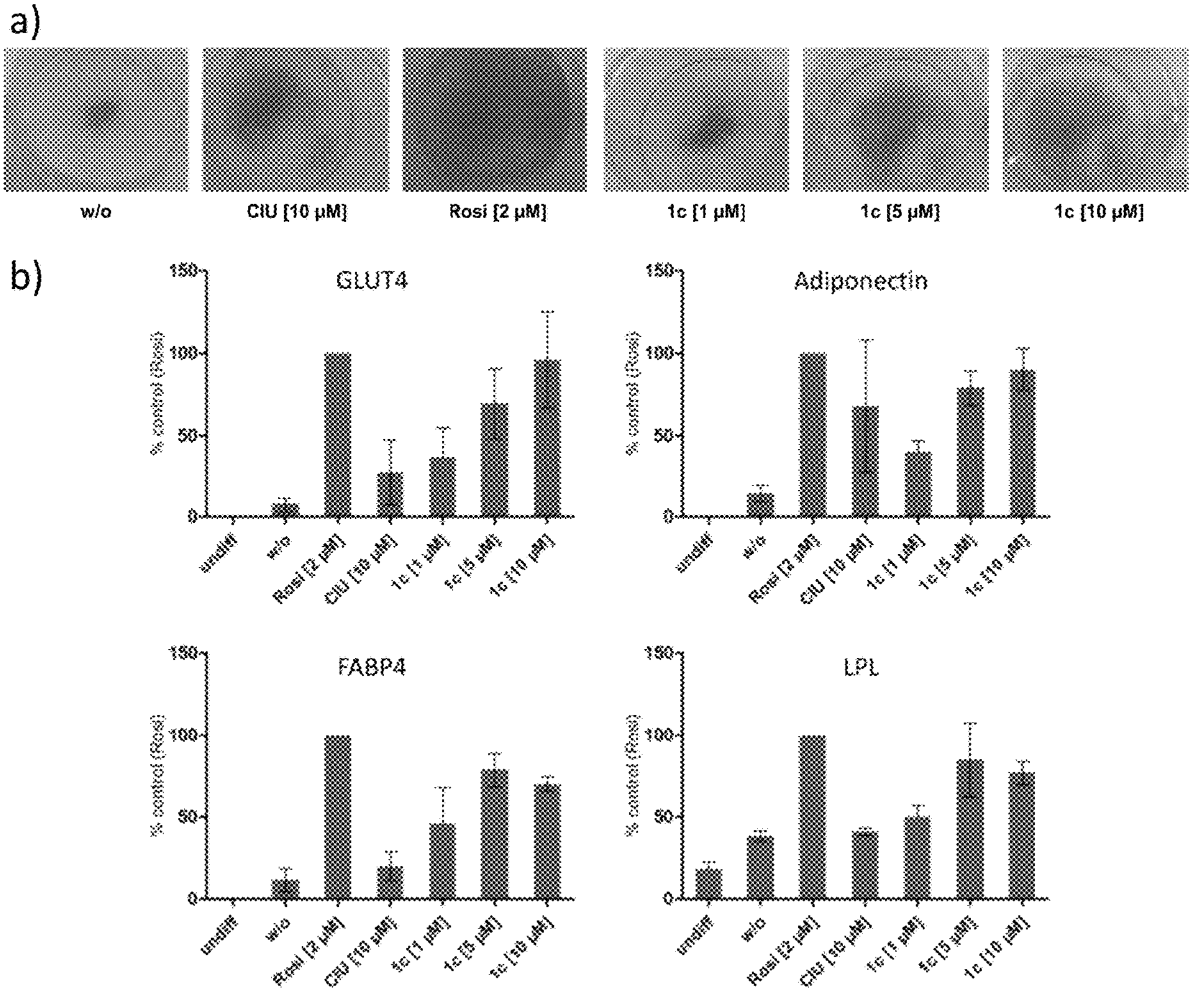
Figure 2 A-B

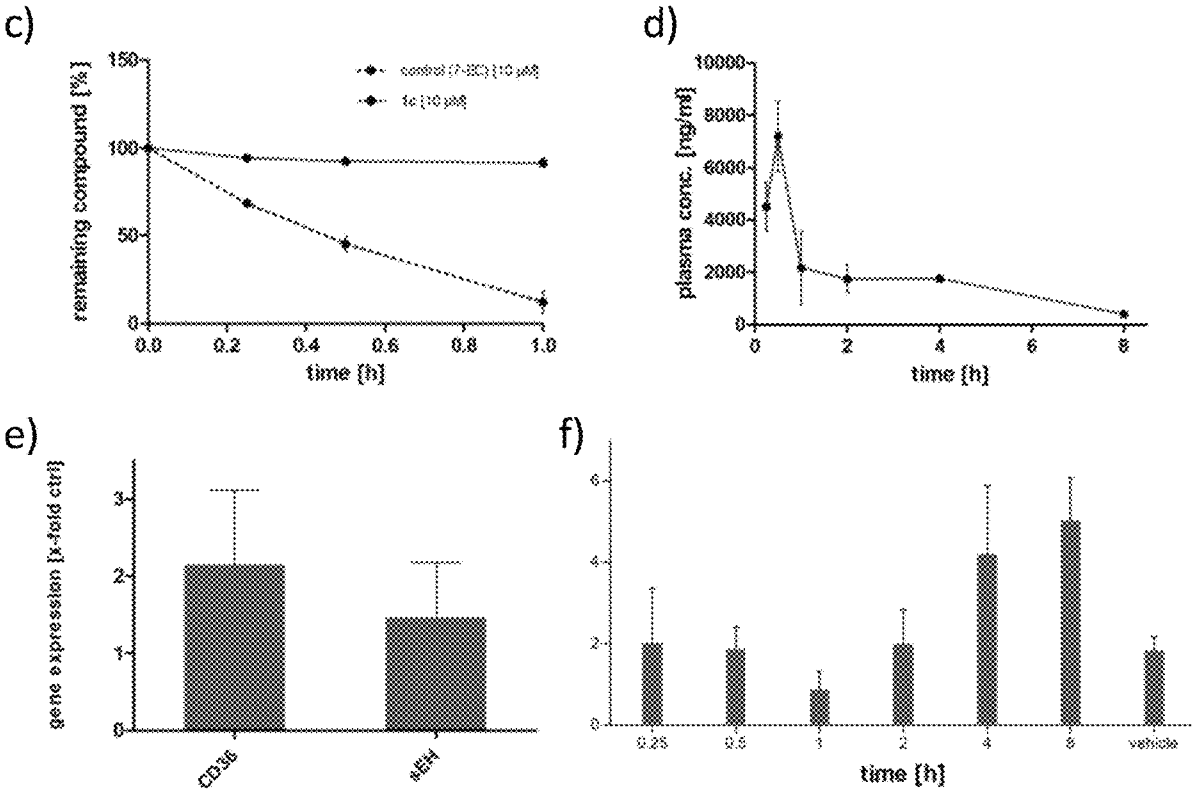
Figure 2 C-F

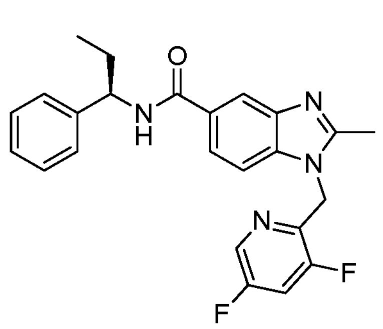
GSK1997132B
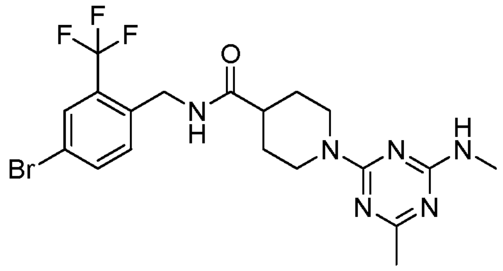
GSK2188931B
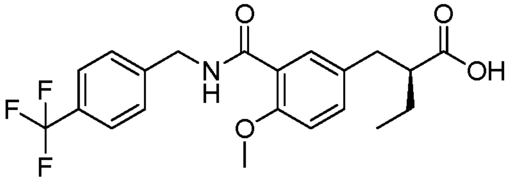
KCL
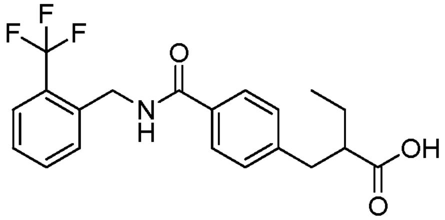
1c
Figure 6

- ***In vitro* data**
  - ✓ $IC_{50}$ (sEH) : 1.6 ± 0.2 µM
  - ✓ $EC_{50}$(PPAR γ) : 4.8 ± 2.1 µM | 127 %
  - ✓ No cytotoxicity up to 30 µM in HepG2
  - ✓ ~ 92 % remaining after 60 min in rat liver (Spargue-Dawley) microsomes
  - ✓ Activates adipocyte differentiation (human & mouse)
  - ✓ Water solubility 100 - 500 µM (PBS; pH 7.4; 0.01% Tween; 1 % DMSO):
- ***In vivo* data**
  - ✓ Per Oral application: Plasma Level 20 µM
    ~ 4 h above $EC_{50}$ conc. in Plasma
  - ✓ Positive effect on EET / DHET ratio in mouse plasma

- ***In vitro* data**
  - ✓ $IC_{50}$ (sEH) : 0.3 ± 0.05 µM
  - ✓ $EC_{50}$(PPAR γ) : 0.3 ± 0.09 µM | 160 %
  - ✓ No cytotoxicity up to 30 µM in HepG2
  - ✓ ~ 96 % remaining after 60 min in rat liver (Spargue-Dawley) microsomes
  - ✓ Water solubility : 500 - 750 µM (PBS; pH 7.4; 0.01% Tween; 1 % DMSO)
- ***In vivo* data**
  - ✓ 2 week water application: Plasma Level ~ 3 µM
    **steady state: 10 fold above *in vitro* $EC_{50}$**
  - ✓ Expression of PPARγ target gene
    - CD36: 8 ± 4.5 fold (mouse liver)

Figure 16

ZSF1 Protocol

DIABETES AND METABOLIC SYNDROME TREATMENT WITH A NOVEL DUAL MODULATOR OF SOLUBLE EPOXIDE HYDROLASE AND PEROXISOME PROLIFERATOR-ACTIVATED RECEPTORS

CROSS-REFERENCE TO RELATED APPLICATIONS

This application claims the benefit of U.S. Provisional Appn. No. 62/188,010, filed Jul. 2, 2015, which is incorporated by reference herein for all purposes.

STATEMENT REGARDING FEDERALLY SPONSORED RESEARCH OR DEVELOPMENT

This invention was made with government support under 1R01DK103616-0A1 awarded by the National Institutes of Health. The government has certain rights in the invention.

FIELD OF INVENTION

This invention relates generally to the treatment of Metabolic Syndrome (MetS) and related conditions. More particularly, the present invention is directed to N-benzylbenzamides that act as dual soluble soluble epoxide hydrolase (sEH)/peroxisome proliferator-activated receptor γ (PPARγ) modulators and are useful as medications in the treatment of MetS cluster diseases, including diabetes.

BACKGROUND OF THE INVENTION

The metabolic syndrome (MetS) is the name for a group of risk factors such as central obesity, atherogenic dyslipidemia, insulin resistance and endothelial dysfunction leading to arteriosclerotic cardiovascular diseases (ASCVD) such as coronary heart disease, stroke and peripheral vascular disease as well as type 2 diabetes (T2D)[1-4]. In addition, patients affected by T2D develop long-term microvascular complications: Two thirds of the individuals suffer from neuropathic pain[5] and one third develops diabetic nephropathy[6]. The MetS has a very complex pathophysiology which is only partially understood. See FIG. 1. Epidemiological evidence shows that the rising prevalence of the MetS in western societies is due to western lifestyle factors such as misbalanced, high caloric food intake, sedentary lifestyle and stress[3]. Up to now, the first-line treatment of the MetS covering all risk factors at once is a change in lifestyle meaning weight reduction, increased physical activity and an anti-atherogenic diet[3,7,8]. Nevertheless, already developed individual disorders such as endothelial dysfunction and T2D cannot be completely reversed by this approach and symptoms will worsen with advancing age. Therefore, patients accumulating various risk factors with time also accumulate quite a number of medications to treat each disorder separately[9].

Obesity forms the basis of several risk factors in MetS and is therefore an important target. Pharmacological weight control can be achieved altering either appetite or calorie absorption. An altered appetite can be achieved by interfering with the central nervous system (CNS) but many drugs were already withdrawn from the market due to severe side effects[10,11]. Orlistat the only approved drug directly altering calorie absorption, inhibits pancreatic and gastric lipases and acts outside the CNS[8].

Another facet of the MetS, atherogenic dyslipidemia, is based on an abnormal lipoprotein metabolism leading to plaque formation and atherosclerosis. Here, 3-hydroxy-3-methylglutaryl coenzyme A (HMG CoA) reductase inhibitors (statins)[12] and PPARα agonists (fibrates) are used today to lower plasma cholesterol and triglyceride levels[13]. Partly initiated by atherogenesis, long-term high blood pressure provokes macrovascular events such as cardiovascular disease (CVD) and stroke, the main causes of death in MetS patients[14]. Hypertension therapy usually involves a combination of drugs such as diuretics and beta-blockers. However, this might not be an option in the treatment of MetS patients since insulin resistance and dyslipidemia may worsen during therapy[15]. Here, other blood pressure lowering medications such as angiotensin converting enzyme antagonists and angiotensin-II-receptor blockers are preferentially used.

The probably most relevant disorder caused by the MetS is T2D. Here, peripheral insulin resistance is induced by metabolic dysfunction leading to hyperinsulinemia and elevated blood glucose. As disease progresses pancreatic β-islet cell function is gradually lost resulting in global insulin deficiency and hyperglycemia[16,17]. In the advanced state, poorly treated T2D patients develop a plethora of microvascular complications such as retinopathy, painful neuropathy and nephropathy and strict glycemic control and adjusted blood-pressure levels are the only way for prevention[18]. So far, the established therapies to treat or ameliorate T2D are less effective or successful compared to the treatment of other risk factor of the MetS[18]. The increase of available insulin is one way to compensate the peripheral insulin-resistance in muscle and liver cells. This can be accomplished either by application of sulfonylureas or biguanides which trigger pancreatic insulin release or by insulin therapy (external injection)[19,20].

To sum up, the treatment of the MetS risk factors and follow-up diseases requires a tremendous amount of drugs leading to the phenomenon of polypharmacy. Here, the pharmacokinetic and pharmacologic situation in patients reaches an unfavorable complexity and unpredictable drug-drug interactions can occur. In addition, medical compliance is at risk. While therapy costs rise, the probability for medication errors increases[3]. In this situation it is advisable to focus drug research on compounds capable of treating more than one aspect of the MetS. Therefore, multi-target ligands addressing more than one risk factor at once may find a reasonable application in this case[21].

PPARγ, a member of the PPAR nuclear receptor family, is activated endogenously by various lipophilic compounds such as long chain fatty acids and eicosanoids. After recruitment of co-activators, the receptor heterodimerizes with the retionid X receptor (RXR)[22] and influences ligand dependent as well as independent the transcription/transrepression of various target genes. PPARγ plays a key role in adipogenesis, regulation of lipid metabolism and glucose homeostasis as well as anti-inflammatory processes and is therefore used for the treatment of T2D[23]. Pharmacological activation of the receptor by thiazolidinediones (TZDs) such as rosiglitazone and pioglitazone displays beneficial effects on insulin action and blood-glucose levels[24]. In the "lipid steal hypothesis" these effects originate from free fatty acid (FFA) and triglyceride (TG) uptake into the white adipose tissue. This is maintained by the upregulation of several PPARγ target genes such as FABP4 (human adipocyte fatty acid binding protein 4, corresponds to murine ap4), LPL (lipoprotein lipase), fatty acid transport proteins (CD36, fatty acid translocase, FATP, glycerol transporter aquaporins) and PEPCK (phosphoenolpyruvat-carboxykinase)[25-30]. In addition, the insulin-sensitizing effect of PPARγ is correlated with the upregulation of bioactive adipokines such as adiponectin leading to decreased hepatic glucose output and improved glucose uptake[31-34] and anti-inflammatory properties of PPAR□ activation such as suppression of tumor necrosis factor α (TNFα) and resistin negatively influence insulin-resistance[35,36] Recent studies also showed that TZDs may have a preventive effect on pancreatic β-cell function, stabilizing insulin-secretion and supporting whole-blood insulin action[37-39]. It is also of interest that PPARγ activation has been discussed to upregulate HDL-C lipoprotein and might be valuable in the treatment of dyslipidemia[40,41].

However, the clinical use of TZDs is limited due to excessive weight gain, fluid retention and increased osteoporosis risk in treated patients[42,43] Meta-analyses of clinical trials have implicated rosiglitazone in increasing the risk of congestive heart failure, myocardial infarction, cardiovascular disease and all-cause mortality leading to tightly restricted access in the United States and a recommendation for market withdrawal in Europe. Troglitazone was withdrawn from the market due to hepatotoxicity and pioglitazone seems to trigger bladder cancer[44]. Another drawback is the poor effect of TZDs on the occurrence of macrovascular events, although the equilibration of blood glucose levels reduces microvascular complications[45]. In this context, it is important to mention that some of the adverse events seen with TZD such as cancer development and hepatotoxicity seem to be a compound characteristic instead of a class specific phenomenon[46-48].

The soluble epoxide hydrolase (sEH) is abundantly expressed in adipose tissue and whose expression and activity increases with obesity[49]. The sEH is an enzyme of the arachidonic acid cascade, promoting the hydrolysis of cytochrome P450 derived epoxyeicosatrienoic acids (EETs) to their less bioactive corresponding diols, the dihydroxyepoxyeicosatrienoic acids (DHETs)[50]. Through sEH inhibition EET levels increase. Endothelial cell derived EETs activate calcium-activated-potassium channels on smooth muscle cells, leading to hyperpolarization and vascular relaxation[51,52]. Numerous studies show EET-derived effects on various MetS associated disorders such as cardiovascular disease (CVD)[53], dyslipidemia[54], neuropathy[55-57] and nephropathy[58]. In animal models of hypertension EETs act as endothelial-derived relaxation factors and have multiple protective effects on the cardiovascular system. Recent studies have shown improved angiogenesis by endothelial progenitor cells derived from patients with acute myocardial infarction through sEH inhibition and subsequent activation of PPARγ by accumulating EETs[59,60]. The relevance of sEH inhibition in dyslipidemia therapy was already shown by Hammock et al. In this study, sEH inhibition in LDL receptor knock-out mice increased ABCA1 (ATP-binding cassette transporter A1) expression, a cholesterol efflux regulatory protein facilitating cholesterol export from cells and subsequent formation of nascent HDL, in adipose tissue. This was accompanied by an increase in circulating HDL, which enhances the reverse cholesterol transport pathway. In addition, sEH inhibition reduced LDL-C levels, and reduced the size of established atherosclerotic plaques in the animals[54]. Furthermore, sEH inhibition showed analgesic effects in several in vivo diabetic neuropathic pain models[56,61,62]. As described previously, the impaired functionality of pancreatic islet β-cells is one of the underlying mechanisms leading to T2D. It was shown that sEH inhibition can prevent hyperglycemia and augments islet glucose stimulated insulin secretion in diabetic mice. In addition, sEH-knock-out mice displayed attenuated islet cell apoptosis in STZ-induced diabetes[63]. Furthermore, several mouse models could show that sEH inhibition has renoprotective effects[58]. At the moment no sEH inhibitors are on the market. Accordingly, as there is an unmet medical need for safer PPARγ modulating drugs that carry additional cardio and kidney protective properties, the combination of PPARγ agonism with sEH antagonism in one compound would have substantial advantages in the treatment of MetS and T2D.

SUMMARY OF INVENTION

Here, the inventors present a multi-target approach to treat MetS cluster diseases, including diabetes, by administration of certain N-benzylbenzamides to affect the simultaneous modulation of soluble epoxide hydrolase (sEH) and peroxisome proliferator-activated receptor γ (PPARγ).

Accordingly, the invention encompasses, in a first aspect, certain compounds having the structure:

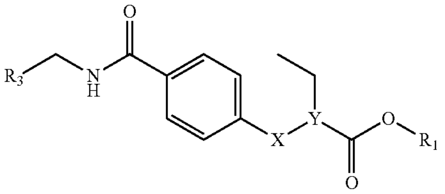

wherein: X—Y is CH═C or $CH_2$—CH; $R_1$ is $CH_2CH_3$, $CH_3$ or H; and $R_3$ is a fluoro-substituted aryl group; or a salt thereof. The fluoro-substituted aryl group at $R_3$ is preferably a phenyl group comprising a trifluoromethyl- or trifluoromethoxy-substitution, even more preferably substituted at the phenyl group's ortho position.

In certain compounds according to the invention, $R_3$ is:

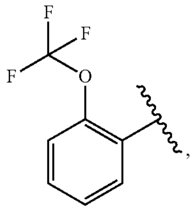,

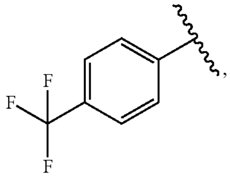,

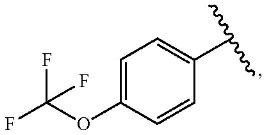,

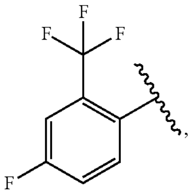, or

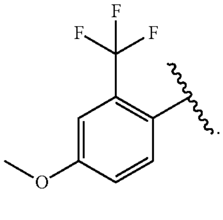 [SMILES: *c1ccc(OC)cc1C(F)(F)F].

A preferred compound of the invention calls for $R_3$ to be

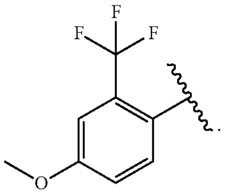

Compounds of the invention include those wherein: X—Y is $CH_2$—CH and $R_1$ is $CH_2CH_3$; X—Y is CH═C and $R_1$ is $CH_2CH_3$; X—Y is $CH_2$—CH and $R_1$ is H; and X—Y is CH═CH and $R_1$ is H.

A particularly preferred compound according to the invention calls for X—Y to be $CH_2CH$, $R_1$ to be H, and $R_3$ to be

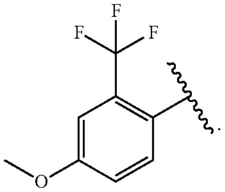

In particularly preferred embodiments, the inventive compound exhibits a half maximal inhibitory concentration ($IC_{50}$) for soluble epoxide hydrolase (sEH) and a half maximal effective concentration ($EC_{50}$) for peroxisome proliferator-activated receptor gamma (PPARγ) that are less than 1.0 micromolar when administered to a subject.

In another aspect, the invention provides a composition comprising: (a) an inventive N-benzylbenzadmide compound; and (b) a pharmaceutically acceptable carrier. In preferred embodiments, this composition is formulated as an oral dosage.

In yet another aspect, the invention provides a method of treating metabolic syndrome in a subject, comprising administering to a subject a therapeutically effective amount of an inventive N-benzylbenzamide compound, wherein soluble epoxide hydrolase (sEH) and peroxisome proliferator-activated receptor gamma (PPARγ) are simultaneously-modulated by the compound thereby treating metabolic syndrome in the subject.

In preferred embodiments, the therapeutically effective amount provides a half maximal inhibitory concentration ($IC_{50}$) for sEH and a half maximal effective concentration ($EC_{50}$) for PPARγ that are less than 1.0 micromolar in the subject.

In another embodiment, the invention encompasses the use of an inventive N-benylbenzamide compound for the manufacture of a medicament for treating MetS in a subject. As well, the invention further contemplates compounds according to the invention for use in treating MetS in a subject.

In yet another aspect, the invention provides a method of treating diabetes in a subject, comprising administering to a subject a therapeutically effective amount of an inventive N-benzylbenzamide compound, wherein soluble epoxide hydrolase (sEH) and peroxisome proliferator-activated receptor gamma (PPARγ) are simultaneously-modulated by the compound thereby treating diabetes in the subject.

In preferred embodiments, the therapeutically effective amount provides a half maximal inhibitory concentration ($IC_{50}$) for sEH and a half maximal effective concentration ($EC_{50}$) for PPARγ that are less than 1.0 micromolar in the subject.

In another embodiment, the invention encompasses the use of an inventive N-benylbenzamide compound for the manufacture of a medicament for treating diabetes in a subject. As well, the invention further contemplates compounds according to the invention for use in treating diabetes in a subject In yet another aspect, the invention provides a method for simultaneously-modulating soluble epoxide hydrolase (sEH) and peroxisome proliferator-activated receptor gamma (PPARγ) activities in a subject, comprising administering to a subject a therapeutically effective amount of an inventive N-benzylbenzamide compound, wherein soluble epoxide hydrolase (sEH) and peroxisome proliferator-activated receptor gamma (PPARγ) are simultaneously-modulated by the compound in the subject.

In preferred embodiments, the therapeutically effective amount provides a half maximal inhibitory concentration ($IC_{50}$) for sEH and a half maximal effective concentration ($EC_{50}$) for PPARγ that are less than 1.0 micromolar in the subject.

In another embodiment, the invention encompasses the use of an inventive N-benylbenzamide compound for the manufacture of a medicament for simultaneously-modulating soluble epoxide hydrolase (sEH) and peroxisome proliferator-activated receptor gamma (PPARγ) activities in a subject. As well, the invention further contemplates compounds according to the invention for use in simultaneously-modulating soluble epoxide hydrolase (sEH) and peroxisome proliferator-activated receptor gamma (PPARγ) activities in a subject.

Other objects, features and advantages of the present invention will become apparent after review of the specification, claims and drawings.

BRIEF DESCRIPTION OF THE DRAWINGS

FIG. 2 shows 3T3-L1 mouse fibroblasts were differentiated in the presence of the different compounds. Subsequently, cells were either stained with a) Oil-Red or b) PPARγ target gene expression (GLUT4, Adiponectin, FABP4, LPL) was determined by qPCR analysis. c) Remaining concentration of compound 1c after incubation with Spargue-Dawley rat liver microsomes. d) Plasma concentration of compound 1c in mice, after a single p.o. application of 30 mg/kg bw. to three animals per two time points. e) Expression of the PPARγ target gene CD36 in mouse liver after single application of compound 1c (30 mg/kg bw; 8 h; three animals). f) EET/DHET ratio in mouse plasma after a single p.o. application of compound 1c (30 mg/kg bw; three animals per two time points). Shown are mean values±s.e.m. of three independent experiments.

FIG. 6 shows Landmark structures for design of novel dual ligand. GSK1997132B, a non-acidic PPARγ agonist. GSK2188931B, an in vivo active sEH inhibitor. KCL, a PPARα agonist, containing the benzylbenzamide moiety. 1c, the first novel dual ligand and origin of SAR.

FIG. 16 provides comparative in vitro and in vivo data for RB394 analysis.

DETAILED DESCRIPTION OF THE INVENTION

I. In General

Figure 1:
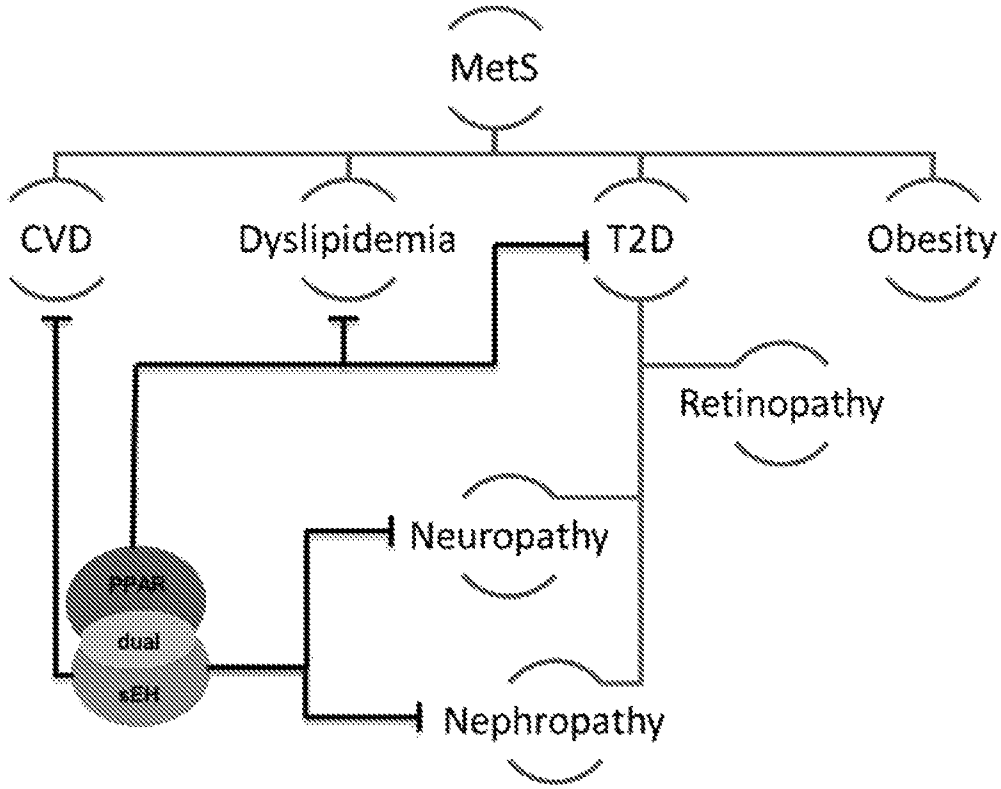
FIG. 1 illustrates MetS cluster diseases and proposed multi-pathogenic interaction by dual modulation of sEH and PPARγ.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The inventors herein disclose novel N-benzylbenzamides, compositions containing those compounds, methods of synthesizing such compounds, and the use of such compounds in treating MetS cluster diseases, including diabetes. The inventors have shown that compounds according to the invention exhibit therapeutic effects and are well-tolerated in relevant rodent models. While not adopting any one mode of operation herein, the inventive compounds have been been demonstrated by the inventors to be dual modulators of sEH and PPARγ.

The main side effect of known PPARγ activators is water retention resulting in weight gain and edema. Fortunately, sEH inhibition and EETs are natriuretic and positively influence water and electrolyte homeostasis[64,65]. Imig et al. already showed in spontaneously hypertensive obese (SHROB) rats that the combination therapy of a sEH inhibitor (t-AUCB) and a PPARγ agonist (rosiglitazone) lowered blood pressure, reduced systemic glucose, TG and FFA. Using these three biomarkers he also demonstrated renoprotective effects by attenuating renal injury. Remarkably, an additional positive synergistic effect of the combination compared to the single sEH/PPARγ therapies was reported here[66]. The inventors have now investigated the potential of dual sEH/PPARγ therapeutics and their unexpected findings, in part, serve as the basis for the present invention.

As used herein, "subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

As used herein, "administering" or "administration" includes any means for introducing a compound of the present invention into the body, preferably into the systemic circulation. Examples include but are not limited to oral, buccal, sublingual, pulmonary, transdermal, transmucosal, as well as subcutaneous, intraperitoneal, intravenous, and intramuscular injection.

A "therapeutically effective amount" means an amount of a compound that, when administered to a subject for treating a disease or condition, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatments. Treating includes the administration of a compound of present invention to prevent the onset of the symptoms or complications, alleviating the symptoms or complications, or eliminating the disease, condition, or disorder.

A compound is administered to a patient in a therapeutically effective amount. A compound can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. Further, the dose of the compound can be varied over time. A compound can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about two grams of the active ingredient, and preferably comprises from about 200 milligrams to about 1.0 gram of the active ingredient.

A preferred dosage for humans would be in the low mg/kg range administered orally once daily. Twice daily would also be acceptable.

To improve water solubility, the preferred compounds can be formulated with cyclodextrins or cyclodextrin-derived products, derivatized with substituents such as polyethylene glycols or other polar functionality, or included in liposomes. For oral delivery, the compounds may be modified with lipophilic functionality or conjugated to actively absorbed molecules. Other approaches are discussed in "Strategies to improve oral drug bioavailability", Isabel Gomez-Orellana, Expert Opinion on Drug Delivery, May 2005, Vol. 2, No. 3: Pages 419-433, which is incorporated by reference herein.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein. The kit also comprises a container for the separate compositions, such as a divided bottle or a divided foil packet.

Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered micro-chip memory coupled with a liquid crystal readout, or audible reminder signal which, for example, reads out the date that the last daily dose has been taken and/or reminds one when the next dose is to be taken.

The compounds of the present invention, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques. For example, the compositions of the present invention can be administered to a subject by brain (via vPAG) injections, intrathecal injections, intraperitoneal injections, or blood injections.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsion in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

The compounds according to the present invention may also contain adjuvants such as preserving, wetting, emulsifying, and/or dispersing agents, including, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin. In particular, liposomes, mysomes and emulsifiers can be used in to make the present compounds more soluble for delivery.

Dosage forms can include solid or injectable implants or depots. In preferred embodiments, the implant comprises an effective amount of an active agent and a biodegradable polymer. In preferred embodiments, a suitable biodegradable polymer can be selected from the group consisting of a poly aspartate, polyglutamate, poly(L-lactide), a poly(D,L-lactide), a poly(lactide-co-glycolide), a polY(E-caprolactone), a polyanhydride, a poly(beta-hydroxy butyrate), a poly(ortho ester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage form, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture.

Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and U.S. Pat. No. 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Tablets can be Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in microencapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et aI., Aliment. Pharmacol. Therap. (1987) 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et aI., J. Med. Chem. (1984) 27:261-268) and a variety of naturally available and modified polysaccharides (see PCT application PCT/GB89100581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like.

Besides such inert diluents, the compounds of the present invention can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Compositions for rectal or vaginal administration can be prepared by mixing a compound of the present invention and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active ingredient. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of a compound according to the present invention include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmalmically administrable formulations comprise the active ingredient in microcrystalline form or in a liposomal preparation.

Pharmaceutical compositions of the invention formulated for pulmonary delivery can provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the compounds of the present invention may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, camauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The compounds of the present invention and the pharmaceutically acceptable salts of the same, can be administered to a patient at dosage levels in the range of from about 0.01 to about 1,000 mg per day. For a normal adult human having a body weight of about 70 kg, a dosage in the range of from about 0.01 to about 300 mg is typically sufficient, with 1-10 mg/kg a preferred dosage. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the compounds of the present invention are administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to mobilize lipids in the cell arrives, directly or indirectly at the cell. The minimum amount varies with the identity of the compounds.

The specific dosage and dosage range that can be used depends on a number of factors, including the requirements of the patient, the severity of the condition being treated, and the pharmacological activity of the compound being administered. The determination of dosage ranges and optimal dosages for a particular patient is well within the ordinary skill of one in the art in view of this disclosure. It is understood that the ordinarily skilled physician or veterinarian will readily determine and prescribe an effective amount of the compound to mobilize lipid stores, induce weight loss, or inhibit appetite in the patient. In so proceeding, the physician or veterinarian can, for example, prescribe a relatively low dose at first, subsequently increasing the dose until an appropriate response is obtained. It is further understood, however, that the specificdose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

The compounds of the present invention are particularly useful when formulated in the form of a pharmaceutical injectable dosage, including a compound described and claimed herein in combination with an injectable carrier system. As used therein, injectable and infusion dosage forms (i.e., parenteral dosage forms) include, but are not limited to, liposomal injectables or a lipid bilayer vesicle having phospholipids that encap lulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution in section is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vehicle usually containing phospholipids used to encapsulate an active drug substance (either within a lipid bilayer or in an aqueous space) are formed. Suspension sonicated injection is a liquid preparation (suitable for injection) containing solid particles dispersed throughout a liquid phase, whereby the particles are insoluble. In addition, tile product may be sonicated as a gas is bubbled through the suspension resulting in the formation of micro spheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The inventors presently describe and claim a multi-target approach to treat MetS cluster diseases, including diabetes, by administration of certain N-benzylbenzamides to affect the simultaneous modulation of soluble epoxide hydrolase (sEH) and peroxisome proliferator-activated receptor γ (PPARγ).

Accordingly, the invention encompasses, in a first aspect, certain compounds having the structure:

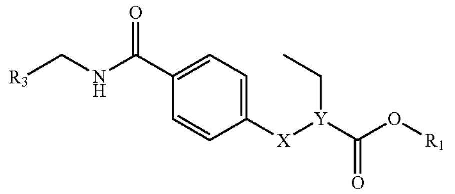

wherein: X—Y is CH═C or $CH_2$—CH; $R_1$ is $CH_2CH_3$, $CH_3$ or H; and $R_3$ is a fluoro-substituted aryl group; or a salt thereof. The fluoro-substituted aryl group at $R_3$ is preferably a phenyl group comprising a trifluoromethyl- or trifluoromethoxy-substitution, even more preferably substituted at the phenyl group's ortho position.

In certain compounds according to the invention, $R_3$ is:

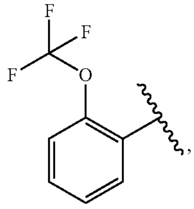
,
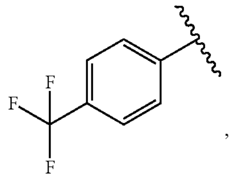
,
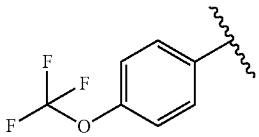
,
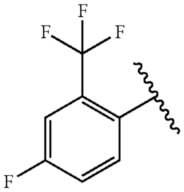
or
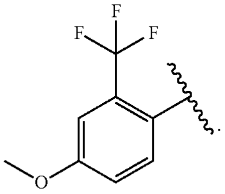 [SMILES: *c1ccc(OC)cc1C(F)(F)F]
.

A preferred compound of the invention calls for $R_3$ to be

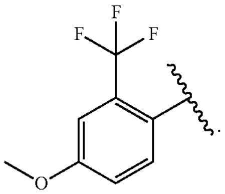 [SMILES: *c1ccc(OC)cc1C(F)(F)F]
.

Compounds of the invention include those wherein: X—Y is $CH_2$—CH and $R_1$ is $CH_2CH_3$; X—Y is CH═C and $R_1$ is $CH_2CH_3$; X—Y is $CH_2$—CH and $R_1$ is H; and X—Y is CH═CH and $R_1$ is H.

A particularly preferred compound according to the invention calls for X—Y to be $CH_2CH$, $R_1$ to be H, and $R_3$ to be

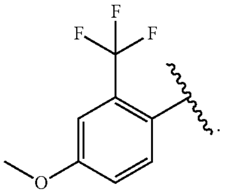 [SMILES: *c1ccc(OC)cc1C(F)(F)F]
.

In particularly preferred embodiments, the inventive compound exhibits a half maximal inhibitory concentration ($IC_{50}$) for soluble epoxide hydrolase (sEH) and a half maximal effective concentration ($EC_{50}$) for peroxisome proliferator-activated receptor gamma (PPARγ) that are less than 1.0 micromolar when administered to a subject.

In another aspect, the invention provides a composition comprising: (a) an inventive N-benzylbenzadmide compound; and (b) a pharmaceutically acceptable carrier. In preferred embodiments, this composition is formulated as an oral dosage.

In yet another aspect, the invention provides a method of treating metabolic syndrome in a subject, comprising administering to a subject a therapeutically effective amount of an inventive N-benzylbenzamide compound, wherein soluble epoxide hydrolase (sEH) and peroxisome proliferator-activated receptor gamma (PPARγ) are simultaneously-modulated by the compound thereby treating metabolic syndrome in the subject.

In preferred embodiments, the therapeutically effective amount provides a half maximal inhibitory concentration ($IC_{50}$) for sEH and a half maximal effective concentration ($EC_{50}$) for PPARγ that are less than 1.0 micromolar in the subject.

In another embodiment, the invention encompasses the use of an inventive N-benylbenzamide compound for the manufacture of a medicament for treating MetS in a subject. As well, the invention further contemplates compounds according to the invention for use in treating MetS in a subject.

In yet another aspect, the invention provides a method of treating diabetes in a subject, comprising administering to a subject a therapeutically effective amount of an inventive N-benzylbenzamide compound, wherein soluble epoxide hydrolase (sEH) and peroxisome proliferator-activated receptor gamma (PPARγ) are simultaneously-modulated by the compound thereby treating diabetes in the subject.

In preferred embodiments, the therapeutically effective amount provides a half maximal inhibitory concentration ($IC_{50}$) for sEH and a half maximal effective concentration ($EC_{50}$) for PPARγ that are less than 1.0 micromolar in the subject.

In another embodiment, the invention encompasses the use of an inventive N-benylbenzamide compound for the manufacture of a medicament for treating diabetes in a subject. As well, the invention further contemplates compounds according to the invention for use in treating diabetes in a subject.

In yet another aspect, the invention provides a method for simultaneously-modulating soluble epoxide hydrolase (sEH) and peroxisome proliferator-activated receptor gamma (PPARγ) activities in a subject, comprising administering to a subject a therapeutically effective amount of an inventive N-benzylbenzamide compound, wherein soluble epoxide hydrolase (sEH) and peroxisome proliferator-activated receptor gamma (PPARγ) are simultaneously-modulated by the compound in the subject.

In preferred embodiments, the therapeutically effective amount provides a half maximal inhibitory concentration ($IC_{50}$) for sEH and a half maximal effective concentration ($EC_{50}$) for PPARγ that are less than 1.0 micromolar in the subject.

In another embodiment, the invention encompasses the use of an inventive N-benylbenzamide compound for the manufacture of a medicament for simultaneously-modulating soluble epoxide hydrolase (sEH) and peroxisome proliferator-activated receptor gamma (PPARγ) activities in a subject. As well, the invention further contemplates compounds according to the invention for use in simultaneously-modulating soluble epoxide hydrolase (sEH) and peroxisome proliferator-activated receptor gamma (PPARγ) activities in a subject.

Various exemplary embodiments of compositions and methods according to this invention are now described in the following examples. In these embodiments, specific products identified by Arabic numerals (e.g., 1, 2, 3, etc.) refer to the specific structures so identified in the following description, particularly in the Tables below and the appended claims.

III. Examples

The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

Example 1: N-Benzylbenzamides: A Novel Fused Scaffold for Orally Available Dual sEH/PPARγ Modulators The metabolic syndrome (MetS) is a multifactorial disease cluster consisting of dyslipidemia, cardiovascular disease, type 2 diabetes mellitus and obesity. Pharmacological intervention in the MetS is dependent on numerous drugs, thus polypharmacy is an obvious problem in the treatment of MetS patients. This study focuses on the dual target approach to accomplish a more efficient therapy for MetS. The two targets addressed by dual ligand design are the soluble epoxide hydrolase (sEH) and the peroxisome proliferator-activated receptor type γ (PPARγ). Structure activity relationship studies on both targets were performed resulting in an equipotent submicromolar (sEH IC50=0.3±0.05 μM/PPAR EC50=0.3±0.09 μM) propionic acid benzylbenzamide derivative. Evaluation in vitro and in vivo displayed good ADME properties qualifying the novel dual modulator as pharmacological tool compound for long term animal models of MetS.

Identification of a Fused sEH/PPARγ Pharmacophore

The identification of a common pharmacophore is a challenging task in the design process of dual modulators. GlaxoSmithKline published in 2011 a PPARγ agonist (GSK1997132B) without the commonly used acidic head group, for blood-brain barrier penetration reasons (FIG. 6). The binding-mode of the ligand co-crystallized indicates that a benzylamide moiety is able to replace the acidic head group while retaining full agonist properties of the ligand. Almost all reported sEH inhibitors are epoxide mimetics, containing an urea or amide structure as pharmacophore. In this situation the benzylamide structure would represent a merged pharmacophore for sEH and PPAR, which is the best starting point in dual ligand design. Several benzylamides were reported as sEH inhibitors, the most advanced compound of this study is GSK2188931B (FIG. 6). Based on the reported SAR, we adapted the ortho trifluoromethyl benzyl substitution important for inhibitory activity on sEH and metabolic stability of the compounds. Finally, a study from Kyorin Pharmaceutical Co. Ltd. illustrates substituted benzylamides (KCL) used for PPARα activation, however exhibiting the classical PPAR binding mode (FIG. 6). Nevertheless this information motivated us towards a molecule design shown in FIG. 6, using N-benzylbenzamide moiety as a merged pharmacophore.

Synthesis

Figure 7:
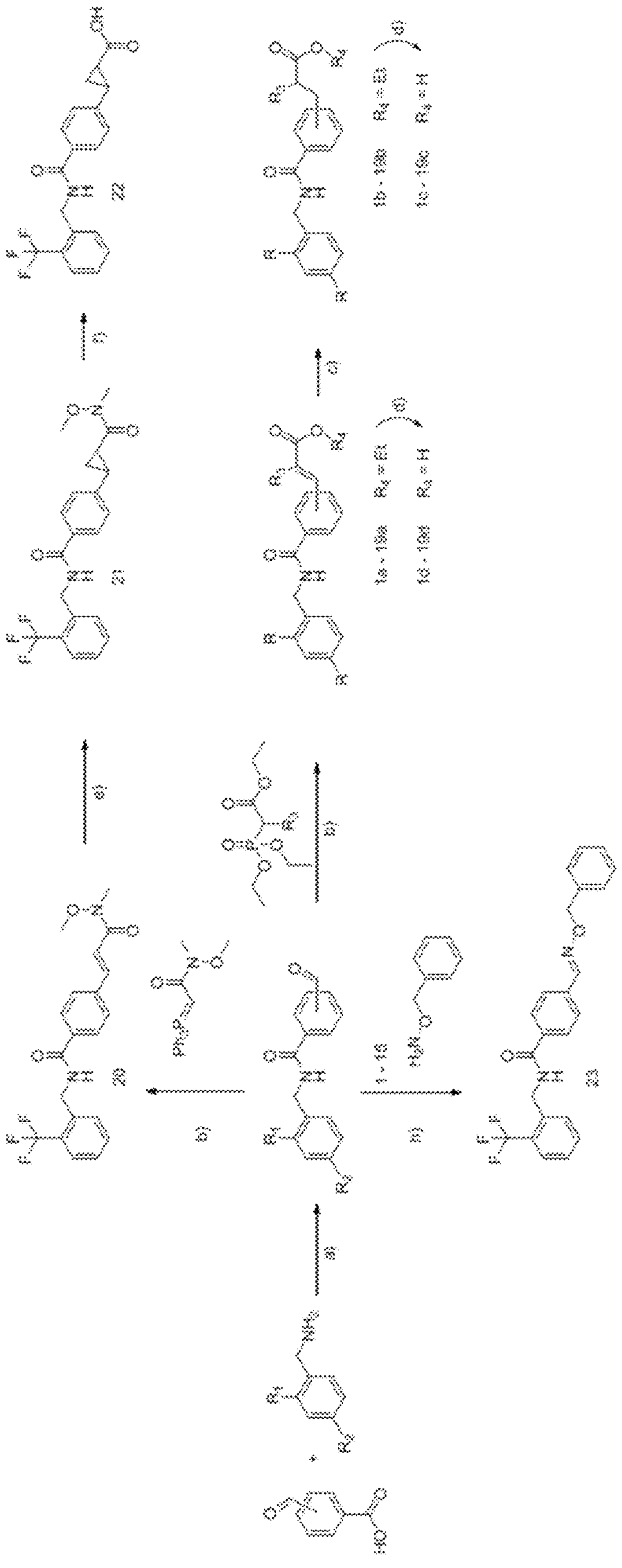
FIG. 7 shows (a) IBCF, TEA, dry DCM, 12 h; (b) NaH, THF, 0° C., 2 h; (c) Hz, Pt/C, EtOH, 12 h; (d) MeOH|H2O|THF, KOH, MW, 100° C., 30 min; (e) $Me_3SO^+ I^-$, NaH, DMSO, 6 h; (f) KOH, EtOH|$H_2O$, 16 h; (g) Diethyl benzylphosphonate, NaH, THF, 0° C., 2 h (h) DIPEA, 16 h.
Figure 8:
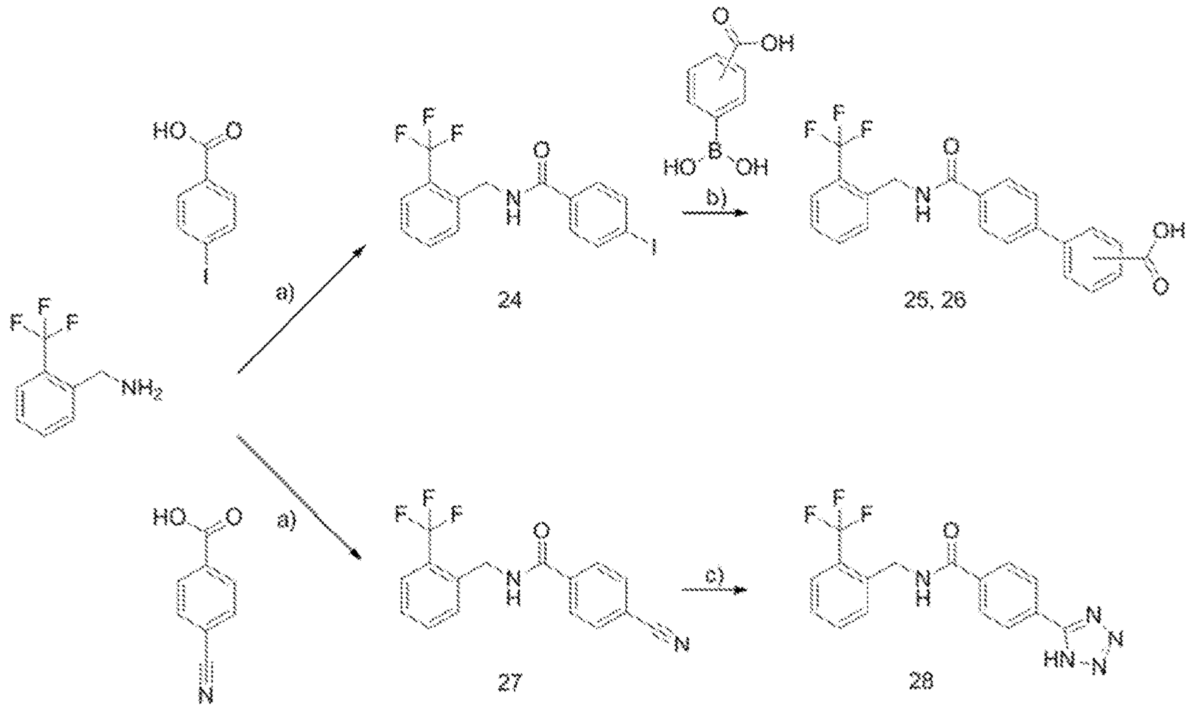
FIG. 8 shows (a) EDC, DMAP, dry DCM, 12 h; (b) Pd(AcO)2, K2CO3, Aceton|H2O, 65° C., 1 h; (c) NaN3, NH3Cl, DMF, 12 h.

Synthetic routes to prepare all investigated N-benzylbenzamide derivatives are shown in FIGS. 7 and 8. The main derivatives are α-substituted N-benzylbenzamide propionic acids (1c-19c), prepared in 4 steps. For each kind of derivative an N-benzylbenzamide cinnamate (1a-19a) and an N-benzylbenzamide propanoate (1b-19b) type compound automatically appeared through the synthetic route. These compounds were additionally evaluated in vitro for an extended SAR exploration. The N-benzylbenzamide cinnamates (1a-19a) were also hydrolyzed to their corresponding N-benzylbenzamide cinnamic acids (1d-19d), to complete the diversity in this structural field and extend the activity data landscape.

The synthesis of N-benzylbenzamide propionic acids (1c-19c) (FIG. 7) starts with the activation of either 4-formylbenzoic acid or 3-formylbenzoic acid with isobutylchloroformiat (IBCF) in DCM under dry basic conditions, followed by the addition of various 2- or 2, 4-substituted benzylamines to produce the compounds 1-15[71,72]. By a Wittig reaction, using triethyl 2-phosphonobutyrat, the compounds 1-15 were turned into their corresponding N-benzylbenzamid cinnamate derivatives (1a-15a)[73,74]. With the same reaction type 4 different alpha substituents (hydrogen, methyl, propyl and phenyl) were introduced in the N-benzylbenzamid cinnamate scaffold, while the benzylamine fragment was fixed at 2-trifluoromethyl substitution (16a-19a). All α, β-unsaturated carbonyl compounds (1a-19a) were reduced with Palladium on carbon catalyst in dry EtOH under hydrogen atmosphere to maintain the N-benzylbenzamid propanoate structural class (1b-19b)[74]. The deprotection of either the N-benzylbenzamid cinnamate (1a-19a) or the N-benzylbenzamid propionate (1b-19b) to their corresponding acids, the N-benzylbenzamid cinnamic acids (1d-19d) and the N-benzylbenzamid propionic acids (1c-19c), was carried out by the same microwave reaction under basic conditions with a solvent mixture of MeOH|$H_2O$|THF in the ratio 1|2|1[75].

The α, β-cyclopropan acid derivative (22) was synthesized in 3 steps (FIG. 7)[76,77]. Starting with a Wittig reaction of compound 1 and N-methoxy-N-methyl(triphenylphosphoranylidene)acetamide compound 20 was obtained. Followed by a Corey-Chaykovsky reaction the derivative 21 was produced. After a basic deprotection in an EtOH|$H_2O$ solvent mixture the final product (22) was achieved[78].

The non-acidic o-(benzylhydroxyl)imin derivative (23) was synthesized by a Leuckart-Wallach reaction[79] of compound 1 and o-benzylhydroxylamine hydrochloride, shown in FIG. 7.

The biphenyl ortho- and meta-acid derivatives (25, 26) were synthesized in a two-step route shown in FIG. 8. In the first step 4-iodobenzoic acid was activated by EDC under DMAP catalysis and combined with 2-trifluoromethylbenzylamin to compound 24[80]. Through a Suzuki coupling of compound 24 with 4-carboxy as well as 3-carboxybenzenboronic acid the desired biphenyl acid derivatives (25, 26) were achieved[81,82].

The tetrazol derivative (28) was also produced in a two-step synthesis (FIG. 8). The nitrile intermediate (27) was prepared under the same conditions as compound (24). For the tetrazol synthesis $NaN_3$ and $NH_4Cl$ in DMF was used[83].

Results & Discussion

Based on the previously described hypothesis the first prototype of a non-acidic sEH/PPAR dual modulator (27) was designed and synthesized. In vitro inhibition could only be shown on sEH ($IC_{50}$=0.064 all PPAR subtypes remained unaffected (Table 1). After the reintroduction of the acidic head group and extension of the aromatic core a new set of two isomeric compounds was prepared (25, 26). The sEH inhibition dropped almost one order of magnitude from 0.17 µM to 1 µM, by switching the acidic head group from para to meta position. The para position of the acidic head group seems to fit more properly in the lipophilic tunnel-shaped sEH binding pocket[84,85]. PPAR activation of the para and meta derivative at a concentration of 10 µM was determined around 30% (compared to pioglitazone), indicating, that acidic functionality or at least an H-bond acceptor is still necessary for PPAR activation. However, assuming the classical PPAR binding mode with a carboxylic group responsible for activation, the activity values should differ more among both PPAR subtypes alpha and gamma[86]. In the next designed molecule (28) the core fragment was reduced to one aromatic ring, and the carboxylic acid was substituted by a tetrazole bioisostere. These changes caused a loss of PPAR activation and a sEH inhibition in the micromolar range ($IC_{50}$=5 µM) (Table 1). The acidic head of compound 28 is orientated sideways, similar to compound 26. This alignment of the polar moiety towards the hydrophobic tunnel-shaped sEH binding pocket may cause the single digit micromolar inhibition value of compound 26 & 28. To improve the obvious lack of PPAR activation without expansion of the molecular weight, the introduction of an often successfully used acidic moiety, the α-substituted propionic acid[70,87], has been employed. As mentioned in the synthesis paragraph, 4 types of carbonyl derivatives were produced for each substitution pattern of the propionic acid structural class. In the first quartet (1a-d) an equipotent subtype selective sEH/PPARγ dual modulator with full agonistic PPARγ properties and potency on both targets in the single digit micromolar range was found (1c) (Table 2). In this structural class, sEH inhibition improved by one order of magnitude from acid to ester derivative, which can be explained by the mainly lipophilic sEH binding pocket[88]. Except 1a all derivatives of this series showed similar activations on PPARγ, most remarkable is the equivalent potency of compound 1b and 1c. Full PPARγ activation by the ester derivative could be an indication for an alternative PPAR binding mode with a minor impact of the acidic moiety. It is unlikely that the ester becomes hydrolyzed by COS-7 cells due to the fact that we never observed activity of ethyl esters in previous projects where this assay system has been employed nor we have found an example for this case in literature[74,86,89-91] The production of a set of central meta substituted isomers (15a-d) showed no improvement of activity and loss of PPARγ selectivity (Table 2). Acceptable potency at both targets, small molecular weight, PPARγ subtype selectivity and reasonable water solubility under assay conditions qualified compound 1c as a good starting point for pharmacological profiling.

TABLE 1

Inhibition and activation values of dual sEH/PPAR modulators from first structural series and two non-acidic intermediate compounds.

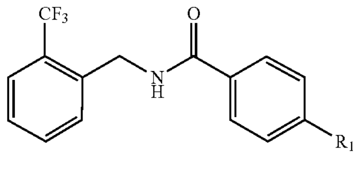

| compd. | $R_1$ | w.s. [µM] | $IC_{50}$ sEH [µM] | $EC_{50}$ PPARα [µM] ($E_{max}$-%) | $EC_{50}$ PPARδ [µM] ($E_{max}$-%) | $EC_{50}$ PPARγ [µM] ($E_{max}$-%) |
|---|---|---|---|---|---|---|
| 23 | 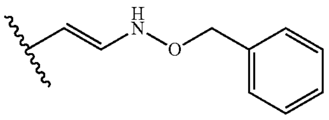 [SMILES: */C=C/NOCc1ccccc1] | n.t. | 0.064 ± 0.015 | i.a. | i.a. | i.a. |
| 25 | 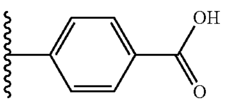 [SMILES: *c1ccc(C(=O)O)cc1] | 5 | 0.17 ± 0.006 | i.a. | i.a. | @ 10 µM (30%) |
| 26 | 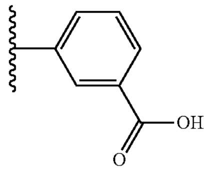 [SMILES: *c1cccc(C(=O)O)c1] | n.t. | 1 ± 0.1 | i.a. | i.a. | @ 10 µM (28%) |

TABLE 1-continued

Inhibition and activation values of dual sEH/PPAR modulators from first structural series and two non-acidic intermediate compounds.

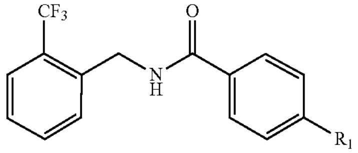

| compd. | $R_1$ | w.s. [μM] | $IC_{50}$ sEH [μM] | $EC_{50}$ PPARα [μM] ($E_{max}$-%) | $EC_{50}$ PPARδ [μM] ($E_{max}$-%) | $EC_{50}$ PPARγ [μM] ($E_{max}$-%) |
|---|---|---|---|---|---|---|
| 28 | 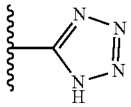 [SMILES: *c1nnn[nH]1] | 500 | 5 ± 0.7 | i.a. | i.a. | i.a. |
| 20 | 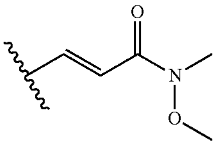 [SMILES: */C=C/C(=O)N(C)OC] | n.t. | 0.07 ± 0.02 | i.a. | i.a. | i.a. |
| 21 | 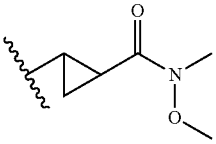 [SMILES: *C1CC1C(=O)N(C)OC] | n.t. | 0.08 ± 0.004 | i.a. | i.a. | @ 10 μM (30%) |

TABLE 2

Inhibition and activation values of dual sEH/PPAR modulators from Hit compound and its meta derivative

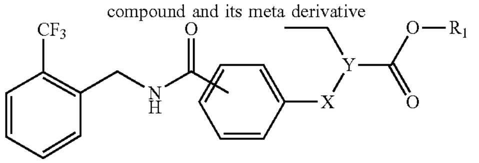

a) X-Y: CH═C; $R_1$: $CH_2CH_3$
b) X-Y: $CH_2$—CH; $R_1$ = $CH_2CH_3$
c) X-Y: $CH_2$—CH; $R_1$ = H
d) X-Y: CH═CH; $R_1$ = H

| compd. | subst. | w.s. [μM] | $IC_{50}$ sEH [μM] | $EC_{50}$ PPARα [μM] ($E_{max}$-%) | $EC_{50}$ PPARδ [μM] ($E_{max}$-%) | $EC_{50}$ PPARγ [μM] ($E_{max}$-%) |
|---|---|---|---|---|---|---|
| 1a | para | n.t. | 0.063 ± 0.003 | i.a. | i.a. | @ 10 μM (20%) |
| 1b | | n.t. | 0.044 ± 0.005 | i.a. | i.a. | 1.8 ± 0.2 (86%) |
| 1c | | 100 | 1.6 ± 0.2 | i.a. | i.a. | 4.8 ± 2.1 (127%) |
| 1d | | n.t. | 0.12 ± 0.01 | i.a. | i.a. | 2.2 ± 0.3 (117%) |
| 15a | meta | n.t. | 0.04 ± 0.006 | n.t. | n.t. | n.t. |
| 15b | | n.t. | 0.027 ± 0.002 | i.a. | i.a. | @10 uM (40%) |
| 15c | | n.t. | 0.9 ± 0.08 | @10 μM (34%) | i.a. | 6.4 ± 1.3 (60%) |
| 15d | | n.t. | 0.4 ± 0.1 | n.t. | n.t. | n.t. |

Figure 9:
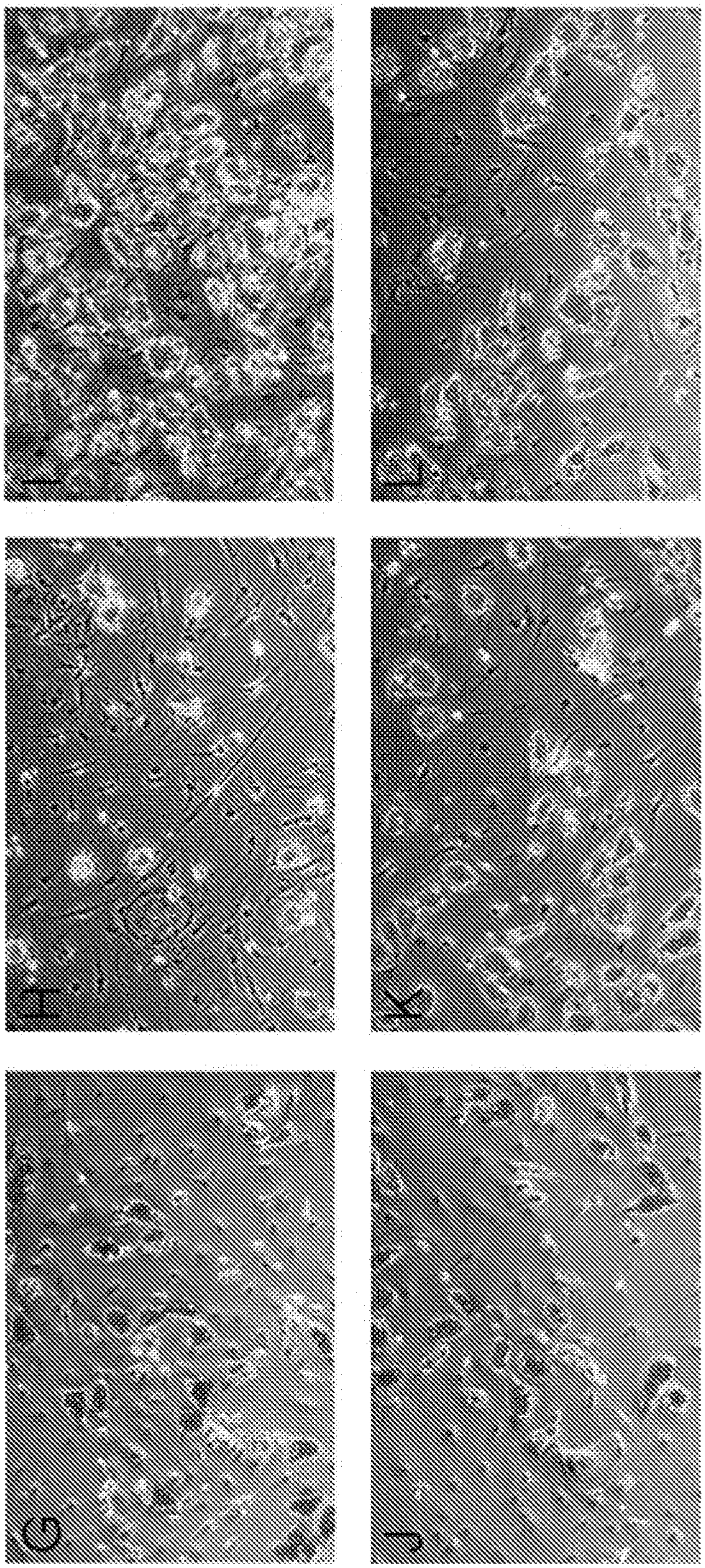
FIG. 9 shows Oil Red O staining of human differentiated primary adipocytes. Preadipocytes were differentiated in the presence of various compounds. G: untreated control; H: 10 μM CIU (sEH inhibitor); I: 2 μM rosiglitazone (PPARγ agonist); J: 1 μM 1c; K: 5 μM 1c; L: 10 μM 1c. One representative experiment out of three is shown. The picture magnified 100-times.
Figure 10:
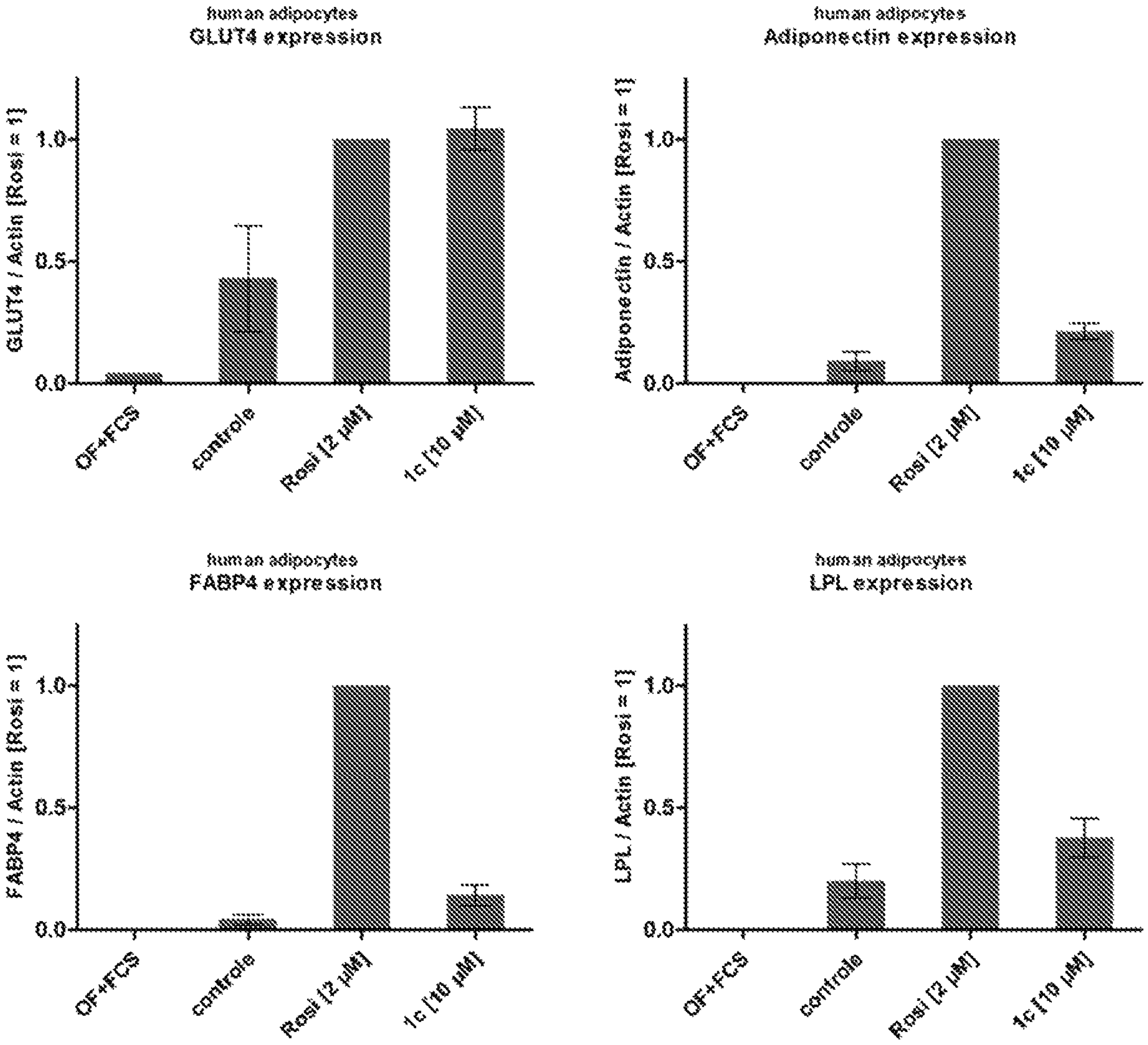
FIG. 10 shows qPCR analysis of PPARγ target genes (GLUT4, Adiponectin, FABP4, LPL) in human primary adipocytes differentiated in the presence of different stimuli. OF+FCS represents the differentiation of the cells only in basal medium. The control shows the experiment without PPARγ stimuli. Shown are mean values±s.e.m. each of three independent experiments.
Figure 11:
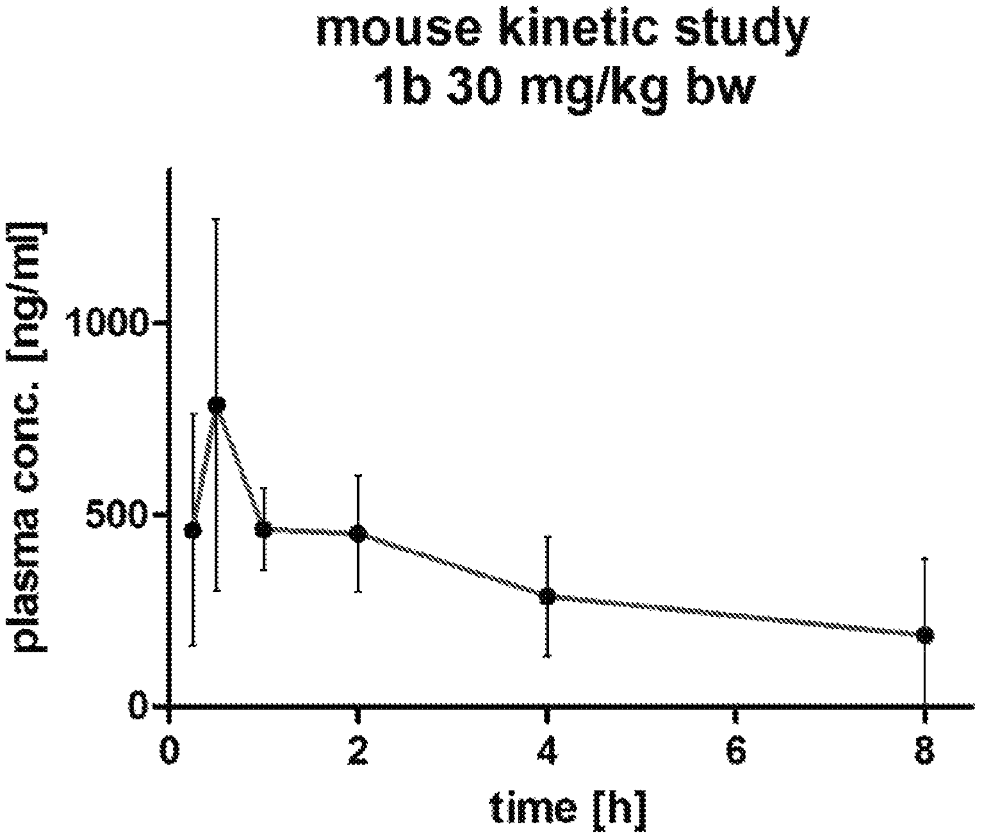
FIG. 11 shows PK of 1c after p.o. application of 1b (single dose of 30 mg/kg) in mice. Shown are mean values±s.e.m. from plasma of three mice per two timepoints.
Figure 12:
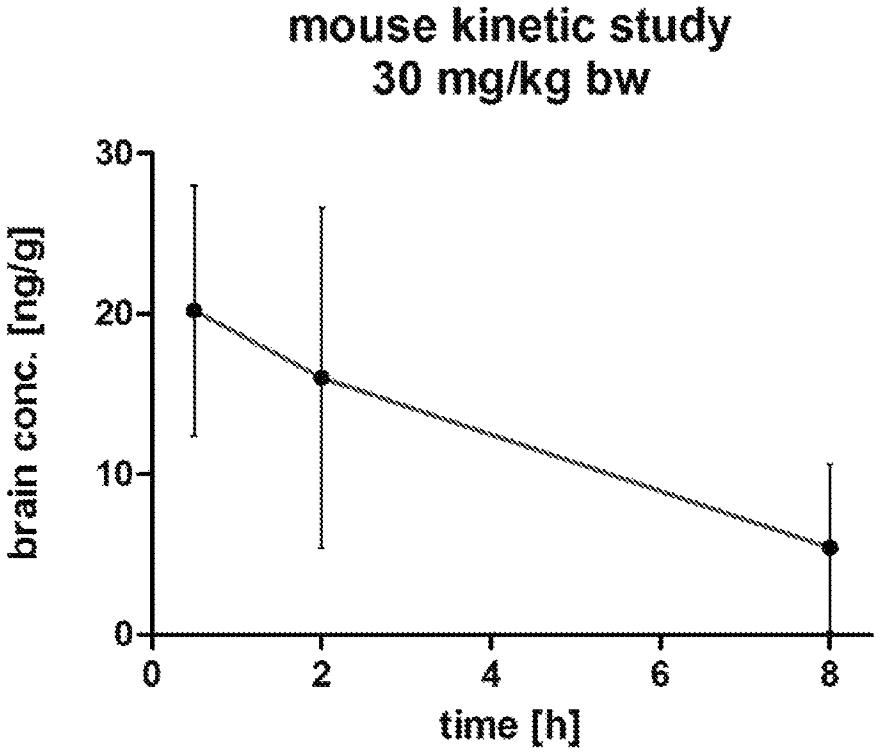
FIG. 12 shows brain concentration of 1c after p.o. application of 1b (single dose of 30 mg/kg) in mice. Shown are mean values±s.e.m. from brain tissue of three mice per timepoint.

Compound 1c did not impair cell viability of HepG2 cells up to a concentration of 30 indicated by the WST-1 assay[92]. In Spargue-Dawley rat liver microsomes the in vitro metabolic stability of compound 1c has been determined (FIG. 2). After 1 h ~92% of 1c remained intact. PPARγ activation by 1c was evaluated in different cellular systems by measuring the effect on adipocyte differentiation. The capability of 1c to trigger adipocyte differentiation in murine 3T3-L1 fibroblasts and human primary preadipocytes was determined and compared to rosiglitazone (PPARγ agonist)[86] and N-cyclohexyl-N'-iodophenyl urea (CIU, sEH inhibitor)[93]. In 3T3-L1 fibroblasts a dose-dependent effect (1-10 μM) of 1c on adipocyte differentiation could be demonstrated (FIG. 2*a*). Differentiated adipocytes were visualized using Oil-Red O staining. At a 10 μM concentration of 1c a lower amount of adipocytes accumulated lipids compared to a 2 μM concentration of rosiglitazone. Surprisingly CIU was also able to start adipocyte differentiation with no direct PPARγ activation. A hypothesis to this phenomenon is the subsequent PPARγ activation through a EET-PPARγ pathway[58,94,60]. In human adipocytes a similar effect of 1c was observed (see FIG. 9). By Oil-Red O staining a dose dependent (1-10 μM) effect to the adipocyte differentiation was determined, which was also lower compared to 2 μM rosiglitazone. In contrast to murine 3T3-L1 fibroblasts, CIU was not able to start differentiation in human adipocytes. In addition, the expression of four PPARγ target genes (GLUT4, glucose transporter type 4; Adiponectin; FABP4, fatty acid binding protein 4, LPL, lipoprotein lipase) in the differentiated murine and human adipocytes were determined by qPCR analysis as a measure of target activation[95]. In murine 3T3-L1 fibroblasts (FIG. 2*b-e*) 1c dose-dependently activated expression of all target genes analysed. At a concentration of 10 μM 1c showed a slightly lower expression of all 4 PPARγ target genes compared to the rosiglitazone (2 μM) control. In human adipocytes the effect of 1c on the PPARγ target expression was more diverse (see FIG. 10). Here, the upregulation of the GLUT4 expression at a 1c concentration of 10 μM was comparable to the rosiglitazone (2 μM) control. In contrast, Adiponectin, FABP4 and LPL showed only minor effects in the upregulation caused by 1c stimulation. The diverse effect of 1c on the expression of the PPARγ target genes measured will need more detailed research. It is known that certain PPARγ agonists can selectively transactivate a number of PPARγ target genes while sparing others. The physiological consequence of this is not completely understood at the moment and is subject of intensive research at the moment[96,97]. Based on this in vitro profile two in vivo PK/PD studies were carried out in mice. To achieve a prodrug effect, compound 1b, the ethyl ester derivative of 1c, was characterized in vivo. After a single per oral application of 30 mg/kg bw to 9 (RijOrl: SWISS/CD-1) mice (gavage) 1b was not detected in the plasma of the animal at all time points indicating rapid ester hydrolysis. The corresponding acid (1c) appeared in plasma with $C_{max}$=787 ng/ml (~2 μM) after 0.5 h ($t_{max}$), $AUC_{0\rightarrow\infty}$=4026 ng*h/ml, Cl/f=7.5 l/h*kg and $V_z$/f=54.3 l/kg (see FIG. 11). Recently it was shown that PPARγ activation in the CNS is involved in the increased weight gain associated with marketed PPARγ activators by controlling food intake and energy expenditure[98,99]. Therefore, to establish the blood-brain-barrier diffusion capacity of 1c its' concentration was determined in the brains of the treated mice[100,44] Here the concentration of 1c did not exceed 30 ng/g brain tissue (see FIG. 12). This led to the assumption that 1c only poorly penetrates the blood-brain-barrier. Unfortunately, a $C_{max}$=787 ng/ml after 30 mg/kg dosing of 1b indicated its' poor bioavailability. This was probably due to the poor water solubility of 1b. Thus, a second PK/PD study in mice with per oral application of 30 mg/kg bw of 1c (the acidic derivative of 1b) to 9 (RijOrl: SWISS/CD-1) mice (gavage) was performed (FIG. 2). Fortunately, 1c reached a maximum concentration in the mouse plasma of 7200 ng/ml (~20 μM) after 0.5 h ($t_{max}$), which is one order of magnitude higher than the $C_{max}$ of 1b and almost one order of magnitude higher than the in vitro $EC_{50}$ values on both targets. The complete kinetic profile was also improved ($AUC_{0\text{-}43\ \infty}$=15847 ng*h/ml, Cl/f=1.91/h*kg, $V_z$/f=81/kg).

The EET to DHET ratio in plasma gives direct information about the effectivity of sEH inhibition[50]. 8 h after application of 1c to the mice the plasma EET/DHET ratio increased by at least 2-fold (FIG. 2*i*). For determination of PPARγ activation in vivo, the expression of the PPARγ target gene CD36 in liver tissue of the treated mice was quantified by qPCR analysis[95]. The expression increased by at least 2-fold compared to non-treated mice (FIG. 2*h*). In vitro and in vivo characterization of 1c led to a moderate pharmacological profile, with capacity to improve in potency and bioavailability. Therefore the following SAR study was conducted.

TABLE 3

In vitro activity values of dual sEH/PPAR modulators - variation of the α substituent

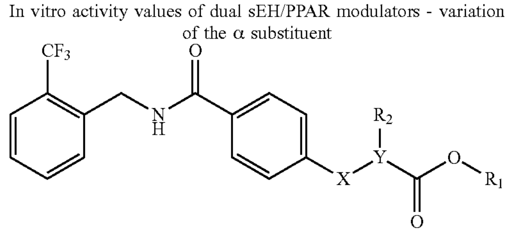

a) X-Y: CH═C; $R_1$: $CH_2CH_3$
b) X-Y: $CH_2$—CH; $R_1$: $CH_2CH_3$
c) X-Y: CH—CH; $R_1$: H
d) X-Y: CH═CH; $R_1$: H

| compd. | $R_2$ | w.s. [μM] | $IC_{50}$ sEH [μM] | $EC_{50}$ PPARα [μM] ($E_{max}$-%) | $EC_{50}$ PPARδ [μM] ($E_{max}$-%) | $EC_{50}$ PPARγ [μM] ($E_{max}$-%) |
|---|---|---|---|---|---|---|
| 16a | H | 2.5 | 0.13 ± 0.005 | i.a. | i.a. | n.t. |
| 16b | | 5 | 0.11 ± 0.003 | i.a. | i.a. | @ 10 μM (38%) |
| 16c | | 500 | 9 ± 1.7 | i.a. | i.a. | @ 10 μM (38%) |
| 16d | | 10 | 0.8 ± 0.05 | i.a. | i.a. | n.t. |
| 17a | $CH_3$ | 10 | 0.1 ± 0.03 | n.t. | n.t. | n.t. |
| 17b | | 10 | 0.25 ± 0.04 | i.a. | i.a. | 8 ± 1.5 μM (110%) |
| 17c | | 500 | 8 ± 1.6 | i.a. | i.a. | 3 ± 0.5 μM (90%) |
| 17d | | 500 | 4.9 ± 0.06 | n.t. | n.t. | n.t. |
| 18a | $CH_2CH_2CH_3$ | 10 | 0.16 ± 0.06 | n.t. | n.t. | n.t. |
| 18b | | 5 | 0.17 ± 0.04 | i.a. | i.a. | 0.9 ± 0.2 (132%) |

TABLE 3-continued

In vitro activity values of dual sEH/PPAR modulators - variation of the α substituent

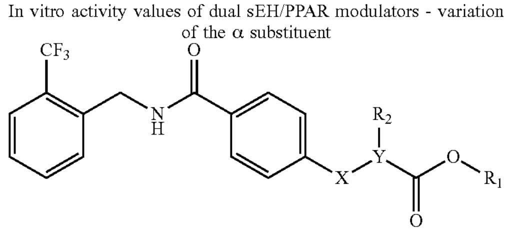

a) X-Y: CH═C; $R_1$: $CH_2CH_3$
b) X-Y: $CH_2$—CH; $R_1$: $CH_2CH_3$
c) X-Y: CH—CH; $R_1$: H
d) X-Y: CH═CH; $R_1$: H

| compd. | $R_2$ | w.s. [μM] | $IC_{50}$ sEH [μM] | $EC_{50}$ PPARα [μM] ($E_{max}$-%) | $EC_{50}$ PPARδ [μM] ($E_{max}$-%) | $EC_{50}$ PPARγ [μM] ($E_{max}$-%) |
|---|---|---|---|---|---|---|
| 18c | | 500 | 5 ± 1.3 | i.a. | i.a. | 1.5 ± 0.4 (180%) |
| 18d | | 5 | 0.7 ± 0.06 | n.t. | n.t. | n.t. |
| 19a | phenyl | 1 | 0.16 ± 0.03 | n.t. | n.t. | n.t. |
| 19b | | 5 | 0.12 ± 0.013 | i.a. | i.a. | 2 ± 0.4 (53%) |
| 19c | | 100 | 2.5 ± 0.5 | i.a. | i.a. | 3 ± 0.9 μM (68%) |
| 19d | | 50 | 0.8 ± 0.01 | n.t. | n.t. | n.t. |
| 22d | X-Y: cyclopropyl | n.t. | 5.5 ± 0.2 | i.a. | i.a. | @ 10 μM (24%) |

Figure 3:
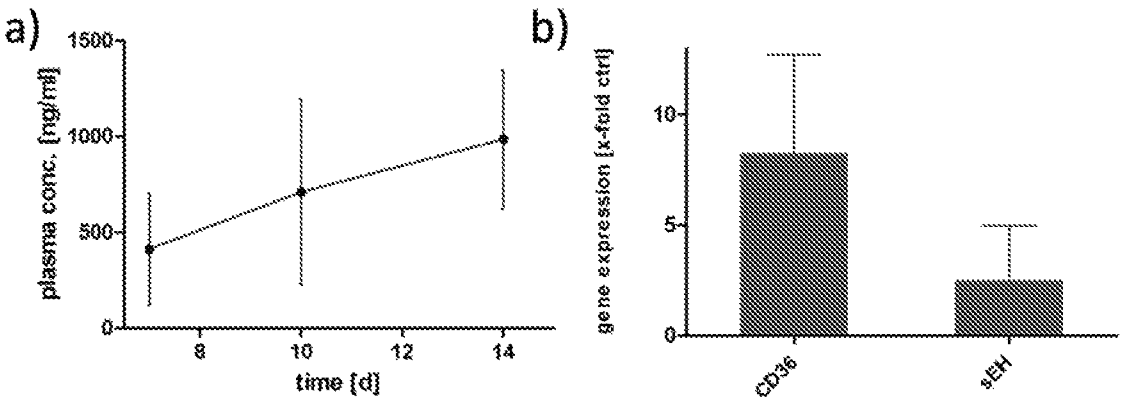
FIG. 3 a) shows plasma concentration of compound 14c, in mice by drinking water application (30 mg/kg bw; 6 animals); b) Expression of the PPARγ target gene CD36 in mouse liver after 14 days 30 mg/kg bw drinking water application of compound 14c.
Figure 13:
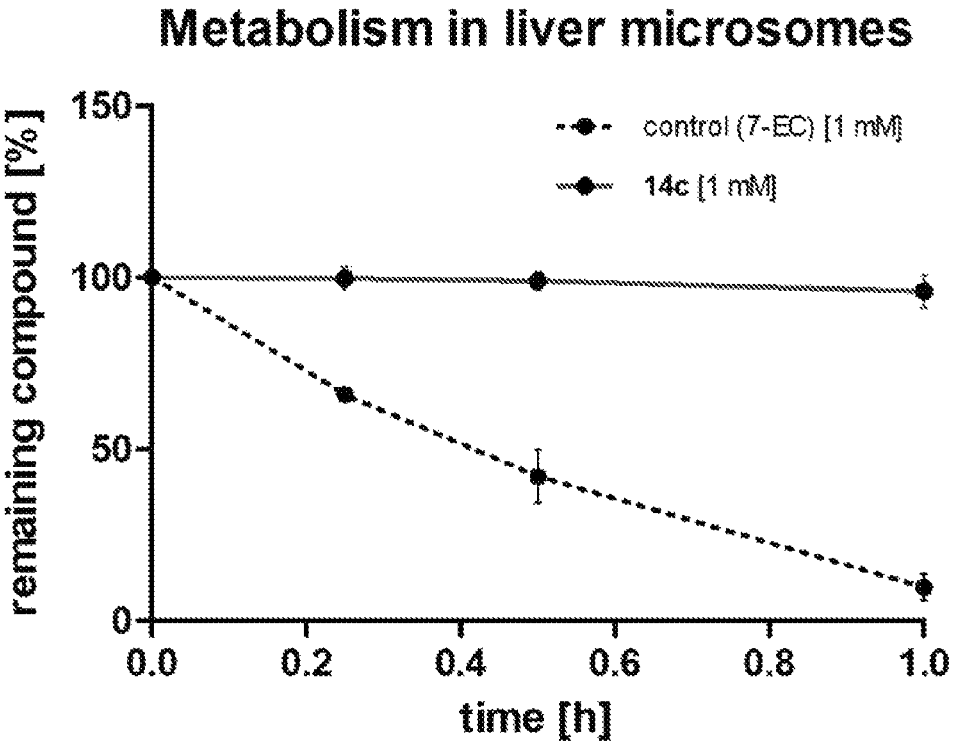
FIG. 13 shows metabolic stability of compound 14c in rat liver microsomes. Shown are mean values±s.e.m. of three independent experiments.
Figure 14:
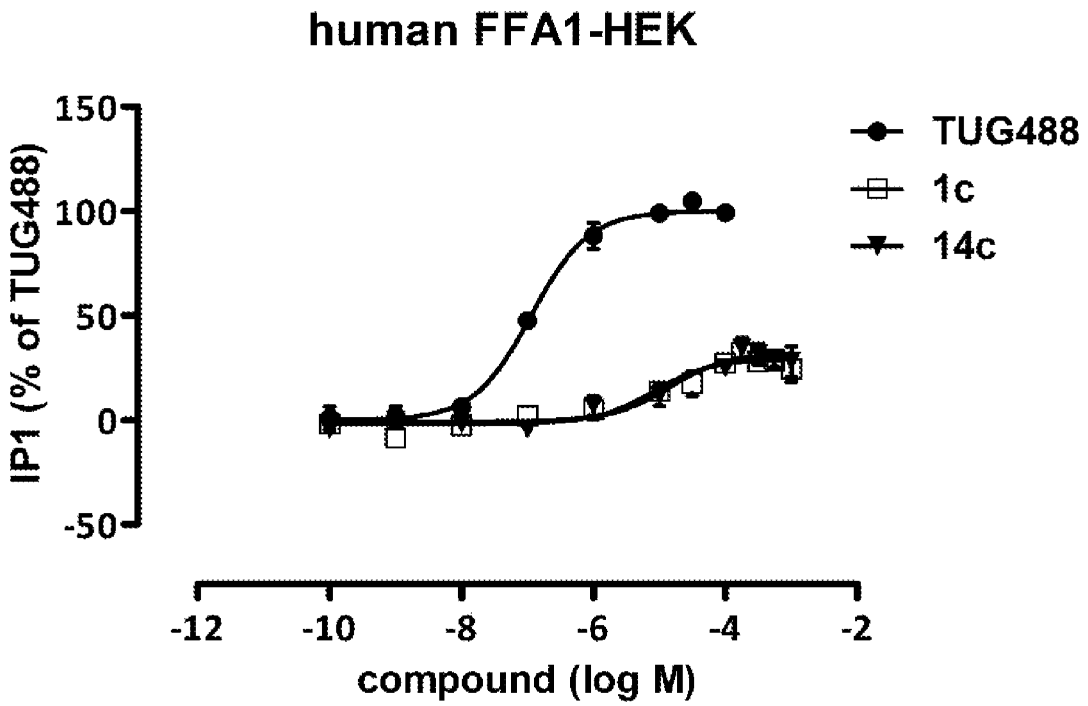
FIG. 14 shows effect of compound 1c & 14c on GSK40 (FFA1) by Inositolphosphate 1 (IP1) measurement. Human recombinant HEK293 cells stably expressing hFFA1 were stimulated with the indicated compounds and IP1 accumulation was quantified. TUG488 (Lit) was included as reference for robust FFA1 activation. pEC50: 1c: 5.08±0.22; 14c: 4.85±0.25. Shown are mean values±s.e.m. of three independent experiments.
Figure 15:
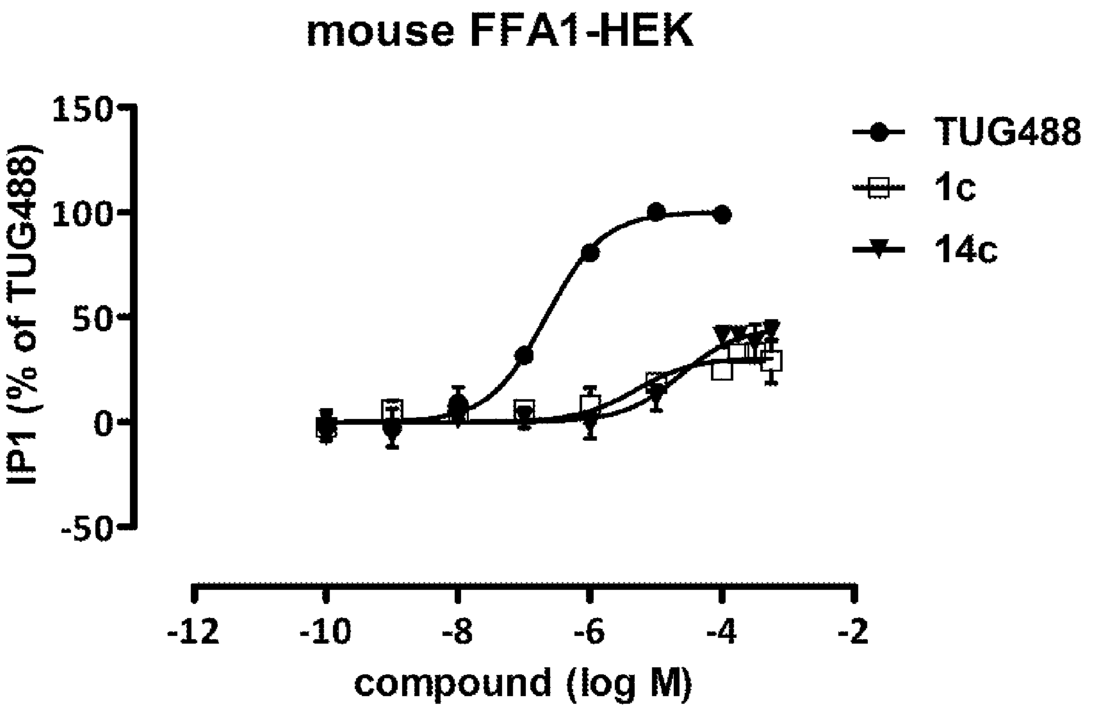
FIG. 15 shows effect of compound 1c & 14c on GSK40 (mFFA1) by Inositolphosphate 1 (IP1) measurement. Human recombinant HEK293 cells stably expressing the mouse ortholog of FFA1 (mFFA1) were stimulated with the indicated compounds and IP1 accumulation was quantified. TUG488[1] was included as reference for robust mFFA1 activation. $pEC_{50}$: 1c: 5.31±0.31; 14c: 4.63±0.23. Shown are mean values±s.e.m. of three independent experiments.
Figure 17:
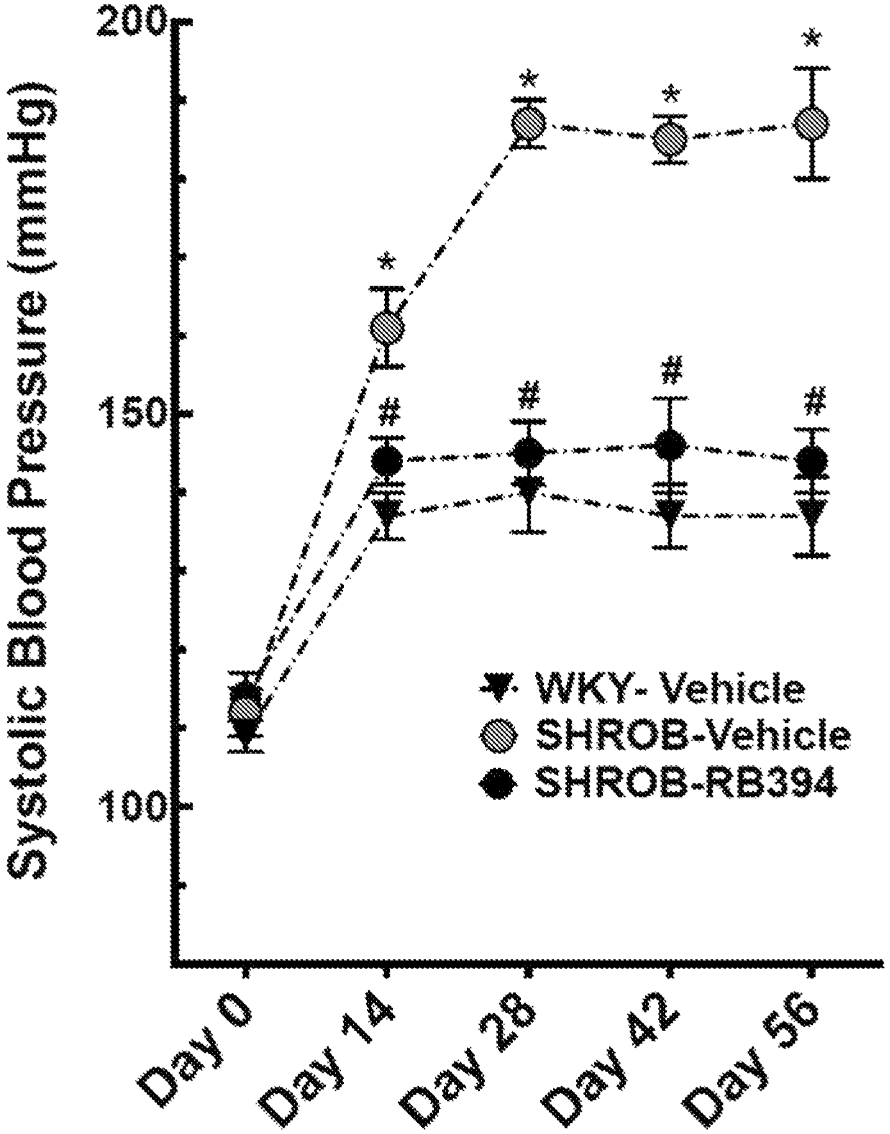
FIG. 17 illustrates systolic blood pressure data for RB394 in SHROB model.
Figure 18:
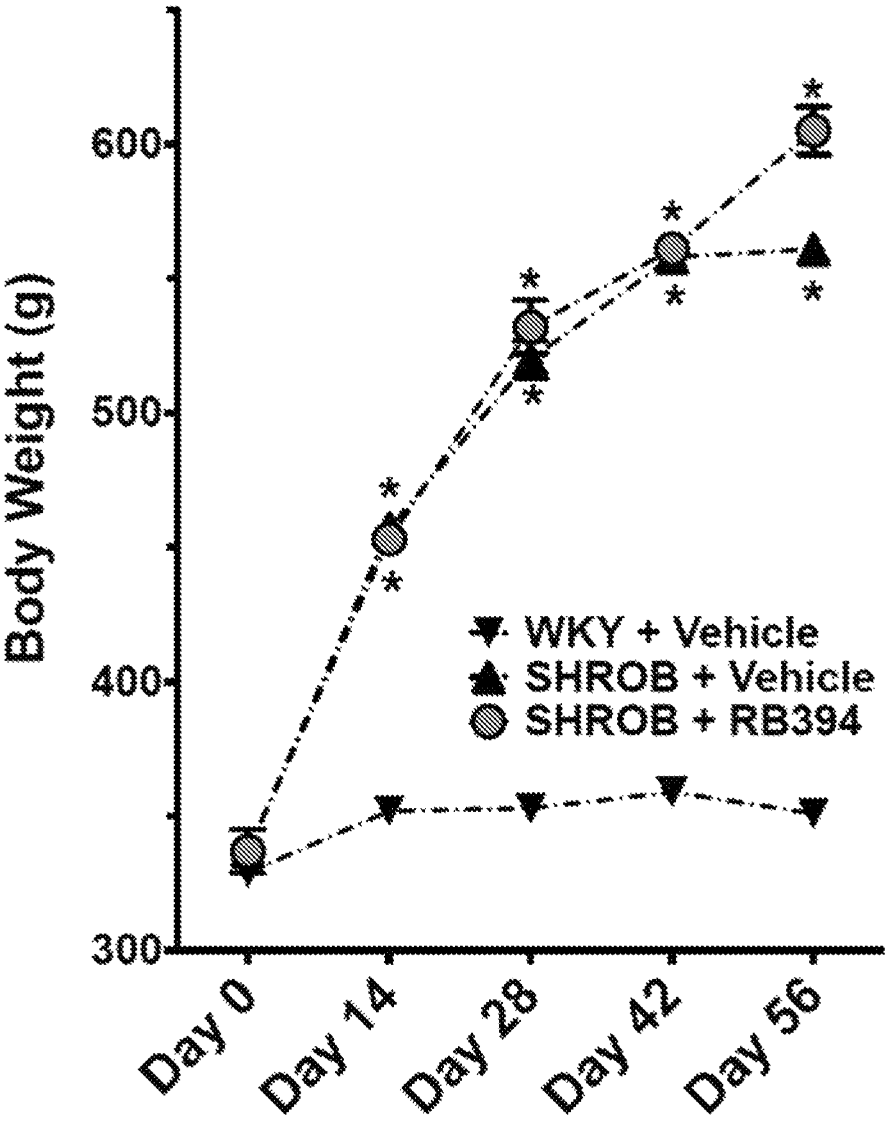
FIG. 18 illustrates body weight data for RB394 in the SHROB model.
Figure 19:
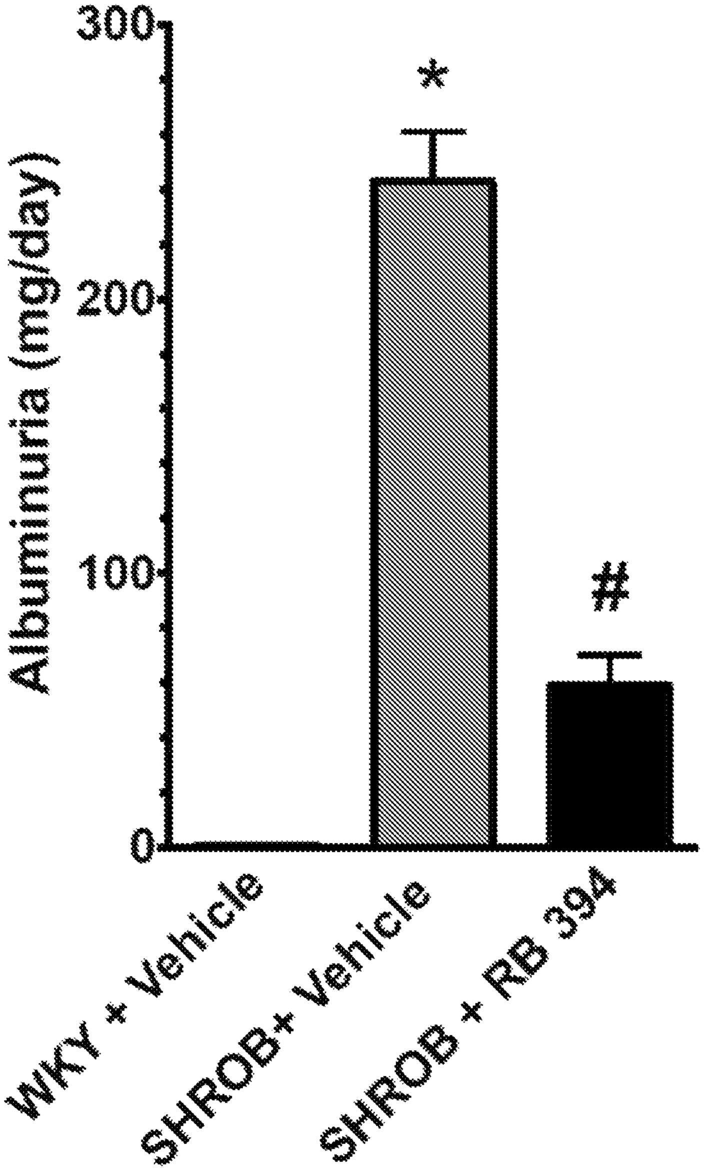
FIG. 19 illustrates albuminuria data for RB394 in the SHROB model.
Figure 20:
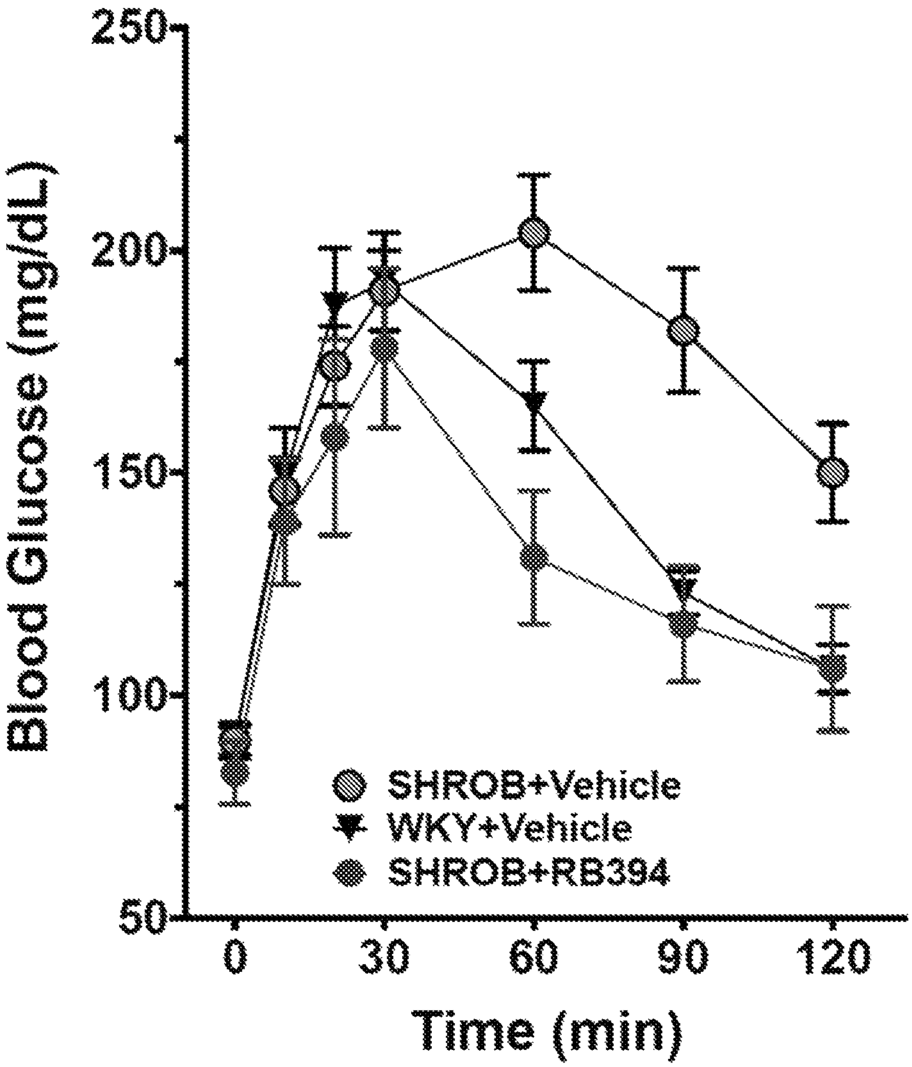
FIG. 20 illustrates blood glucose data for RB394 in the SHROB model.

We explored the SAR of α substituted benzylbenzamide propionic acid derivatives having in mind the application in an animal model of metabolic syndrome. Thus, two main optimization criteria have been identified. The first aim was the improvement of water solubility to fit a long term drinking water application. The significant difference in exposure from compound 1b to 1c (ester to acid derivative) underlines the importance of an enhanced water solubility for bioavailability[101]. The second aim was to achieve sufficient potency in a concentration range below the steady state concentration in plasma. The substitution at the α-position of the carboxyl function plays a key role in PPARγ activation, assuming the classical PPAR binding mode[86,91]. Based on that knowledge the first variations of the compound were modifications of the α-ethyl group. Neither the reduction to methyl or complete removal of the α-substituent nor the extension to propyl or phenyl substitution showed any major effects on PPARγ activation (Table 3). We interpret this SAR as another indication of the alternative binding mode. A general phenomenon concerning the a-d type derivatives, with the same substitution pattern, is the improvement in water solubility from ester to acid derivative. For compound 16a-d, 18a-d and 19a-d for example, the difference enfolds two orders of magnitude (Table 3). An α, β-cyclopropyl derivative was produced (22), with no enhanced potency on any target. The synthesis path yielded certain non-acidic pre-stages (21, 22; Table 1) which were evaluated on the two investigated targets. As expected they showed good inhibitory potency towards sEH in a double-digit nanomolar range. Surprisingly, compound 21 with a similar scaffold to the estimated compound 22, however lacking an acidic moiety, showed a slightly higher activation of PPARγ. This again leads to the assumption of a minor role of the acidic head group and the possible appearance of an alternative binding mode. The next variations were performed on the ortho position of the benzyl ring (2a-6c) (Table 4). The —$CF_3$ group was substituted by —H, —$CH_3$, —Cl, —Br and —$OCF_3$, which all lead to potency loss. Only the —$OCF_3$ ester derivative (6b) showed a marginal sEH inhibition improvement. With the absence of an ortho substitution sEH inhibition almost vanished and PPAR activity dropped for nearly one order of magnitude. This highlights the relevance of the ortho —$CF_3$ substitution. In the following 24 derivatives (7a-11c) (Table 4) the study focused on the para substitution of the benzyl moiety. With the introduction of a sterically demanding group (—$CF_3$, —$OCF_3$ and —O-phenyl) in the para position of the benzyl-ring the PPARγ subtype selectivity got lost and no major improvements on PPARγ were accomplished. The activation of the PPARγ subtype by introduction of larger moieties in the para benzyl-ring position on similar scaffold can also be found in literature, but mostly without effects on PPARγ activation[70]. Nevertheless, the para —O-phenyl acid derivative (12c) showed, as only compound from this study, activity on all PPAR subtypes. 12c also reached the highest PPARγ potency, with an $EC_{50}$ of 0.3 μM and a peak activation of 181% compared to pioglitazone. The sEH inhibition dropped virtually for one order of magnitude for all para substituted derivatives lacking an ortho substituent. 12c represents a good PPAR pan agonist, however it lacks appropriate sEH inhibitory potency. The use of smaller substituents at the benzyl para position (—F, —O—$CH_3$, —Cl) did not improve the potency on either one of the targets, but kept PPARγ subtype selectivity. In the next step ortho, para combined substitution pattern of the benzyl moiety was created (13a-14d) (Table 4). The impact of the benzyl-ring ortho —$CF_3$ substitution has already been explored. As para substitution partner in this combination —F and —O—$CH_3$ were chosen, referring to their subtype selective activation on PPARγ in the previously produced data. From the —O—$CH_3$ substituent an increase in water solubility was also assumed. The ortho —$CF_3$, para —F substitution pattern improved subtype-selective PPARγ activation, but had no enhancing effect on sEH inhibition. With compound 14c (ortho —$CF_3$, meta —O—$CH_3$) potency on both targets got improved by almost one order of magnitude (sEH $IC_{50}$=0.3 μM, PPARγ $EC_{50}$=0.3 μM/160%). Furthermore, compound 14c is equipotent on both targets and the water solubility increased from 100 μM to 500 μM in PBS buffer. 14c fulfills the requirements which motivated us to perform a second pharmacological profiling. Compound 14c did not impair cell viability of HepG2 cells up to a concentration of 30 μM, indicated by the WST-1 assay[92]. After 1 h incubation of 14c with Spargue-Dawley rat liver microsomes ~96% of the compound remained intact (see FIG. 13). In a 2 week in vivo pharmacokinetic study in 6 mice, with drinking water application of 14c (30 mg/kg bw), a final plasma concentration of 986±363 ng/ml (~3±1.1 μM) was achieved (FIG. 3*a*). qPCR analysis of the mouse livers after 2 weeks of treatment showed an upregulation of the PPARγ target gene CD36 (FIG. 3*b*). As the plasma concentration of 14c was one order of magnitude higher than both in vitro values and the PPARγ target gene expression was improved, the compound qualifies as a pharmacological tool for diabetic animal models.

TABLE 4

Inhibition and activation values of dual sEH/PPAR modulators with variations in benzyl-ring substition.

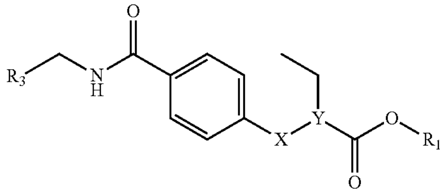

a) X-Y: CH═C; $R_1$: $CH_2CH_3$
b) X-Y: $CH_2$—CH; $R_1$: $CH_2CH_3$
c) X-Y: $CH_2$—CH; $R_1$: H
d) X-Y: CH═CH; $R_1$: H

| compd. | $R_3$ | w.s. [μM] | $IC_{50}$ sEH [μM] | $EC_{50}$ PPARα [μM] ($E_{max}$-%) | $EC_{50}$ PPARδ [μM] ($E_{max}$-%) | $EC_{50}$ PPARγ [μM] ($E_{max}$-%) |
|---|---|---|---|---|---|---|
| 2a | 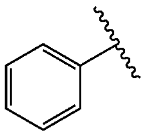 [SMILES: *c1ccccc1] | n.t. | n.t. | n.t. | n.t. | n.t. |
| 2b | | n.t. | 8.5 ± 2.9 | i.a. | i.a. | 16 ± 1.7 (94%) |
| 2c | | n.t. | @ 10 μM (4%) | i.a. | i.a. | 13.5 ± 2.0 (123%) |
| 2d | | n.t. | 9.3 ± 1.3 | n.t. | n.t. | n.t. |
| 3a | 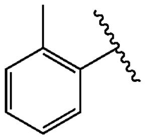 [SMILES: *c1ccccc1C] | n.t. | 0.760 ± 0.005 | n.t. | n.t. | n.t. |
| 3b | | n.t. | 0.9 ± 0.1 | @10 μM (15%) | i.a. | @ 10 μM (15%) |
| 3c | | n.t. | @ 10 μM (25%) | i.a. | i.a. | 4 ± 0.5 (106%) |
| 3d | | n.t. | 10 ± 0.7 | n.t. | n.t. | n.t. |
| 4a | 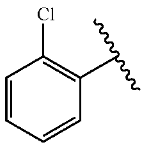 [SMILES: *c1ccccc1Cl] | n.t. | 0.41 ± 0.14 | n.t. | n.t. | n.t. |
| 4b | | n.t. | 3.8 ± 0.2 | i.a. | i.a. | @ 10 μM (14%) |
| 4c | | n.t. | @ 10 μM (20%) | i.a. | i.a. | @ 10 μM (40%) |
| 4d | | n.t. | 2.8 ± 0.4 | n.t. | n.t. | n.t. |
| 5a | 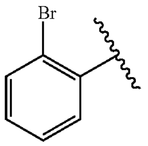 [SMILES: *c1ccccc1Br] | n.t. | 0.3 ± 0.08 | n.t. | n.t. | n.t. |
| 5b | | 25 | 4 ± 0.7 | i.a. | i.a. | i.a. |
| 5c | | 500 | @ 10 μM (34%) | i.a. | i.a. | @ 10 μM (40%) |
| 5d | | n.t. | 2.4 ± 0.2 | n.t. | n.t. | n.t. |
| 6a | 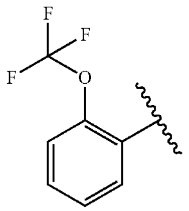 [SMILES: *c1ccccc1OC(F)(F)F] | 10 | 0.06 ± 0.013 | n.t. | n.t. | n.t. |
| 6b | | 100 | 0.03 ± 0.008 | i.a. | i.a. | 3.5 ± 0.6 (88%) |
| 6c | | 500 | @ 10 μM (23%) | i.a . | i.a. | 8 ± 1.3 (110%) |
| 6d | | n.t. | 0.9 ± 0.3 | n.t. | n.t. | n.t. |

TABLE 4-continued

Inhibition and activation values of dual sEH/PPAR modulators with variations in benzyl-ring substition.

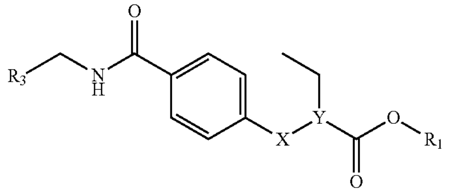

a) X-Y: CH═C; $R_1$: $CH_2CH_3$
b) X-Y: $CH_2$—CH; $R_1$: $CH_2CH_3$
c) X-Y: $CH_2$—CH; $R_1$: H
d) X-Y: CH═CH; $R_1$: H

| compd. | $R_3$ | w.s. [μM] | $IC_{50}$ sEH [μM] | $EC_{50}$ PPARα [μM] ($E_{max}$-%) | $EC_{50}$ PPARδ [μM] ($E_{max}$-%) | $EC_{50}$ PPARγ [μM] ($E_{max}$-%) |
|---|---|---|---|---|---|---|
| 7a | 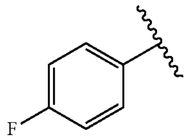 [SMILES: *c1ccc(F)cc1] | n.t. | 0.062 ± 0.003 | n.t. | n.t. | n.t. |
| 7b | | n.t. | 2.2 ± 0.2 | i.a. | i.a. | 11 ± 1.9 (74%) |
| 7c | | n.t. | @ 10 μM (28%) | i.a. | i.a. | @ 10 μM (23%) |
| 7d | | n.t. | 6.7 ± 0.9 | n.t. | n.t. | n.t. |
| 8a | 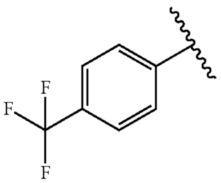 [SMILES: *c1ccc(C(F)(F)F)cc1] | n.t. | 0.55 ± 0.06 | n.t. | n.t. | n.t. |
| 8b | | n.t. | 0.57 ± 0.007 | @ 10 μM (22%) | i.a. | 4.2 ± 1.5 (76%) |
| 8c | | n.t. | 7.2 ± 0.7 | 7 ± 0.8 (89%) | i.a. | 6.3 ± 2.7 (192%) |
| 8d | | 500 | 2.8 ± 0.7 | n.t. | n.t. | n.t. |
| 9a | 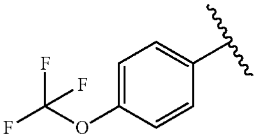 [SMILES: *c1ccc(OC(F)(F)F)cc1] | n.t. | 0.88 ± 0.1 | n.t. | n.t. | n.t. |
| 9b | | n.t. | 0.9 ± 0.42 | 3 ± 0.1 (58%) | i.a. | 3 ± 0.5 (68%) |
| 9c | | n.t. | 14 ± 2 | 2 ± 0.3 (89%) | i.a. | 2 ± 0.3 (125%) |
| 9d | | n.t. | 1.6 ± 0.1 | n.t. | n.t. | n.t. |
| 10a | 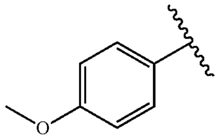 [SMILES: *c1ccc(OC)cc1] | 10 | 0.55 ± 0.04 | n.t. | n.t. | n.t. |
| 10b | | 10 | 0.62 ± 0.02 | i.a. | i.a. | @ 10 μM (40%) |
| 10c | | 500 | @ 10 μM (34%) | i.a. | i.a. | 7 ± 2 (110%) |
| 10d | | n.t. | 13 ± 2 | n.t. | n.t. | n.t. |
| 11a | 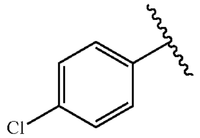 [SMILES: *c1ccc(Cl)cc1] | 10 | 3 ± 1.4 | n.t. | n.t. | n.t. |
| 11b | | 10 | 1.7 ± 0.1 | i.a. | i.a. | @ 10 μM (40%) |
| 11c | | 500 | 1.5 ± 0.2 | i.a. | i.a. | 4 ± 1 (171%) |
| 11d | | 100 | 5 ± 2 | n.t. | n.t. | n.t. |
| 12a | 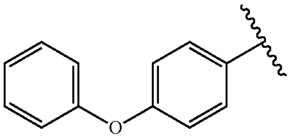 [SMILES: *c1ccc(Oc2ccccc2)cc1] | n.t. | 1.4 ± 0.06 | n.t. | n.t. | n.t. |
| 12b | | n.t. | n.t. | 4 ± 0.7 (110%) | i.a. | 1.4 ± 0.3 (141%) |
| 12c | | n.t. | 12 ± 1 | 0.9 ± 0.3 (106%) | @ 10 μM (20%) | 0.3 ± 0.08 (181%) |
| 12d | | n.t. | 0.8 ± 0.2 | n.t. | n.t. | n.t. |
| 13a | 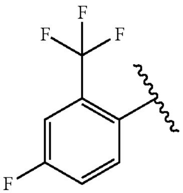 [SMILES: *c1ccc(F)cc1C(F)(F)F] | n.t. | 0.1 ± 0.01 | n.t. | n.t. | n.t. |
| 13b | | n.t. | 0.12 ± 0.07 | i.a. | i.a. | 2.8 ± 0.9 (118%) |
| 13c | | n.t. | 1.2 ± 0.2 | i.a. | i.a. | 0.6 ± 0.2 (158%) |
| 13d | | n.t. | 1.2 ± 0.02 | n.t. | n.t. | n.t. |

TABLE 4-continued

Inhibition and activation values of dual sEH/PPAR modulators with variations in benzyl-ring substition.

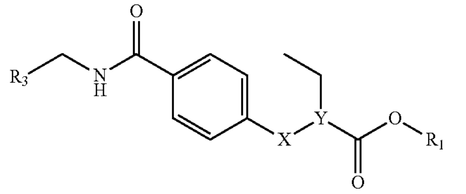

a) X-Y: CH═C; $R_1$: $CH_2CH_3$
b) X-Y: $CH_2$—CH; $R_1$: $CH_2CH_3$
c) X-Y: $CH_2$—CH; $R_1$: H
d) X-Y: CH═CH; $R_1$: H

Figure 4:
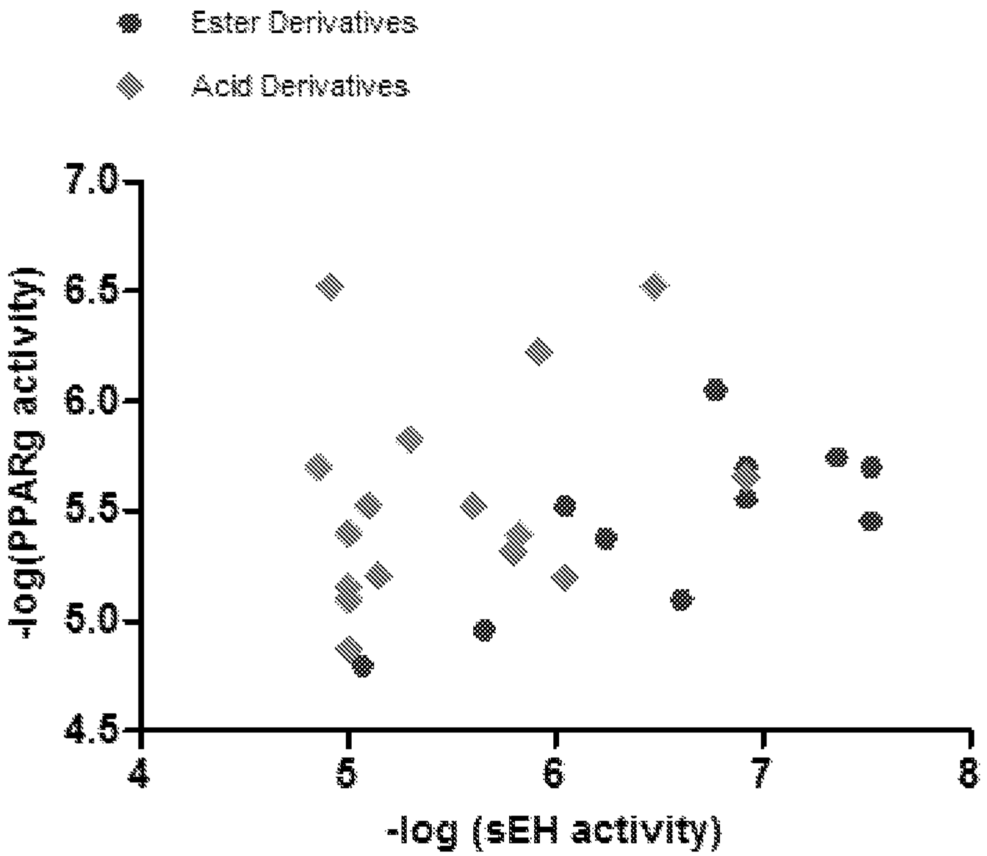
FIG. 4 shows a plot of sEH vs. PPARγ activity values.
Figure 5:
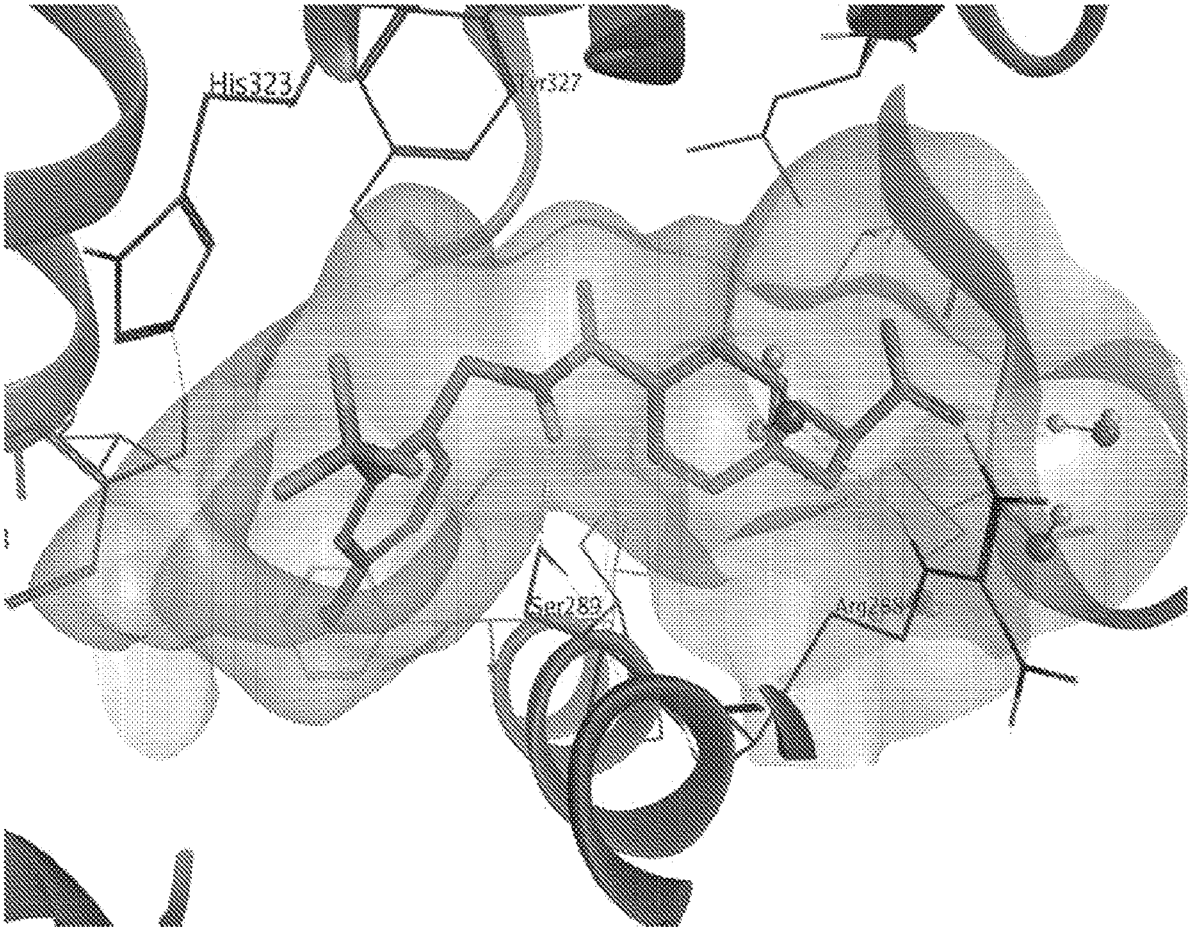
FIG. 5 shows the binding mode of compound 14c modelled by docking of compound into the X-ray structure of the PPARγ LBD co-crystallized with compound GSK1997132B.

| compd. | $R_3$ | w.s. [μM] | $IC_{50}$ sEH [μM] | $EC_{50}$ PPARα [μM] ($E_{max}$-%) | $EC_{50}$ PPARδ [μM] ($E_{max}$-%) | $EC_{50}$ PPARγ [μM] ($E_{max}$-%) |
|---|---|---|---|---|---|---|
| 14a | 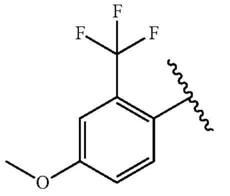 [SMILES: *c1ccc(OC)cc1C(F)(F)F] | n.t. | 0.05 ± 0.009 | n.t. | n.t. | n.t. |
| 14b | | n.t. | 0.03 ± 0.001 | @ 10 μM (22%) | i.a. | 2 ± 0.3 (136%) |
| 14c | | 500 | 0.33 ± 0.05 | @ 10 μM (29%) | i.a. | 0.3 ± 0.09 160%) |
| 14d | | n.t. | 0.4 ± 0.2 | n.t. | n.t. | n.t. |

i.a. = inactive,
n.t. not tested,
$E_{max}$-% = maximum activation in percent,
w.s. = water solubility,
compd. = compound i.a.=inactive, n.t. not tested, $E_{max}$-%=maximum activation in percent, w.s.=water solubility, compd.=compound Conclusion This study was able to create a series of well characterized sEH/PPARγ dual modulators. Along a hit (1c) to lead (14c) compound development, potency and PK/PD parameters were improved. Information about drug-target interaction properties for sEH and PPARγ has also been generated. The scatter plot (FIG. 4) displays an overview of the generated in vitro data, separating them in acid (red) and ester (blue) derivatives. A clear trend of improved sEH inhibition by ester derivatives can be recognized. This phenomenon fits the common knowledge about the character of the sEH binding-pocket[102-105]. The preferred placement of an acidic head group at the para position of a lipophilic linear shaped molecule (25) compared to a side-facing acidic head group (26) has also been shown before[106]. The importance of an ortho —$CF_3$ group, at the benzyl moiety, for sEH inhibition, at this particular type of scaffolds, has also been explored by GlaxoSmithKline[69]. In the case of PPARγ activity values, no clear preference of acid derivatives can be recognized. This fact is contradictory to the majority of published PPAR agonists, which commonly contain an acidic head group[86,89]. Comparing this work with the research done by KYORIN Pharmaceutical[70,87,107,108] a conspicuous difference in selectivity can be recognized, although the basic benzylbenzamide scaffold was employed in both studies. KYORIN Pharmaceuticals compounds are highly selective on PPARα, while the compounds of this study are nearly all PPARγ selective agonists. The introduction of steric demanding moieties in the para position of the benzyl-ring caused a shift in the direction of an activity profile more analogical to KYORIN Pharmaceuticals data. It was shown that the space for structural variations to fulfill the desired aims of this project is very tight. FIG. 5 visualizes a possible alternative PPARγ ligand binding mode of compound 14c, produced by a docking study, based on a co-crystallized benzylbenzamide derivative (PDB: 3S9S) by GlaxoSmithKline[68]. In this scenario the benzylbenzamide structure could be responsible for the PPAR activation.

The assumed binding mode qualifies benzylbenzamide as a merged pharmacophore of both investigated targets. However, the only proof of this postulate would be a PPARγ co-crystallized compound from this study. Driven by structural similarities the impact of compound 1c and 14c on free fatty acid receptor 1 (FFA1, formerly GPR40) activation was determined. FFA1 or GPR40 is a receptor relevant for pancreatic β-cell insulin secretion. The partial agonistic effect, shown in supporting information (see 14 and 15), is assumed to be secondary in the pathogenic interference. Nevertheless, a pharmacological tool compound 14c with interesting features for the investigation of the metabolic syndrome has been produced. There are high expectations on the sEH/PPAR combinational therapy of diabetes mellitus type 2. Imig et al. has already shown that the combined application of rosiglitazone (PPARγ agonist) and t-AUCB (sEH inhibitor) produce a positive synergistic effect on kidney injury in spontaneous hypertensive obese (SHROB) rats[66]. One of the major consequences of diabetes mellitus type 2 is kidney injury, resulting in diabetic nephropathy. The clinical effectiveness of sEH/PPAR dual therapy for diabetic nephropathy still has to be shown. Two thirds of the patients suffering from diabetes type 2 develop neuropathic pain. Hammock et al. explored the capability of sEH inhibitors to reduce neuropathic pain in diabetic in vivo models[55-57]. One of the shortcomings of certain single PPARγ agonists, especially TZDs, is the frequently observed sodium and water retention. This effect can be dangerous to patients with congestive heart failure[109,110] sEH and EETs are natriuretic and auxiliary to maintain fluid and electrolyte homeostasis[64,65]. Inferentially, the combination of a PPARγ agonist with a sEH inhibitor might overcome existing side effects by keeping the beneficial features as well as extending them with new ones. Furthermore, the dual-ligand approach represents a huge benefit by simplifying the pharmacokinetics compared to a two drug combination therapy[111]. Complex pharmacokinetics of drug combinations should not be underestimated, unpredictable drug-drug interactions can occur and side effects add up. Overall 80 synthesized derivatives confirmed the knowledge about the sEH binding-pocket character and brought a controversal light into the common view of the PPARγ ligand-binding situation. The focus on two moieties of the original scaffold was enough to improve potency as well as ADME values to qualify compounds for long-term in vivo experiments.

EXPERIMENTAL SECTION

Chemistry

General.

All educts, regencies and solvents were purchases from the companies Alfa-Aesar GmbH & Co KG (Karlsruhe, Germany), Sigma-Aldrich Chemie GmbH (Hannover, Germany), Apollo Scientific Ltd (Manchester, England), JRD Fluorochemicals, Ltd. (Surrey, England) and used without further purification. The companies guaranteed purity above 97%. TLC was performed by silica coated aluminum foil (particle size 60 μm) purchased from Merk KGaA (Darmstadt, Germany). For purification of synthesized compounds an Intelli Flash 310 Chromatograph by the firm Varian Medical Systems Deutschland GmbH (Darmstadt, Germany). Two kinds of packed columns have been used: SF25-80g & SF25-60g, both loaded with silica gel (particle size 50 μm) and also purchased from firm Varian Medical Systems Deutschland GmbH (Darmstadt, Germany). $^1H$ (250/400 MHz) & $^{13}C$ (64 MHz) were measured on DPX250 and AV400 nuclear magnetic resonance spectrometer from Burker (Karlsruhe, Germany). All spectra were analyzed with the program TopSpin as well from Burker (Karlsruhe, Germany). Tetramethylsilane was used as internal standard. DMSO-$d_6$ and Methanol-$d_3$ were used as solvents. HPLC and mass analyses were performed by a LCMS 2020 from Shimadzu (Duisburg, Germany), under the use of a MultoHigh 100 RP 18, 3μ, 100×2 mm column from CS Chromatography-Service GmbH (Langerwehe, Germany). Eluation was maintained by an acetonitrile/water gradient from 20-75%. The electron spray ionization produced positive (+) as well as negative (−) spectra and the UV chromatogram measured two wavelengths (λ=254 and 280 nm). High resolution mass spectroscopy was performed by a Thermo Scientific MALDI LTQ ORBITRAP XL. All final compounds had a purity ≥95% as determined by HPLC.

General Procedure for the Preparation of the Compounds 1-17, Using the Example of 4-formyl-N-(2-(trifluoromethyl) benzyl)benzamide (1).

1 g (6.7 mmol) 4-formylbenzoic acid, 0.9 ml (6.7 mmol) triethylamine and 1 ml (7.3 mmol) isobutylchlorformiat were solved in 30 ml chloroform at 0° C. under an argon atmosphere. After 1 h 0.9 ml (6.7 mmol) 2 (trifluoromethyl) benzylamine was added. The solution was allowed to warm to room temperature and stirred for 12 h. The reaction mixture was washed three times with each 20 ml of 2 M HCl solution, 20 ml of 1 M NaOH solution and one time with 20 ml of brine. The organic layer was dried over $MgSO_4$ and the solvent was removed under reduced pressure. The crude product was recrystallized from an EE/Hex mixture. A white solid remained. Yield: 1.43 g (70%); $^1H$ NMR (DMSO-$d_6$): δ 10.17 (s, 1H, $Ph_1$-CHO), 9.38 (t, J=5.9 Hz, 1H, $Ph_1$-OCNH), 9.08-8.19 (m, 4H, CHO-$Ph_1$), 7.83-7.52 (m, 4H, OCNH—$CH_2$-$Ph_2$), 4.75 (d, J=5.6 Hz, 2H, $Ph_1$-OCNH—$CH_2$) ppm. MS-ESI: m/z 342 [M+Cl$^-$].

4-Formyl-N-(benzyl)benzamide (2)

Yield: 0.99 g (68%); $^1H$ NMR (DMSO-$d_6$): δ 10.1 (s, 1H, $Ph_1$-CHO), 9.27 (t, J=5.9 Hz, 1H, $Ph_1$-OCNH), 8.11-7.99 (m, 4H, CHO-$Ph_1$), 7.37-7.23 (m, 4H, OCNH—$CH_2$-$Ph_2$), 4.52 (d, J=5.8 Hz, 2H, $Ph_1$-OCNH—$CH_2$) ppm. MS-ESI: m/z 240 [M+H$^+$].

4-Formyl-N-(2-(methyl)benzyl)benzamide (3)

Yield: 1 g (65%); $^1H$ NMR (DMSO-$d_6$): δ 10.1 (s, 1H, $Ph_1$-CHO), 9.14 (t, J=5.4 Hz, 1H, $Ph_1$-OCNH), 8.13-7.99 (m, 4H, CHO-$Ph_1$), 7.31-7.14 (m, 4H, OCNH—$CH_2$-$Ph_2$), 4.49 (d, J=5.6 Hz, 2H, $Ph_1$-OCNH—$CH_2$), 2.34 (s, 3H, $Ph_2$-$CH_3$) ppm. MS-ESI: m/z 254 [M+H$^+$].

4-Formyl-N-(2-(chloro)benzyl)benzamide (4)

Yield: 1.16 g (70%); $^1H$ NMR (DMSO-$d_6$): δ 10.14 (s, 1H, $Ph_1$-CHO), 9.28 (t, J=6 Hz, 1H, $Ph_1$-OCNH), 8.13-8.02 (m, 4H, CHO-$Ph_1$), 7.5-7.28 (m, 4H, OCNH—$CH_2$-$Ph_2$), 4.58 (d, J=5.8 Hz, 2H, $Ph_1$-OCNH—$CH_2$) ppm. MS-ESI: m/z 274 [M+H$^+$].

4-Formyl-N-(2-(bromo)benzyl)benzamide (5)

Yield: 1.33 g (69%); $^1H$ NMR (DMSO-$d_6$): δ 10.11 (s, 1H, $Ph_1$-CHO), 9.29 (t, J=5.6 Hz, 1H, $Ph_1$-OCNH), 8.14-8.01 (m, 4H, CHO-$Ph_1$), 7.67-7.02 (m, 4H, OCNH—$CH_2$-$Ph_2$), 4.55 (d, J=5.8 Hz, 2H, $Ph_1$-OCNH—$CH_2$) ppm. MS-ESI: m/z 319 [M+H$^+$].

4-Formyl-N-(2-(trifluoromethoxy)benzyl)benzamide (6)

Yield: 1.18 g (70%); $^1H$ NMR (DMSO-$d_6$): δ 10.11 (s, 1H, $Ph_1$-CHO), 9.27 (t, J=5.7 Hz, 1H, $Ph_1$-OCNH), 8.11-8.02 (m, 4H, CHO-$Ph_1$), 7.51-7.37 (m, 4H, OCNH—$CH_2$-$Ph_2$), 4.59 (d, J=5.7 Hz, 2H, $Ph_1$-OCNH—$CH_2$) ppm. MS-ESI: m/z 324 [M+H$^+$].

4-Formyl-N-(4-fluorobenzyl)benzamide (7)

Yield: 0.97 g (70%); $^1H$ NMR (DMSO-$d_6$): δ 10.15 (s, 1H, $Ph_1$-CHO), 9.33 (t, J=5.7 Hz, 1H, $Ph_1$-OCNH), 8.16-8.04 (m, 4H, CHO-$Ph_1$), 7.47-7.18 (m, 4H, OCNH—$CH_2$-$Ph_2$), 4.54 (d, J=5.9 Hz, 2H, $Ph_1$-OCNH—$CH_2$) ppm. MS-ESI: m/z 258 [M+H$^+$].

4-Formyl-N-(4-(trifluoromethyl)benzyl)benzamide (8)

Yield: 1.3 g (70%); $^1H$ NMR (DMSO-$d_6$): δ 10.1 (s, 1H, $Ph_1$-CHO), 9.37 (t, J=5.9 Hz, 1H, $Ph_1$-OCNH), 8.12-8 (m, 4H, CHO-$Ph_1$), 7.74-7.54 (m, 4H, OCNH—$CH_2$-$Ph_2$), 4.6 (d, J=5.8 Hz, 2H, $Ph_1$-OCNH—$CH_2$) ppm. MS-ESI: m/z 308 [M+H$^+$].

4-Formyl-N-(4-(trifluoromethoxy)benzyl)benzamide (9)

Yield: 1.37 g (70%); $^1H$ NMR (DMSO-$d_6$): δ 10.15 (s, 1H, $Ph_1$-CHO), 9.36 (t, J=6 Hz, 1H, $Ph_1$-OCNH), 8.18-8.04

(m, 4H, CHO-$Ph_1$), 7.55-7.36 (m, 4H, OCNH—$CH_2$-$Ph_2$), 4.58 (d, J=6 Hz, 2H, $Ph_1$-OCNH—$CH_2$) ppm. MS-ESI: m/z 324 [$M+H^+$].

4-Formyl-N-(4-(methoxy)benzyl)benzamide (10)

Yield: 1.3 g (70%); $^1$H NMR (DMSO-$d_6$): δ 10.14 (s, 1H, $Ph_1$-CHO), 9.24 (t, J=5.5 Hz, 1H, $Ph_1$-OCNH), 8.15-8.03 (m, 4H, CHO-$Ph_1$), 7.34-6.93 (m, 4H, OCNH—$CH_2$-$Ph_2$), 4.49 (d, J=5.9 Hz, 2H, $Ph_1$-OCNH—$CH_2$) ppm. MS-ESI: m/z 270 [$M+H^+$].

4-Formyl-N-(4-chlorobenzyl)benzamide (11)

Yield: 1.14 g (69%); $^1$H NMR (DMSO-$d_6$): δ 10.1 (s, 1H, $Ph_1$-CHO), 9.3 (t, J=6.4 Hz, 1H, $Ph_1$-OCNH), 8.1-8.01 (m, 4H, CHO-$Ph_1$), 7.43-7.35 (m, 4H, OCNH—$CH_2$-$Ph_2$), 4.5 (d, J=6 Hz, 2H, $Ph_1$-OCNH—$CH_2$) ppm. MS-ESI: m/z 274 [$M+H^+$].

4-Formyl-N-4-(phenoxybenzyl)benzamide (12)

Yield: 1.39 g (69%); $^1$H NMR (DMSO-$d_6$): δ 10.1 (s, 1H, $Ph_1$-CHO), 9.26 (t, J=5.9 Hz, 1H, $Ph_1$-OCNH), 8.17-7.99 (m, 4H, CHO-$Ph_1$), 7.42-6.96 (m, 9H, OCNH—$CH_2$-$Ph_2$+$Ph_2$-O-$Ph_3$), 4.5 (d, J=6 Hz, 2H, $Ph_1$-OCNH—$CH_2$) ppm. MS-ESI: m/z 332 [$M+H^+$].

4-Formyl-N-(4-fluoro-2-(trifluoromethyl)benzyl) benzamide (13)

Yield: 1.37 g (67%); $^1$H NMR (DMSO-$d_6$): δ 10.11 (s, 1H, $Ph_1$-CHO), 9.34 (t, J=5.5 Hz, 1H, $Ph_1$-OCNH), 8.17-8.01 (m, 4H, CHO-$Ph_1$), 7.68-7.51 (m, 3H, OCNH—$CH_2$-$Ph_2$), 4.66 (d, J=5.5 Hz, 2H, $Ph_1$-OCNH—$CH_2$) ppm. MS-ESI: m/z 326 [$M+H^+$].

4-Formyl-N-(4-methoxy-2-(trifluoromethyl)benzyl) benzamide (14)

Yield: 1.41 g (70%); $^1$H NMR (DMSO-$d_6$): δ 10.09 (s, 1H, $Ph_1$-CHO), 9.23 (t, J=5.9 Hz, 1H, $Ph_1$-OCNH), 8.1-8 (m, 4H, CHO-$Ph_1$), 7.48 (d, J=9.5 Hz, 1H, OCNH—$CH_2$-$Ph_2$-3H), 7.26-7.2 (m, 2H, OCNH—$CH_2$-$Ph_2$-2,5H), 4.6 (d, J=5.7 Hz, 2H, $Ph_1$-OCNH—$CH_2$), 3.81 (s, 1H, $CH_2$-$Ph_2$-4-$OCH_3$) ppm. MS-ESI: m/z 338 [$M+H^+$].

3-Formyl-N-(2-(trifluoromethyl)benzyl)benzamide (15)

Yield: 1.38 g (70%); $^1$H NMR (DMSO-$d_6$): δ 10.11 (s, 1H, $Ph_1$-CHO), 9.36 (t, J=5.9 Hz, 1H, $Ph_1$-OCNH), 8.27-8.1 (m, 4H, CHO-$Ph_1$), 7.79-7.46 (m, 4H, OCNH—$CH_2$-$Ph_2$), 4.71 (d, J=5.8 Hz, 2H, $Ph_1$-OCNH—$CH_2$) ppm. MS-ESI: m/z 308 [$M+H^+$].

General Procedure for the Preparation of the Compounds 24 & 27, Using the Example of 4-Iodo-N-(2-(trifluoromethyl)benzyl)benzamide (24)

1 g (6.7 mmol) 4-iodobenzoic acid, 1.5 g (8 mmol) EDC and 0.16 g (1.3 mmol) DMAP were mixed under argon atmosphere in 25 ml dry DCM and stirred as a suspension for 1 h at 0° C. Then 0.9 g (7.3 mmol) 2-trifluoromethylbenzylamin was added in one portion. The mixture was allowed to warm to room temperature and was further stirred for 24 h. The organic solution was washed twice with 20 ml 2 M HCl-solution and one time with 20 ml brine. The organic solvent was dried over $MgSO_4$ and then removed under reduced pressure. The crude product was recrystallized from a EE/Hex mixture and a white solid remained. Yield: 0.89 g (64%); $^1$H NMR (DMSO-$d_6$): δ 9.38 (t, J=6.3 Hz, 1H, $Ph_1$-OCNH), 8.11-8 (m, 4H, CHO-$Ph_1$), 7.79-7.48 (m, 4H, OCNH—$CH_2$-$Ph_2$), 4.7 (d, J=5.7 Hz, 2H, $Ph_1$-OCNH—$CH_2$) ppm. MS-ESI: m/z 405 [$M+H^+$].

4-Cyano-N-(2-(trifluoromethyl)benzyl)benzamide (27)

Yield: 0.92 g (65%); $^1$H NMR (DMSO-$d_6$): δ 9.38 (t, J=6.3 Hz, 1H, $Ph_1$-OCNH), 8.11-8 (m, 4H, CHO-$Ph_1$), 7.79-7.48 (m, 4H, OCNH—$CH_2$-$Ph_2$), 4.7 (d, J=5.7 Hz, 2H, $Ph_1$-OCNH—$CH_2$) ppm. MS-ESI: m/z 305 [$M+H^+$].

General Procedure for the Preparation of the Compounds (1a-19a), Using the Example of ethyl (E)-4-[N-((2-(trifluoromethyl)benzyl)benzamide]-alpha-ethylcinnamate (1a)

To a solution of 156 mg (6.5 mmol) NaH in 5 ml dry THF under an argon atmosphere at 0° C. was added slowly 1.2 ml (4.9 mmol) triethyl 2-phosphonobutyrat. After 30 min a solution of 1 g (3.3 mmol) of 4-formyl-N-(2-(trifluoromethyl)benzyl)benzamide (1) in 10 ml dry THF was added to the reaction mixture and stirred for 2 h. To quench the reaction 25 ml water were used. The resulting mixture was diluted with 10 ml EE. The organic layer was washed three times with brine and dried over $MgSO_3$. The solvent was evaporated under reduced pressure. After recrystallization from EE/Hex a white solid remained. Yield: 0.92 g (70%); $^1$H NMR (DMSO-$d_6$): δ 9.25 (t, J=5.8 Hz, 1H, $Ph_2$-OCNH), 8.09-7.38 (m, 8H, OCNH-$Ph_1$+$Ph_1$-OCNH—$CH_2$-$Ph_2$), 7.67 (s, 1H, OCNH-$Ph_1$-CH), 4.74 (d, J=5.4 Hz, 2H, $Ph_1$-OCNH—$CH_2$), 4.3 (q, J=7.1 Hz, 2H, C—COO—$CH_2$), 2.4 (q, J=6.9 Hz, 2H, CH—C—$CH_2$), 1.36 (t, J=7.06 Hz, 3H, COO—$CH_2$—$CH_3$), 1.18 (t, J=7.38 Hz, 3H, C—$CH_2$—$CH_3$) ppm; $^{13}$C-NMR (DMSO-$d_6$): $^{13}$C-NMR (DMSO-$d_6$): 169.4, 167.3, 136.9, 136.5, 136.3, 135.8, 135.7, 131.5, 129.4, 128.8, 128.4, 127.3, 126.3, 125.1, 125, 124.9, 124.1, 60.5, 40.2, 23.7, 13.3, 10 ppm; HRMS: measured m/z 405.1550 (theoretical: 405.1551).

Ethyl (E)-4-[N-benzylbenzamide]-alpha-ethylcinnamate (2a)

Yield: 0.92 g (65%); $^1$H NMR (DMSO-$d_6$): δ 9.12 (t, J=6.1 Hz, 1H, $Ph_2$-OCNH), 7.98-7.21 (m, 9H, OCNH-$Ph_1$+$Ph_1$-OCNH—$CH_2$-$Ph_2$), 7.33 (s, 1H, OCNH-$Ph_1$-CH), 4.5 (d, J=5.7 Hz, 2H, $Ph_1$-OCNH—$CH_2$), 4.23 (q, J=7 Hz, 2H, C—COO—$CH_2$), 2.41 (q, J=7 Hz, 2H, CH—C—$CH_2$), 1.3 (t, J=7.8 Hz, 3H, COO—$CH_2$—$CH_3$), 1.12 (t, J=7.3 Hz, 3H, C—$CH_2$—$CH_3$) ppm; $^{13}$C-NMR (DMSO-$d_6$): 167.5, 165.7, 137.9, 137.5, 137.1, 136.1, 135.9, 131.5, 129, 128.3, 127.5, 127.4, 126.7, 125.6, 125.5, 124.4, 61.7, 39.8, 24.9, 14.2, 10.5 ppm; HRMS: measured m/z 338.1752 (theoretical: 338.1750).

Ethyl (E)-4-[N-((2-methyl)benzyl)benzamide]-alpha-ethylcinnamate (3a)

Yield: 0.9 g (66%); $^1$H NMR (DMSO-$d_6$): δ 9.1 (t, J=6 Hz, 1H, $Ph_2$-OCNH), 7.7-7.21 (m, 8H, OCNH-$Ph_1$+$Ph_1$-OCNH—$CH_2$-$Ph_2$), 7.2 (s, 1H, OCNH-$Ph_1$-CH), 4.3 (d, J=5.7 Hz, 2H, $Ph_1$-OCNH—$CH_2$), 4.18 (q, J=6.9 Hz, 2H, C—COO—$CH_2$), 2.39 (q, J=6.8 Hz, 2H, CH—C—$CH_2$), 2.41 (s, 3H, $Ph_2$-$CH_3$), 1.25 (t, J=7.7 Hz, 3H, COO—$CH_2$—$CH_3$), 1.1 (t, J=7.2 Hz, 3H, C—$CH_2$—$CH_3$) ppm; $^{13}$C-NMR (DMSO-$d_6$): 167.4, 165.3, 136.8, 136.3, 136.1, 136, 135.9, 132.5, 129, 128.4, 128.5, 127.4, 126.5, 125.8, 125.3, 124.1, 60.7, 40.1, 23.9, 18.7, 13.2, 10.1 ppm; HRMS: measured m/z 352.1907 (theoretical: 352.1907).

Ethyl (E)-4-[N-((2-chloro)benzyl)benzamide]-alpha-ethylcinnamate (4a)

Yield: 0.87 g (64%); $^1$H NMR (DMSO-$d_6$): δ 9.15 (t, J=5.8 Hz, 1H, $Ph_2$-OCNH), 8.02-7.27 (m, 8H, OCNH-$Ph_1$+$Ph_1$-OCNH—$CH_2$-$Ph_2$), 7.4 (s, 1H, OCNH-$Ph_1$-CH), 4.57 (d, J=5.7 Hz, 2H, $Ph_1$-OCNH—$CH_2$), 4.24 (q, J=7.2 Hz, 2H, C—COO—$CH_2$), 2.38 (q, J=6.9 Hz, 2H, CH—C—$CH_2$), 1.3 (t, J=7.5 Hz, 3H, COO—$CH_2$—$CH_3$), 1.11 (t, J=6.7 Hz, 3H, C—$CH_2$—$CH_3$) ppm; $^{13}$C-NMR (DMSO-$d_6$): 167.3, 165.1, 138.1, 137.4, 137.2, 135.8, 135.7, 132.2, 129.3, 128.1, 127.4, 127.3, 126.5, 125.6, 125.2, 123.9, 60.5, 39.6, 24.7, 14.1, 10 ppm; HRMS: measured m/z 372.1363 (theoretical: 372.1361).

Ethyl (E)-4-[N-((2-bromo)benzyl)benzamide]-alpha-ethylcinnamate (5a)

Yield: 0.85 g (65%); $^1$H NMR (DMSO-$d_6$): δ 9.19 (t, J=5.8 Hz, 1H, $Ph_2$-OCNH), 8.06-7.23 (m, 8H, OCNH-$Ph_1$+$Ph_1$-OCNH—$CH_2$-$Ph_2$), 7.2 (s, 1H, OCNH-$Ph_1$-CH), 4.58 (d, J=5.6 Hz, 2H, $Ph_1$-OCNH—$CH_2$), 4.29 (q, J=7.3 Hz, 2H, C—COO—$CH_2$), 2.37 (q, J=7 Hz, 2H, CH—C—$CH_2$), 1.35 (t, J=6.8 Hz, 3H, COO—$CH_2$—$CH_3$), 1.17 (t, J=5.4 Hz, 3H, C—$CH_2$—$CH_3$) ppm; $^{13}$C-NMR (DMSO-$d_6$): 168.3, 166.1, 137.8, 137.4, 137.1, 135.7, 135.5, 132.1, 129.5, 128.2, 127.5, 127.2, 126.3, 125.8, 125.3, 122.9, 61.5, 40.6, 25.7, 14.4, 10.5 ppm; HRMS: measured m/z 416.0855 (theoretical: 416.0856).

Ethyl (E)-4-[N-((2-trifluoromethoxy)benzyl)benzamide]-alpha-ethylcinnamate (6a)

Yield: 0.86 g (66%); $^1$H NMR (DMSO-$d_6$): δ 9.1 (t, J=5.8 Hz, 1H, $Ph_2$-OCNH), 7.96-7.33 (m, 8H, OCNH-$Ph_1$+$Ph_1$-OCNH—$CH_2$-$Ph_2$), 7.4 (s, 1H, OCNH-$Ph_1$-CH), 4.69 (d, J=5.5 Hz, 2H, $Ph_1$-OCNH—$CH_2$), 4.3 (q, J=7.2 Hz, 2H, C—COO—$CH_2$), 2.57 (q, J=7.5 Hz, 2H, CH—C—$CH_2$), 1.37 (t, J=7 Hz, 3H, COO—$CH_2$—$CH_3$), 1.18 (t, J=7.6 Hz, 3H, C—$CH_2$—$CH_3$) ppm; $^{13}$C-NMR (DMSO-$d_6$): 173.3, 168.5, 167.1, 138.8, 138.4, 137.1, 136.7, 135.4, 132.2, 129.2, 128.4, 127.4, 127.3, 125.3, 125.1, 124.1, 123.1, 60.5, 42.6, 24.7, 14.7, 10.1 ppm; HRMS: measured m/z 421.1501 (theoretical: 421.1503).

Ethyl (E)-4-[N-((4-fluoro)benzyl)benzamide]-alpha-ethylcinnamate (7a)

Yield: 0.93 g (67%); $^1$H NMR (DMSO-$d_6$): δ 9.18 (t, J=6 Hz, 1H, $Ph_2$-OCNH), 8.02-7.18 (m, 8H, OCNH-$Ph_1$+$Ph_1$-OCNH—$CH_2$-$Ph_2$), 7.66 (s, 1H, OCNH-$Ph_1$-CH), 4.53 (d, J=6.1 Hz, 2H, $Ph_1$-OCNH—$CH_2$), 4.28 (q, J=7 Hz, 2H, C—COO—$CH_2$), 2.54 (q, J=7.9 Hz, 2H, CH—C—$CH_2$), 1.34 (t, J=7.11 Hz, 3H, COO—$CH_2$—$CH_3$), 1.18 (t, J=7.6 Hz, 3H, C—$CH_2$—$CH_3$) ppm; $^{13}$C-NMR (DMSO-$d_6$): 167.5, 167.2, 161.8, 139.7, 138.3, 138.1, 133.4, 131.2, 128.2, 128.1, 127.2, 127, 126.1, 125.1, 124.5, 118.9, 61.5, 42.6, 16.7, 14.6, 14.1 ppm; HRMS: measured m/z 356.1657 (theoretical: 356.1657).

Ethyl (E)-4-[N-((4-trifluoromethyl)benzyl)benzamide]-alpha-ethylcinnamate (8a)

Yield: 0.92 g (65%); $^1$H NMR (DMSO-$d_6$): δ 9.23 (t, J=6.5 Hz, 1H, $Ph_2$-OCNH), 7.99-7.53 (m, 8H, OCNH-$Ph_1$+$Ph_1$-OCNH—$CH_2$-$Ph_2$), 7.62 (s, 1H, OCNH-$Ph_1$-CH), 4.59 (d, J=6.3 Hz, 2H, $Ph_1$-OCNH—$CH_2$), 4.24 (q, J=7.4 Hz, 2H, C—COO—$CH_2$), 2.5 (q, J=7.9 Hz, 2H, CH—C—$CH_2$), 1.3 (t, J=7.4 Hz, 3H, COO—$CH_2$—$CH_3$), 1.12 (t, J=7.6 Hz, 3H, C—$CH_2$—$CH_3$) ppm; $^{13}$C-NMR (DMSO-$d_6$): 167.4, 167, 164.8, 139.3, 137.1, 136.7, 131.3, 132.4, 130.2, 128.6, 128.4, 127.4, 127.1, 126.1, 124.9, 124.3, 117.9, 61.3, 41.6, 17.7, 14.1, 14 ppm; HRMS: measured m/z 406.1626 (theoretical: 406.1625).

Ethyl (E)-4-[N-((4-trifluoromethoxy)benzyl)benzamide]-alpha-ethylcinnamate (9a)

Yield: 0.83 g (65%); $^1$H NMR (DMSO-$d_6$): δ 9.14 (t, J=5.9 Hz, 1H, $Ph_2$-OCNH), 7.99-7.27 (m, 8H, OCNH-$Ph_1$+$Ph_1$-OCNH—$CH_2$-$Ph_2$), 7.42 (s, 1H, OCNH-$Ph_1$-CH), 4.5 (d, J=5.4 Hz, 2H, $Ph_1$-OCNH—$CH_2$), 4.21 (q, J=7.2 Hz, 2H, C—COO—$CH_2$), 2.4 (q, J=7.8 Hz, 2H, CH—C—$CH_2$), 1.27 (t, J=7.3 Hz, 3H, COO—$CH_2$—$CH_3$), 1.09 (t, J=6.6 Hz, 3H, C—$CH_2$—$CH_3$) ppm; $^{13}$C-NMR (DMSO-$d_6$): 173.1, 169, 168.3, 155.8, 140.3, 136.7, 135.1, 131.4, 131.2, 128.7, 128.3, 127.6, 127.1, 125.1, 123.9, 122.3, 116.9, 59.3, 40.6, 16.7, 14.5, 14.1 ppm; HRMS: measured m/z 422.1574 (theoretical: 422.1574).

Ethyl (E)-4-[N-((4-methoxy)benzyl)benzamide]-alpha-ethylcinnamate (10a)

Yield: 0.91 g (67%); $^1$H NMR (Methanol-$d_3$): δ 7.8-6.6 (m, 8H, OCNH-$Ph_1$+$Ph_1$-OCNH—$CH_2$-$Ph_2$), 7.5 (s, 1H, OCNH-$Ph_1$-CH), 4.41 (s, 2H, $Ph_1$-OCNH—$CH_2$), 4.17 (q, J=7 Hz, 2H, C—COO—$CH_2$), 3.67 (s, Phe-O—$CH_3$), 2.44 (q, J=7.5 Hz, 2H, CH—C—$CH_2$), 1.24 (t, J=7.6 Hz, 3H, COO—$CH_2$—$CH_3$), 1.05 (t, J=5 Hz, 3H, CH—$CH_2$—$CH_3$) ppm; $^{13}$C-NMR (Methanol-$d_3$): 167, 166.3, 140.4, 138.3, 135.7, 135.1, 131.7, 130.3, 128.7, 128.5, 127.3, 127.1, 124.2, 123.1, 122.1, 115.9, 58.3, 55.1, 40.1, 16.5, 14.6, 14.1 ppm; HRMS: measured m/z 367.1783 (theoretical: 367.1784).

Ethyl (E)-4-[N-((4-chloro)benzyl)benzamide]-alpha-ethylcinnamate (11a)

Yield: 0.93 g (69%); $^1$H NMR (Methanol-$d_3$): δ 7.93-7.34 (m, 8H, OCNH-$Ph_1$+$Ph_1$-OCNH—$CH_2$-$Ph_2$), 7.36 (s, 1H, OCNH-$Ph_1$-CH), 4.58 (s, 2H, $Ph_1$-OCNH—$CH_2$), 4.3 (q, J=7.5 Hz, 2H, C—COO—$CH_2$), 2.56 (q, J=7.4 Hz, 2H, CH—C—$CH_2$), 1.37 (t, J=7.5 Hz, 3H, COO—$CH_2$—$CH_3$), 1.18 (t, J=7.2 Hz, 3H, C—$CH_2$—$CH_3$) ppm; $^{13}$C-NMR (Methanol-$d_3$): 166.6, 165.3, 154.4, 137.4, 136.1, 135.5, 131.6, 130.2, 129.1, 128.6, 126.9, 126.8, 125.3, 123.1, 122.8, 115.9, 59.3, 40.2, 16.1, 14.6, 14.1 ppm; HRMS: measured m/z 371.1296 (theoretical: 371.1298).

Ethyl (E)-4-[N-((4-phenoxy)benzyl)benzamide]-alpha-ethylcinnamate (12a)

Yield: 0.85 g (69%); $^1$H NMR (DMSO-$d_6$): δ 9.11 (t, J=5.9 Hz, 1H, $Ph_1$-OCNH), 7.97-6.98 (m, 12H, OCNH-$Ph_1$+$Ph_1$-OCNH—$CH_2$-$Ph_2$+$Ph_2$-O-$Ph_3$), 7.4 (s, 1H, OCNH-$Ph_1$-CH), 4.49 (d, J=6.5, 2H, $Ph_1$-OCNH—$CH_2$), 4.24 (q, J=7.2 Hz, 2H, C—COO—$CH_2$), 2.45 (q, J=7.3 Hz, 2H, CH—C—$CH_2$), 1.3 (t, J=7.7 Hz, 3H, COO—$CH_2$—$CH_3$), 1.12 (t, J=7.8 Hz, 3H, C—$CH_2$—$CH_3$) ppm; $^{13}C$-NMR (DMSO-$d_6$): 166.1, 164.2, 156.6, 155.4, 137.4, 136.1, 135.5, 131.6, 130.2, 129.1, 128.7, 128.6, 128.3, 126.9, 126.8, 125.3, 123.1, 122.8, 121.5, 118.1, 118.7, 115.9, 59.3, 40.2, 16.2, 14.5, 14 ppm; HRMS: measured m/z 430.2017 (theoretical: 430.2013).

Ethyl (E)-4-[N-((4-fluoro(2-trifluoromethyl))benzyl) benzamide]-alpha-ethylcinnamate (13a)

Yield: 0.85 g (70%); $^{1}H$ NMR (DMSO-$d_6$): δ 9.19 (t, J=5.3 Hz, 1H, $Ph_2$-OCNH), 8-7.53 (m, 8H, OCNH-$Ph_1$+$Ph_1$-OCNH—$CH_2$-$Ph_2$+$Ph_1$-CH), 4.65 (d, J=4.6 Hz, 2H, $Ph_1$-OCNH—$CH_2$), 4.24 (q, J=7 Hz, 2H, C—COO—$CH_2$), 2.48 (q, J=8.5 Hz, 2H, CH—C—$CH_2$), 1.3 (t, J=7.4 Hz, 3H, COO—$CH_2$—$CH_3$), 1.13 (t, J=7.1 Hz, 3H, C—$CH_2$—$CH_3$) ppm; $^{13}C$-NMR (DMSO-$d_6$): 175.4, 165.3, 141.9, 136.3, 135.3, 135.1, 132.6, 132.5, 129.4, 128.8, 128.2, 126.1, 126, 125.3, 125.1, 124.8, 124.1, 60.4, 40.1, 24.6, 14.1, 11 ppm; HRMS: measured m/z 424.1530 (theoretical: 424.1530).

Ethyl (E)-4-[N-((4-methoxy(2-trifluoromethyl))benzyl)benzamide]-alpha-ethylcinnamate (14a)

Yield: 0.9 g (70%); $^{1}H$ NMR (DMSO-$d_6$): δ 9.1 (t, J=4.7 Hz, 1H, $Ph_2$-OCNH), 8.02-7.24 (m, 7H, OCNH-$Ph_1$+$Ph_1$-OCNH—$CH_2$-$Ph_2$), 7.4 (s, 1H, OCNH-$Ph_1$-CH), 4.61 (d, J=5.1 Hz, 2H, $Ph_1$-OCNH—$CH_2$), 4.25 (q, J=7.1 Hz, 2H, C—COO—$CH_2$), 2.45 (q, J=7.7 Hz, 2H, CH—C—$CH_2$), 1.3 (t, J=8.5 Hz, 3H, COO—$CH_2$—$CH_3$), 1.12 (t, J=7.2 Hz, 3H, C—$CH_2$—$CH_3$) ppm; $^{13}C$-NMR (DMSO-$d_6$): 168.4, 166.3, 158.9, 136.4, 136.3, 135.9, 135.6, 132.5, 129.4, 128.8, 128.2, 126.3, 126.1, 125.3, 125, 124.8, 124.1, 60.1, 55.3, 40.1, 23.6, 13, 11 ppm; HRMS: measured m/z 436.1728 (theoretical: 436.1730).

Ethyl (E)-3-[N-((2-trifluoromethyl)benzyl)benzamide]-alpha-ethylcinnamate (15a)

Yield: 0.91 g (70%); $^{1}H$ NMR (Methanol-$d_3$): δ 7.82-7.32 (m, 8H, OCNH-$Ph_1$+$Ph_1$-OCNH—$CH_2$-$Ph_2$), 7.48 (s, 1H, OCNH-$Ph_1$-CH), 4.7 (s, 2H, $Ph_1$-OCNH—$CH_2$), 4.18 (q, J=7.22 Hz, 2H, COO—$CH_2$), 2.45 (q, J=7.6 Hz, 2H, CH—C—$CH_2$), 1.25 (t, J=7.1 Hz, 3H, COO—$CH_2$—$CH_3$), 1.07 (t, J=7.6 Hz, 3H, C—$CH_2$—$CH_3$) ppm; $^{13}C$-NMR (Methanol-$d_3$): 169.9, 169.4, 138.5, 137.5, 137.4, 135.8, 133.5, 133.2, 130, 129.8, 128.5, 128.3, 127.1, 127, 125, 124.8, 124.1, 62.1, 41.3, 21.7, 14.6, 14.1 ppm; HRMS: measured m/z 405.1552 (theoretical: 405.1553).

Ethyl (E)-4-[N-((2-trifluoromethyl)benzyl)benzamide]-cinnamate (16a)

Yield: 0.78 g (67%); $^{1}H$ NMR (DMSO-$d_6$): δ 9.19 (t, J=6 Hz, 1H, $Ph_2$-OCNH), 8-7.47 (m, 9H, OCNH-$Ph_1$+$Ph_1$-OCNH—$CH_2$-$Ph_2$+$Ph_1$-CH), 6.77 (d, J=16.2 Hz, 1H, $Ph_1$-CH—CH), 4.69 (d, J=5.7 Hz, 2H, $Ph_1$-OCNH—$CH_2$), 4.33 (q, J=7.5 Hz, 2H, CH—COO—$CH_2$), 1.28 (t, J=7.4 Hz, 3H, COO—$CH_2$—$CH_3$) ppm; $^{13}C$-NMR (DMSO-$d_6$): 170.9, 168.4, 137.5, 136.5, 136.4, 135.8, 132.5, 131.2, 130, 129.6, 128.4, 128.1, 127.5, 127.3, 125.1, 124.8, 124.2, 62.3, 41.1, 14.1 ppm; HRMS: measured m/z 378.1312 (theoretical: 378.1312).

Ethyl (E)-4-[N-((2-trifluoromethyl)benzyl)benzamide]-alpha-methylcinnamate (17a)

Yield: 0.83 g (65%); $^{1}H$ NMR (DMSO-$d_6$): δ 9.23 (t, J=6 Hz, 1H, $Ph_2$-OCNH), 8.06-7.51 (m, 9H, OCNH-$Ph_1$+$Ph_1$-OCNH—$CH_2$-$Ph_2$+$Ph_1$-CH), 4.73 (d, J=5.6 Hz, 2H, $Ph_1$-OCNH—$CH_2$), 4.28 (q, J=7.2 Hz, 2H, C—COO—$CH_2$), 3.37 (d, J=2.1, 3H, CH—C—$CH_3$), 1.34 (t, J=7 Hz, 3H, COO—$CH_2$—$CH_3$) ppm; $^{13}C$-NMR (DMSO-$d_6$): 168, 165, 139.5, 136.4, 136.3, 135.8, 129.5, 129.1, 128.9, 127.4, 127.1, 126.5, 126.3, 125.9, 125.1, 124.4, 124.2, 59.9, 42.1, 13.7, 11.9 ppm; HRMS: measured m/z 392.1469 (theoretical: 392.1468).

Ethyl (E)-4-[N-((2-trifluoromethyl)benzyl)benzamide]-alpha-propylcinnamate (18a)

Yield: 0.81 g (65%); $^{1}H$ NMR (DMSO-$d_6$): δ 9.18 (t, J=6 Hz, 1H, $Ph_2$-OCNH), 8-7.3 (m, 9H, OCNH-$Ph_1$+$Ph_1$-OCNH—$CH_2$-$Ph_2$+$Ph_1$-CH), 4.67 (d, J=5.3 Hz, 2H, $Ph_1$-OCNH—$CH_2$), 4.23 (q, J=7.4 Hz, 2H, C—COO—$CH_2$), 2.49-2.3 (m, 2H, CH—C—$CH_2$), 1.56-1.47 (m, 2H, C—$CH_2$—$CH_2$), 1.34 (t, J=7 Hz, 3H, COO—$CH_2$—$CH_3$), 0.9 (t, J=7 Hz, 3H, $CH_2$—$CH_2$—$CH_3$) ppm; $^{13}C$-NMR (DMSO-$d_6$): 167, 165.5, 138.5, 136.3, 136.2, 135.7, 130.5, 129.1, 128.7, 127.1, 127, 126.5, 126.2, 126.1, 125.7, 125, 124.6, 60, 42.1, 29, 20.1, 14.2, 13.7 ppm; HRMS: measured m/z 420.1780 (theoretical: 420.1781).

Ethyl (E)-4-[N-((2-trifluoromethyl)benzyl)benzamide]-alpha-phenylcinnamate (19a)

Yield: 0.62 g (60%); $^{1}H$ NMR (DMSO-$d_6$): δ 9.06 (t, J=6 Hz, 1H, $Ph_2$-OCNH), 7.98-7.15 (m, 14H, OCNH-$Ph_1$+$Ph_1$-OCNH—$CH_2$-$Ph_2$+$Ph_1$-CH+C-$Ph_4$), 4.62 (d, J=6 Hz, 2H, $Ph_1$-OCNH—$CH_2$), 4.23 (q, J=6.6 Hz, 2H, C—COO—$CH_2$), 1.24 (t, J=7.4 Hz, 3H, COO—$CH_2$—$CH_3$) ppm; $^{13}C$-NMR (DMSO-$d_6$): 166.5, 165.3, 136.5, 136.3, 136.2, 135.7, 134.2, 130.5, 129.1, 128.8, 128.6, 128.5, 128.4, 127.7, 127.1, 126.6, 126.5, 126.6, 126.2, 126.1, 125.7, 125, 124.6, 60, 42.1, 13.7 ppm; HRMS: measured m/z 454.1622 (theoretical: 454.1625).

General Procedure for the Preparation of the Compounds (1b-19b), Using the Example of Ethyl 2-ethyl 3-[4-(N-((2-trifluoromethyl)benzyl)benzamide)]propanoate (1b)

250 mg (0.617 mmol) la and 9.8 mg (0.1 mmol) palladium on carbon were solved in dry ethanol and stirred under hydrogen atmosphere for 12 h. Reaction mixture was filtered over celite and the solvent removed under reduced pressure. Without further purification clear resinous oil occurred. Yield: 0.2 g (90%); $^{1}H$ NMR (DMSO-$d_6$): δ 9.1 (t, J=5.8 Hz, 1H, $Ph_2$-OCNH), 7.91-7.34 (m, 8H, OCNH-$Ph_1$+$Ph_1$-OCNH—$CH_2$-$Ph_2$), 4.71 (d, J=5.5 Hz, 2H, $Ph_1$-OCNH—$CH_2$), 4.11-4.01 (m, 2H, CH—COO—$CH_2$), 2.97-2.83 (m, 2H, $Ph_1$-$CH_2$), 2.73-2.64 (m, 1H, $Ph_1$-$CH_2$—CH), 1.65-1.56 (m, 2H, $Ph_1$-$CH_2$—CH—$CH_2$), 1.14 (t, J=6.6 Hz, 3H, COO—$CH_2$—$CH_3$), 0.93 (t, J=7.4, 3H, CH—$CH_2$—$CH_3$) ppm; $^{13}C$-NMR (DMSO-$d_6$): 175.5, 168.8, 143.8, 137, 132.6, 132.04, 131.9, 128.2, 127.1, 127, 125.7, 125.6, 125.5, 125.4, 124.9, 60, 49, 39.8, 37.7, 25.2, 13.2, 10.5 ppm; HRMS: measured m/z 408.1781 (theoretical: 408.1781).

Ethyl 2-ethyl 3-[4-(N-benzylbenzamide)]propanoate (2b)

Yield: 0.21 g (84%); $^{1}H$ NMR (Methanol-$d_3$): δ 7.69-7.11 (m, 9H, OCNH-$Ph_1$+$Ph_1$-OCNH—$CH_2$-$Ph_2$), 4.46 (s, 2H, $Ph_1$-OCNH—$CH_2$), 3.98-3.88 (m, 2H, CH—COO—$CH_2$), 2.86-2.72 (m, 2H, $Ph_1$-$CH_2$), 2.58-2.48 (m, 1H, $Ph_1$-$CH_2$—

CH), 1.62-1.47 (m, 2H, $Ph_1$-$CH_2$—CH—$CH_2$), 1.02 (t, J=6.3 Hz, 3H, COO—$CH_2$—$CH_3$), 0.83 (t, J=8, 3H, CH—$CH_2$—$CH_3$) ppm; $^{13}$C-NMR (Methanol-$d_3$): 175.5, 168.6, 143.6, 138.8, 132.4, 128.8, 128.1, 127.1, 127, 126.8, 125.6, 125.5, 125.4, 125.3, 60, 49.1, 43, 37.7, 25, 13.3, 10.7 ppm; HRMS: measured m/z 340.191 (theoretical: 340.1907).

Ethyl 2-ethyl 3-[4-(N-((2-methyl)benzyl)benzamide)]propanoate (3b)

Yield: 0.19 g (75%); $^1$H NMR (DMSO-$d_6$): δ 8.85 (t, J=5.7 Hz, 1H, $Ph_2$-OCNH), 7.85-7.15 (m, 8H, OCNH-$Ph_1$+$Ph_1$-OCNH—$CH_2$-$Ph_2$), 4.46 (d, J=6.2, 2H, $Ph_1$-OCNH—$CH_2$), 4.16-3.96 (m, 2H, CH—COO—$CH_2$), 2.92-2.77 (m, 2H, $Ph_1$-$CH_2$), 2.68-2.59 (m, 1H, $Ph_1$-$CH_2$—CH), 2.34 (s, 3H, $Ph_2$-$CH_3$), 1.61-1.5 (m, 2H, $Ph_1$-$CH_2$—CH—$CH_2$), 1.09 (t, J=7.5 Hz, 3H, COO—$CH_2$—$CH_3$), 0.88 (t, J=8.1, 3H, CH—$CH_2$—$CH_3$) ppm; $^{13}$C-NMR (DMSO-$d_6$): 167.8, 165.4, 137.8, 136.2, 136, 135.8, 129, 128.2, 128.1, 127.4, 125.9, 125.8, 125.3, 124.2, 124, 60.3, 40.1, 38.3, 23.9, 18.9, 13.2, 12.1 ppm; HRMS: measured m/z 354.2065 (theoretical: 354.2064).

Ethyl 2-ethyl 3-[4-(N-((2-chloro)benzyl)benzamide)]propanoate (4b)

Yield 0.2 g (90%); $^1$H NMR (Methanol-$d_3$): δ 7.83-7.26 (m, 8H, OCNH-$Ph_1$+$Ph_1$-OCNH—$CH_2$-$Ph_2$), 4.61 (s, 2H, $Ph_1$-OCNH—$CH_2$), 4.11-4 (m, 2H, CH—COO—$CH_2$), 3-2.84 (m, 2H, $Ph_1$-$CH_2$), 2.71-2.62 (m, 1H, $Ph_1$-$CH_2$—CH), 1.74-1.59 (m, 2H, $Ph_1$-$CH_2$—CH—$CH_2$), 1.15 (t, J=6.8 Hz, 3H, COO—$CH_2$—$CH_3$), 0.96 (t, J=8.7, 3H, CH—$CH_2$—$CH_3$) ppm; $^{13}$C-NMR (DMSO-$d_6$): 167.8, 166.2, 137.4, 136.4, 135.9, 135.8, 129.2, 128.5, 128.3, 127.6, 126.9, 126.8, 125.4, 124.5, 124, 58.3, 40, 38.6, 23.9, 18.5, 13.1, 11.7 ppm; HRMS: measured m/z 375.1423 (theoretical: 375.1422).

Ethyl 2-ethyl 3-[4-(N-((2-bromo)benzyl)benzamide)]propanoate (5b)

Yield: 0.18 g (70%); $^1$H NMR (Methanol-$d_3$): δ 7.81-7.25 (m, 8H, OCNH-$Ph_1$+$Ph_1$-OCNH—$CH_2$-$Ph_2$), 4.59 (s, 2H, $Ph_1$-OCNH—$CH_2$), 4.09-4 (m, 2H, CH—COO—$CH_2$), 2.9-2.85 (m, 2H, $Ph_1$-$CH_2$), 2.69-2.61 (m, 1H, $Ph_1$-$CH_2$—CH), 1.72-1.58 (m, 2H, $Ph_1$-$CH_2$—CH—$CH_2$), 1.14 (t, J=7.9 Hz, 3H, COO—$CH_2$—$CH_3$), 0.95 (t, J=8.1, 3H, CH—$CH_2$—$CH_3$) ppm; $^{13}$C-NMR (Methanol-$d_3$): 176, 167.5, 144.9, 130.2, 129.5, 128.5, 128.4, 128.2, 127.2, 127, 126, 125.7, 125.6, 125.5, 61.4, 50.4, 44.4, 39.1, 26.6, 14.5, 11.9 ppm; HRMS: measured m/z 418.1013 (theoretical: 418.1012).

Ethyl 2-ethyl 3-[4-(N-((2-trifluoromethoxy)benzyl)benzamide)]propanoate (6b)

Yield: 0.2 g (90%); $^1$H NMR (Methanol-$d_3$): δ 7.69-7.17 (m, 8H, OCNH-$Ph_1$+$Ph_1$-OCNH—$CH_2$-$Ph_2$), 4.55 (s, 2H, $Ph_1$-OCNH—$CH_2$), 3.97-3.89 (m, 2H, CH—COO—$CH_2$), 2.86-2.73 (m, 2H, $Ph_1$-$CH_2$), 2.58-2.51 (m, 1H, $Ph_1$-$CH_2$—CH), 1.61-1.47 (m, 2H, $Ph_1$-$CH_2$—CH—$CH_2$), 1.02 (t, J=7 Hz, 3H, COO—$CH_2$—$CH_3$), 0.84 (t, J=7.6, 3H, CH—$CH_2$—$CH_3$) ppm; $^{13}$C-NMR (Methanol-$d_3$): 177.5, 175, 166.5, 145.1, 133.5, 132.6, 130.4, 130.3, 129.9, 128.6, 128.4, 127, 125.8, 125.6, 61.4, 50.5, 44.4, 39.1, 26.5, 14.7, 12 ppm; HRMS: measured m/z 423.1667 (theoretical: 423.1665).

Ethyl 2-ethyl 3-[4-(N-((4-fluoro)benzyl)benzamide)]propanoate (7b)

Yield: 0.23 g (91%); $^1$H NMR (DMSO-$d_6$): δ 8.91 (t, J=5.8 Hz, 1H, OCNH), 7.75-7.03 (m, 8H, OCNH-$Ph_1$+$Ph_1$-OCNH—$CH_2$-$Ph_2$), 4.37 (d, J=6, 2H, $Ph_1$-OCNH—$CH_2$), 3.98-3.86 (m, 2H, CH—COO—$CH_2$), 2.84-2.69 (m, 2H, $Ph_1$-$CH_2$), 2.6-2.48 (m, 1H, $Ph_1$-$CH_2$—CH), 1.53-1.41 (m, 2H, $Ph_1$-$CH_2$—CH—$CH_2$), 1.01 (t, J=7.4 Hz, 3H, COO—$CH_2$—$CH_3$), 0.79 (t, J=7.4, 3H, CH—$CH_2$—$CH_3$) ppm; $^{13}$C-NMR (DMSO-$d_6$): 177.6, 165.6, 143.4, 138.6, 133.4, 133.2, 132.1, 127.5, 127.1, 126.7, 126.6, 126.5, 125.4, 125.2, 56, 48.2, 45, 37.6, 24, 13.1, 11.7 ppm; HRMS: measured m/z 358.1814 (theoretical: 358.1813).

Ethyl 2-ethyl 3-[4-(N-((4-trifluoromethyl)benzyl)benzamide)]propanoate (8b)

Yield: 0.23 g (87%); $^1$H NMR (Methanol-$d_3$): δ 7.7-7.17 (m, 8H, OCNH-$Ph_1$+$Ph_1$-OCNH—$CH_2$-$Ph_2$), 4.54 (s, 2H, $Ph_1$-OCNH—$CH_2$), 3.99-3.88 (m, 2H, CH—COO—$CH_2$), 2.87-2.72 (m, 2H, $Ph_1$-$CH_2$), 2.59-2.49 (m, 1H, $Ph_1$-$CH_2$—CH), 1.62-1.46 (m, 2H, $Ph_1$-$CH_2$—CH—$CH_2$), 1.03 (t, J=7.5 Hz, 3H, COO—$CH_2$—$CH_3$), 0.83 (t, J=7.2, 3H, CH—$CH_2$—$CH_3$) ppm; $^{13}$C-NMR (Methanol-$d_3$): 175.6, 166.3, 143.5, 132.7, 132.3, 131.5, 130.4, 128.8, 127.5, 127.1, 125.1, 125.1, 125, 125, 124.9, 60, 49, 42.7, 37.7, 25.1, 13.2, 10.7 ppm; HRMS: measured m/z 408.178 (theoretical: 408.1781).

Ethyl 2-ethyl 3-[4-(N-((4-trifluoromethoxy)benzyl)benzamide)]propanoate (9b)

Yield: 0.24 g (94%); $^1$H NMR (Methanol-$d_3$): δ 7.69-7.12 (m, 8H, OCNH-$Ph_1$+$Ph_1$-OCNH—$CH_2$-$Ph_2$), 4.48 (s, 2H, $Ph_1$-OCNH—$CH_2$), 3.98-3.88 (m, 2H, CH—COO—$CH_2$), 2.87-2.71 (m, 2H, $Ph_1$-$CH_2$), 2.58-2.48 (m, 1H, $Ph_1$-$CH_2$—CH), 1.64-1.42 (m, 2H, $Ph_1$-$CH_2$—CH—$CH_2$), 1.02 (t, J=5.7 Hz, 3H, COO—$CH_2$—$CH_3$), 0.84 (t, J=7.4, 3H, CH—$CH_2$—$CH_3$) ppm; $^{13}$C-NMR (Methanol-$d_3$): 177.8, 175.6, 168.6, 143.8, 138.2, 132.1, 130.2, 130.3, 128.8, 128.7, 127, 125.3, 125.2, 125.1, 120.7, 60.1, 49.2, 42.5, 37.7, 25.2, 13.1, 10.6 ppm; HRMS: measured m/z 424.1726 (theoretical: 424.1730).

Ethyl 2-ethyl 3-[4-(N-((4-methoxy)benzyl)benzamide)]propanoate (10b)

Yield: 0.2 g (90%); $^1$H NMR (Methanol-$d_3$): δ 7.78-6.88 (m, 8H, OCNH-$Ph_1$+$Ph_1$-OCNH—$CH_2$-$Ph_2$), 4.45 (s, 2H, $Ph_1$-OCNH—$CH_2$), 4.1-3.98 (m, 2H, CH—COO—$CH_2$), 3.78 (s, 3H, $Ph_2$-O—$CH_3$), 2.96-2.83 (m, 2H, $Ph_1$-$CH_2$), 2.68-2.61 (m, 1H, $Ph_1$-$CH_2$—CH), 1.73-1.56 (m, 2H, $Ph_1$-$CH_2$—CH—$CH_2$), 1.14 (t, J=7.1 Hz, 3H, COO—$CH_2$—$CH_3$), 0.95 (t, J=7.5, 3H, CH—$CH_2$—$CH_3$) ppm; $^{13}$C-NMR (Methanol-$d_3$): 177.1, 160.5, 144.9, 133.8, 132.2, 130.1, 129.9, 128.4, 127.2, 127, 125.3, 125.2, 125.1, 114.9, 61.4, 55.8, 44, 39.1, 37.7, 26.6, 14.6, 11.9 ppm; HRMS: measured m/z 370.2017 (theoretical: 370.2013).

Ethyl 2-ethyl 3-[4-(N-((4-chloro)benzyl)benzamide)]propanoate (11b)

Yield: 0.2 g (91%); $^1$H NMR (Methanol-$d_3$): δ 7.68-7.12 (m, 8H, OCNH-$Ph_1$+$Ph_1$-OCNH—$CH_2$-$Ph_2$), 4.46 (s, 2H, $Ph_1$-OCNH—$CH_2$), 3.98-3.87 (m, 2H, CH—COO—$CH_2$), 2.85-2.73 (m, 2H, $Ph_1$-$CH_2$), 2.57-2.5 (m, 1H, $Ph_1$-$CH_2$—

CH), 1.62-1.45 (m, 2H, $Ph_1$-$CH_2$—CH—$CH_2$), 1.02 (t, J=7.1 Hz, 3H, COO—$CH_2$—$CH_3$), 0.83 (t, J=7.4, 3H, CH—$CH_2$—$CH_3$) ppm; $^{13}$C-NMR (Methanol-$d_3$): 177, 164.1, 145, 140.2, 130.2, 129.5, 128.5, 128.5, 128.4, 127, 125.5, 125.3, 125.1, 114.4, 61.4, 50.5, 44.5, 39, 26.6, 14.5, 12.1 ppm; HRMS: measured m/z 374.1518 (theoretical: 374.1518).

Ethyl 2-ethyl 3-[4-(N-((4-phenoxy)benzyl)benzamide)]propanoate (12b)

Yield: 0.2 g (90%); $^1$H NMR (Methanol-$d_3$): δ 7.68-7.12 (m, 13H, OCNH-$Ph_1$+$Ph_1$-OCNH—$CH_2$-$Ph_2$), 4.46 (s, 2H, $Ph_1$-OCNH—$CH_2$), 3.98-3.87 (m, 2H, CH—COO—$CH_2$), 2.85-2.73 (m, 2H, $Ph_1$-$CH_2$), 2.57-2.5 (m, 1H, $Ph_1$-$CH_2$—CH), 1.62-1.45 (m, 2H, $Ph_1$-$CH_2$—CH—$CH_2$), 1.02 (t, J=7.1 Hz, 3H, COO—$CH_2$—$CH_3$), 0.83 (t, J=7.4, 3H, CH—$CH_2$—$CH_3$) ppm; $^{13}$C-NMR (Methanol-$d_3$): 175.7, 168.5, 157.4, 156.5, 143.7, 136.1, 134, 132.4, 130.2, 129.5, 128.8, 128.7, 127, 126.9, 126.8, 125.3, 123.1, 122, 121.5, 118.5, 118.3, 115.9, 60.1, 42.2, 25.2, 13.2, 10.5 ppm; HRMS: measured m/z 370.2017 (theoretical: 370.2013).

Ethyl 2-ethyl 3-[4-(N-(4-fluoro(2-trifluoromethyl)benzyl)benzamide)]propanoate (13b)

Yield: 0.2 g (90%); $^1$H NMR (Methanol-$d_3$): δ 7.83-7.18 (m, 7H, OCNH-$Ph_1$+$Ph_1$-OCNH—$CH_2$-$Ph_2$), 4.63 (s, 2H, $Ph_1$-OCNH—$CH_2$), 4.01-3.86 (m, 2H, CH—COO—$CH_2$), 2.88-2.72 (m, 2H, $Ph_1$-$CH_2$), 2.59-2.49 (m, 1H, $Ph_1$-$CH_2$—CH), 1.65-1.43 (m, 2H, $Ph_1$-$CH_2$—CH—$CH_2$), 1.03 (t, J=7.04 Hz, 3H, COO—$CH_2$—$CH_3$), 0.84 (t, J=7.7, 3H, CH—$CH_2$—$CH_3$) ppm; $^{13}$C-NMR (Methanol-$d_3$): 175.6, 168.8, 163, 159.7, 143.8, 133.1, 131.9, 131, 130.9, 128.9, 127.1, 118.9, 118.6, 113.3, 112.9, 60, 49.1, 39.3, 37.4, 25.2, 13, 10.6 ppm; HRMS: measured m/z 426.1686 (theoretical: 426.1687).

Ethyl 2-ethyl 3-[4-(N-(4-methoxy(2-trifluoromethyl)benzyl)benzamide)]propanoate (14b)

Yield: 0.2 g (90%); $^1$H NMR (Methanol-$d_3$): δ 7.71-7.02 (m, 7H, OCNH-$Ph_1$+$Ph_1$-OCNH—$CH_2$-$Ph_2$), 4.59 (s, 2H, $Ph_1$-OCNH—$CH_2$), 4.01-3.86 (m, 2H, CH—COO—$CH_2$), 3.74 (s, 3H, $Ph_2$-O—$CH_3$), 2.87-2.72 (m, 2H, $Ph_1$-$CH_2$), 2.59-2.49 (m, 1H, $Ph_1$-$CH_2$—CH), 1.65-1.43 (m, 2H, $Ph_1$-$CH_2$—CH—$CH_2$), 1.03 (t, J=7 Hz, 3H, COO—$CH_2$—$CH_3$), 0.84 (t, J=7.3, 3H, CH—$CH_2$—$CH_3$) ppm; $^{13}$C-NMR (Methanol-$d_3$): 175.7, 168.8, 158.8, 151.2, 143.9, 132.1, 130.3, 128.8, 128.7, 128.6, 128.3, 127.2, 116.7, 111.8, 111.7, 67.9, 59.9, 55.1, 39.5, 37.9, 25.1, 13.2, 10.8 ppm; HRMS: measured m/z 438.1882 (theoretical: 438.1887).

Ethyl 2-ethyl 3-[13-(N-((2-trifluoromethyl)benzyl)benzamide)]propanoate (15b)

Yield: 0.14 g (55%); $^1$H NMR (Methanol-$d_3$): δ 7.65-7.27 (m, 8H, OCNH-$Ph_1$+$Ph_1$-OCNH—$CH_2$-$Ph_2$), 4.69 (s, 2H, $Ph_1$-OCNH—$CH_2$), 3.93 (q, J=7.2, 2H, CH—COO—$CH_2$), 2.87-2.74 (m, 2H, $Ph_1$-$CH_2$), 2.59-2.51 (m, 1H, $Ph_1$-$CH_2$—CH), 1.64-1.46 (m, 2H, $Ph_1$-$CH_2$—CH—$CH_2$), 1.01 (t, J=7.1 Hz, 3H, COO—$CH_2$—$CH_3$), 0.84 (t, J=7.4 Hz, 3H, CH—$CH_2$—$CH_3$) ppm; $^{13}$C-NMR (Methanol-$d_3$): 177.1, 168.8, 141.6, 140.5, 135.4, 133.5, 133.5, 129.7, 129.1, 128.5, 127.1, 126.5, 125.5, 125.4, 124.9, 61.5, 50.7, 39.8, 39.2, 26.5, 14.6, 12.1 ppm; HRMS: measured m/z 408.1781 (theoretical: 408.1781).

Ethyl 3-[4-(N-((2-trifluoromethyl)benzyl)benzamide)]propanoate (16b)

Yield: 0.24 g (95%); $^1$H NMR (DMSO-$d_6$): δ 9.1 (t, J=5.8 Hz, 1H, OCNH), 7.94-7.35 (m, 8H, OCNH-$Ph_1$+$Ph_1$-OCNH—$CH_2$-$Ph_2$), 4.71 (d, J=6.2 Hz, 2H, $Ph_1$-OCNH—$CH_2$), 4.1 (q, J=7 Hz, 2H, $CH_2$—COO—$CH_2$), 2.97 (t, J=7.6 Hz, 2H, $Ph_1$-$CH_2$), 2.71 (t, J=7.1 Hz, 2H, $Ph_1$-$CH_2$—$CH_2$), 1.21 (t, J=7 Hz, 3H, COO—$CH_2$—$CH_3$) ppm; $^{13}$C-NMR (DMSO-$d_6$): 177.1, 168.8, 141.6, 140.5, 135.4, 133.5, 133.5, 129.7, 129.1, 128.5, 127.1, 126.5, 125.5, 125.4, 124.9, 61.5, 50.7, 39.8, 39.2 ppm; HRMS: measured m/z 380.1468 (theoretical: 380.1468).

Ethyl 2-methyl 3-[4-(N-((2-trifluoromethyl)benzyl)benzamide)]propanoate (17b)

Yield: 0.2 g (93%); $^1$H NMR (DMSO-$d_6$): δ 9.04 (t, J=6 Hz, 1H, OCNH), 7.86-7.27 (m, 8H, OCNH-$Ph_1$+$Ph_1$-OCNH—$CH_2$-$Ph_2$), 4.65 (d, J=5.5 Hz, 2H, $Ph_1$-OCNH—$CH_2$), 4.01 (q, J=6.8 Hz, 2H, CH—COO—$CH_2$), 3-2.88 (m, 1H, $Ph_1$-$CH_2$—CH), 2.82-2.7 (m, 2H, $Ph_1$-$CH_2$), 1.14-1.05 (m, 6H, COO—$CH_2$—$CH_3$+$CH_2$—CH—$CH_3$) ppm; $^{13}$C-NMR (DMSO-$d_6$): 177.4, 166.8, 143.5, 140.5, 133.1, 132.5, 131.5, 129.7, 129.3, 128.6, 127.8, 126.5, 125.5, 125.4, 124.9, 60.2, 50.7, 39.8, 39.2, 17.2, 14.6 ppm; HRMS: measured m/z 394.1625 (theoretical: 394.1525).

Ethyl 2-propyl 3-[4-(N-((2-trifluoromethyl)benzyl)benzamide)]propanoate (18b)

Yield: 0.17 g (66%); $^1$H NMR (DMSO-$d_6$): δ 9.06 (t, J=5.75 Hz, 1H, OCNH), 7.85-7.28 (m, 8H, OCNH-$Ph_1$+$Ph_1$-OCNH—$CH_2$-$Ph_2$), 4.65 (d, J=4.25 Hz, 2H, $Ph_1$-OCNH—$CH_2$), 3.99 (q, J=7.3 Hz, 2H, CH—COO—$CH_2$), 3.07-2.9 (m, 2H, $Ph_1$-$CH_2$), 2.82-2.76 (m, 1H, $Ph_1$-$CH_2$—CH), 1.61-1.39 (m, 2H, $Ph_1$-$CH_2$—CH—$CH_2$), 1.07 (t, J=7.2 Hz, 3H, COO—$CH_2$—$CH_3$), 1.35-1.16 (m, 2H, $Ph_1$-$CH_2$—CH—$CH_2$—$CH_2$), 0.85 (t, J=7.13 Hz, 3H, CH—$CH_2$—$CH_2$—$CH_3$) ppm; $^{13}$C-NMR (DMSO-$d_6$): 175, 166.7, 143.5, 138.1, 132.9, 132.4, 131.5, 129.7, 129.2, 128.6, 127.7, 126.2, 125.5, 125.4, 124.9, 42.7, 38.1, 34.6, 34.4, 20.3, 14.5, 14.2 ppm; HRMS: measured m/z 422.1936 (theoretical: 422.1937).

Ethyl 2-phenyl 3-[4-(N-((2-trifluoromethyl)benzyl)benzamide)]propanoate (19b)

Yield: 0.1 g (40%); $^1$H NMR (DMSO-$d_6$): δ 9.02 (t, J=6 Hz, 1H, OCNH), 7.81-7.24 (m, 13H, OCNH-$Ph_1$+$Ph_1$-OCNH—$CH_2$-$Ph_2$+$CH_2$—CH-$Ph_4$), 4.63 (d, J=5.5 Hz, 2H, $Ph_1$-OCNH—$CH_2$), 4.08-3.92 (m, 2H, CH—COO—$CH_2$), 3.4-3.31 (m, 2H, $Ph_1$-$CH_2$), 3.11-3.03 (m, 1H, $Ph_1$-$CH_2$—CH), 1.07 (t, J=7.1 Hz, 3H, COO—$CH_2$—$CH_3$) ppm; $^{13}$C-NMR (DMSO-$d_6$): 173, 166.8, 143.1, 139, 138.2, 138.1, 133.1, 132.5, 129.4, 129, 128.6, 128.3, 127.7, 127.7, 127.7, 126.6, 126.5, 126.6, 126.2, 126.1, 125.7, 125, 124.6, 60.9, 19, 14.5 ppm; HRMS: measured m/z 456.1785 (theoretical: 456.1781).

General Procedure for the Preparation of the Compounds (1d-19d & 1c-19c), Using the Example of (E)-4-[N-((2-Trifluoromethyl)benzyl)benzamide]-alpha-ethylcinnamic acid (1d)

100 mg (0.2 mmol) Ethyl (E)-4-[N-((2-Trifluoromethyl)benzyl)benzamide]-alpha-ethylcinnamat (1a) and 69 mg (1.2 mmol) were solved in 2 ml of a mixture THF|$H_2O$|MeOH in the ratio 1:2:1 and stirred in a microwave for 30 min at 70° C. and 35 watt. The organic layer was removed under reduced pressure. The aqueous layer was diluted with 1 ml $H_2O$, acidified with 12 M HCl solution and stored at 4° C. The pure product precipitated and no further purification was needed. Yield: 0.06 g (60%); $^1$H NMR (DMSO-$d_6$): δ 12.71 (s, 1H, COOH), 9.24 (t, J=5.9 Hz, 1H, $Ph_2$-OCNH), 8.06-7.47 (m, 9H, OCNH-$Ph_1$+$Ph_1$-OCNH—$CH_2$-$Ph_2$+$Ph_1$-CH), 4.74 (d, J=5.2 Hz, 2H, $Ph_1$-OCNH—$CH_2$), 2.51 (q, J=8 Hz, 2H, CH—C—$CH_2$), 1.17 (t, J=7.5 Hz, 3H, C—$CH_2$—$CH_3$) ppm; $^{13}$C-NMR (DMSO-$d_6$): 169.8, 168.4, 139.3, 137, 136.7, 133.5, 132.1, 128.9, 128.3, 127.9, 127.7, 127.3, 127.1, 127, 126.9, 125.7, 125.6, 40, 20.4, 12.8 ppm; HRMS: measured m/z 378.1312 (theoretical: 378.1313).

(E)-4-[N-Benzylbenzamide]-alpha-ethylcinnamic acid (2d)

Yield: 0.06 g (65%); $^1$H NMR (DMSO-$d_6$): δ 12.61 (s, 1H, COOH), 9.11 (t, J=5.9 Hz, 1H, $Ph_2$-OCNH), 7.99-7.22 (m, 9H, OCNH-$Ph_1$+$Ph_1$-OCNH—$CH_2$-$Ph_2$), 7.33 (s, 1H, $Ph_1$-CH), 4.5 (d, J=6.1 Hz, 2H, $Ph_1$-OCNH—$CH_2$), 2.47 (q, J=7.7 Hz, 2H, CH—C—$CH_2$), 1.11 (t, J=7.2 Hz, 3H, C—$CH_2$—$CH_3$) ppm; $^{13}$C-NMR (DMSO-$d_6$): 168.9, 165.7, 139.7, 138, 136.4, 136.3, 128.9, 128.3, 127.5, 127.2, 126.7, 125.2, 125.1, 124, 123.5, 123, 42.7, 20.3, 13.3 ppm; HRMS: measured m/z 310.1438 (theoretical: 310.1438).

(E)-4-[N-((2-Methyl)benzyl)benzamide]-alpha-ethylcinnamic acid (3d)

Yield: 0.02 g (19%); $^1$H NMR (DMSO-$d_6$): δ 12.62 (s, 1H, COOH), 8.97 (t, J=5.8 Hz, 1H, $Ph_2$-OCNH), 7.98-7.13 (m, 8H, OCNH-$Ph_1$+$Ph_1$-OCNH—$CH_2$-$Ph_2$), 7.17 (s, 1H, $Ph_1$-CH), 4.48 (d, J=5.7 Hz, 2H, $Ph_1$-OCNH—$CH_2$), 2.48 (q, J=8.5 Hz, 2H, CH—C—$CH_2$), 2.34 (s, 3H, $Ph_2$-$CH_3$), 1.12 (t, J=7.1 Hz, 3H, C—$CH_2$—$CH_3$) ppm; $^{13}$C-NMR (DMSO-$d_6$): 169.8, 168.1, 139.1, 137, 136.6, 136, 135.9, 133.9, 129.9, 128.9, 128.6, 127.9, 127.4, 127.2, 126.9, 126.9, 41.4, 20.3, 18.7, 12.8 ppm; HRMS: measured m/z 324.1595 (theoretical: 324.1594).

(E)-4-[N-((2-Chloro)benzyl)benzamide]-alpha-ethylcinnamic acid (4d)

Yield: 0.06 g (62%); $^1$H NMR (DMSO-$d_6$): δ 12.69 (s, 1H, COOH), 9.17 (t, J=6 Hz, 1H, $Ph_2$-OCNH), 8.05-7.35 (m, 9H, OCNH-$Ph_1$+$Ph_1$-OCNH—$CH_2$-$Ph_2$+$Ph_1$-CH), 4.62 (d, J=5.8 Hz, 2H, $Ph_1$-OCNH—$CH_2$), 2.5 (q, J=6.4 Hz, 2H, CH—C—$CH_2$), 1.17 (t, J=7.2 Hz, 3H, C—$CH_2$—$CH_3$) ppm; $^{13}$C-NMR (DMSO-$d_6$): 169.8, 168.3, 139.2, 137, 136.6, 135.7, 133.7, 132.9, 129.1, 128.9, 128.6, 128.4, 127.9, 127.3, 126.9, 126.4, 41.2, 20.3, 12.7 ppm; HRMS: measured m/z 344.1052 (theoretical: 344.1048).

(E)-4-[N-((2-Bromo)benzyl)benzamide]-alpha-ethylcinnamic acid (5d)

Yield: 0.06 g (61%); $^1$H NMR (DMSO-$d_6$): δ 12.68 (s, 1H, COOH), 9.18 (t, J=5.7 Hz, 1H, $Ph_2$-OCNH), 8.08-7.26 (m, 9H, OCNH-$Ph_1$+$Ph_1$-OCNH—$CH_2$-$Ph_2$+$Ph_1$-CH), 4.58 (d, J=5.4 Hz, 2H, $Ph_1$-OCNH—$CH_2$), 2.5 (q, J=8.2 Hz, 2H, CH—C—$CH_2$), 1.18 (t, J=7 Hz, 3H, C—$CH_2$—$CH_3$) ppm; $^{13}$C-NMR (DMSO-$d_6$): 169.8, 168.3, 139.2, 137.2, 137, 136.6, 133.7, 132.4, 128.9, 128.6, 127.9, 127.4, 127.3, 126.9, 125.6, 122.7, 43.7, 20.4, 12.8 ppm; HRMS: measured m/z 388.0544 (theoretical: 388.0543).

(E)-4-[N-((2-Trifluoromethoxy)benzyl)benzamide]-alpha-ethylcinnamic acid (6d)

Yield: 0.06 g (65%); $^1$H NMR (DMSO-$d_6$): δ 12.71 (s, 1H, COOH), 9.15 (t, J=6.7 Hz, 1H, $Ph_2$-OCNH), 8.03-7.4 (m, 9H, OCNH-$Ph_1$+$Ph_1$-OCNH—$CH_2$-$Ph_2$+$Ph_1$-CH), 4.62 (d, J=5.9 Hz, 2H, $Ph_1$-OCNH—$CH_2$), 2.51 (q, J=6.9 Hz, 2H, CH—C—$CH_2$), 1.16 (t, J=7.9 Hz, 3H, C—$CH_2$—$CH_3$) ppm; $^{13}$C-NMR (DMSO-$d_6$): 171.3, 169.2, 166.5, 166.4, 149.7, 146.6, 138.8, 136.9, 134.1, 133.1, 132.2, 129.7, 129.5, 129.1, 128.2, 128, 128, 37.7, 20.8, 14.1 ppm; HRMS: measured m/z 394.1261 (theoretical: 394.1261).

(E)-4-[N-((4-Fluoro)benzyl)benzamide]-alpha-ethylcinnamic acid (7d)

Yield: 0.07 g (70%); $^1$H NMR (DMSO-$d_6$): δ 12.63 (s, 1H, COOH), 9.12 (t, J=6.3 Hz, 1H, $Ph_2$-OCNH), 7.97-7.12 (m, 9H, OCNH-$Ph_1$+$Ph_1$-OCNH—$CH_2$-$Ph_2$+$Ph_1$-CH), 4.48 (d, J=5.6 Hz, 2H, $Ph_1$-OCNH—$CH_2$), 2.44 (q, J=8.9 Hz, 2H, CH—C—$CH_2$), 1.11 (t, J=6.9 Hz, 3H, C—$CH_2$—$CH_3$) ppm; $^{13}$C-NMR (DMSO-$d_6$): 169.8, 168.1, 139.1, 137, 136.6, 134.9, 133.8, 129.1, 129, 128.9, 127.9, 127.2, 126.8, 125.6, 114.9, 114.6, 42.4, 20.3, 12.7 ppm; HRMS: measured m/z 328.1345 (theoretical: 328.1344).

(E)-4-[N-((4-Trifluoromethyl)benzyl)benzamide]-alpha-ethylcinnamic acid (8d)

Yield: 0.05 g (50%); $^1$H NMR (Methanol-$d_3$): δ 8.08-7.29 (m, 9H, OCNH-$Ph_1$+$Ph_1$-OCNH—$CH_2$-$Ph_2$+$Ph_1$-CH), 4.7 (s, 2H, $Ph_1$-OCNH—$CH_2$), 2.57 (q, J=7.5 Hz, 2H, CH—C—$CH_2$), 1.22 (t, J=7.2 Hz, 3H, C—$CH_2$—$CH_3$) ppm; $^{13}$C-NMR (Methanol-$d_3$): 167.2, 166.5, 144.2, 138.4, 138.1, 137, 136.5, 133.8, 133.6, 132.2, 129.6, 129.4, 128.6, 128.5, 127.1, 127, 126.8, 29.5, 19.4, 12.6 ppm; HRMS: measured m/z 377.1245 (theoretical: 377.1246).

(E)-4-[N-((4-Trifluoromethoxy)benzyl)benzamide]-alpha-ethylcinnamic acid (9d)

Yield: 0.07 g (69%); $^1$H NMR (Methanol-$d_3$): δ 7.96-7.24 (m, 9H, OCNH-$Ph_1$+$Ph_1$-OCNH—$CH_2$-$Ph_2$+$Ph_1$-CH), 4.64 (s, 2H, $Ph_1$-OCNH—$CH_2$), 2.56 (q, J=7.4 Hz, 2H, CH—C—$CH_2$), 1.19 (t, J=9.6 Hz, 3H, C—$CH_2$—$CH_3$) ppm; $^{13}$C-NMR (Methanol-$d_3$): 169.7, 168.2, 165.5, 145.2, 139.2, 138.2, 137, 136.6, 134.1, 133.7, 132.2, 129.7, 129.5, 129.1, 128.2, 128, 120.8, 28.5, 20.4, 12.7 ppm; HRMS: measured m/z 394.1258 (theoretical: 394.1261).

(E)-4-[N-((4-Methoxy)benzyl)benzamide]-alpha-ethylcinnamic acid (10d)

Yield: 0.06 g (64%); $^1$H NMR (DMSO-$d_6$) δ 12.51 (s, 1H, COOH), 8.93 (t, J=6.2 Hz, 1H, $Ph_2$-OCNH), 7.87-6.78 (m, 9H, OCNH-$Ph_1$+$Ph_1$-OCNH—$CH_2$-$Ph_2$+$Ph_1$-CH), 4.33 (d, J=5.7 Hz, 2H, $Ph_1$-OCNH—$CH_2$), 3.64 (s, 3H, $Ph_2$-O—$CH_3$), 2.36 (q, J=7.9 Hz, 2H, CH—C—$CH_2$), 1.01 (t, J=7.1 Hz, 3H, C—$CH_2$—$CH_3$) ppm; $^{13}$C-NMR (DMSO-$d_6$): 169.8, 168, 159, 139, 137, 136.5, 133.9, 130.8, 128.9, 128.7, 128.5, 128.5, 127.9, 127.2, 126.8, 113.5, 54.3, 46.8, 20.3, 12.7 ppm; HRMS: measured m/z 340.1544 (theoretical: 340.1543).

(E)-4-[N-((4-Chloro)benzyl)benzamide]-alpha-ethylcinnamic acid (11d)

Yield: 0.06 g (66%); $^1$H NMR (DMSO-$d_6$) δ 12.54 (s, 1H, COOH), 9.03 (t, J=5.8 Hz, 1H, $Ph_2$-OCNH), 7.87-7.23 (m, 9H, OCNH-$Ph_1$+$Ph_1$-OCNH—$CH_2$-$Ph_2$+$Ph_1$-CH), 4.39 (d, J=6.1 Hz, 2H, $Ph_1$-OCNH—$CH_2$), 2.37 (q, J=7.4 Hz, 2H, CH—C—$CH_2$), 1.01 (t, J=7.6 Hz, 3H, C—$CH_2$—$CH_3$) ppm; $^{13}$C-NMR (DMSO-$d_6$): 168.7, 166.1, 137.1, 137, 135.6, 133.9, 133.6, 129.4, 129.2, 128.9, 128, 127.6, 126.4, 125.4, 114.8, 114.6, 37.4, 21.3, 12.7 ppm; HRMS: measured m/z 344.1045 (theoretical: 344.1048).

(E)-4-[N-((4-Phenoxy)benzyl)benzamide]-alpha-ethylcinnamic acid (12d)

Yield: 0.02 g (16%); $^1$H NMR (Methanol-$d_3$) δ 7.96-6.95 (m, 14H, OCNH-$Ph_1$+$Ph_1$-OCNH—$CH_2$-$Ph_2$+$Ph_1$-CH+$Ph_2$-O-$Ph_3$), 4.6 (s, 2H, $Ph_1$-OCNH—$CH_2$), 2.56 (q, J=7.1 Hz, 2H, CH—C—$CH_2$), 1.2 (t, J=7.5 Hz, 3H, C—$CH_2$—$CH_3$) ppm; $^{13}$C-NMR (Methanol-$d_3$): 169.8, 168.1, 157.4, 155.4, 139.1, 137, 136.5, 133.9, 133.8, 133.8, 129.5, 128.9, 128.8, 127.9, 127.2, 126.9, 122.9, 122.8, 121.5, 118.5, 118.3, 115.9, 42.8, 20.3, 12.8 ppm; HRMS: measured m/z 402.1696 (theoretical: 402.1699).

(E)-4-[N-((4-Fluoro(2-trifluoromethyl))benzyl)benzamide]-alpha-ethylcinnamic acid (13d)

Yield: 0.06 g (60%); $^1$H NMR (Methanol-$d_3$) δ 8.11-7.36 (m, 8H, OCNH-$Ph_1$+$Ph_1$-OCNH—$CH_2$-$Ph_2$+$Ph_1$-CH), 4.79 (s, 2H, $Ph_1$-OCNH—$CH_2$), 2.57 (q, J=7.43 Hz, 2H, CH—C—$CH_2$), 1.2 (t, J=7.4 Hz, 3H, C—$CH_2$—$CH_3$) ppm; $^{13}$C-NMR (Methanol-$d_3$): 169.7, 168.4, 141.9, 139.4, 136.9, 136.7, 133.5, 131.2, 131, 128.9, 128.2, 127.3, 126, 125.3, 125.1, 124.8, 124.1, 39.4, 20.4, 12.8 ppm; HRMS: measured m/z 396.1215 (theoretical: 396.1217).

(E)-4-[N-((4-Methoxy(2-trifluoromethyl))benzyl)benzamide]-alpha-ethylcinnamic acid (14d)

Yield: 0.05 g (55%); $^1$H NMR (Methanol-$d_3$) δ 7.97-6.65 (m, 8H, OCNH-$Ph_1$+$Ph_1$-OCNH—$CH_2$-$Ph_2$+$Ph_1$-CH), 4.75 (s, 2H, $Ph_1$-OCNH—$CH_2$), 3.87 (s, 3H, $Ph_2$-$CH_3$), 2.57 (q, J=7.6 Hz, 2H, CH—C—$CH_2$), 1.2 (t, J=7.4 Hz, 3H, C—$CH_2$—$CH_3$) ppm; $^{13}$C-NMR (Methanol-$d_3$): 169.7, 168.3, 158.9, 139.3, 137.1, 136.6, 133.6, 130.5, 128.9, 128.1, 127.9, 127.3, 126.9, 126.1, 116.7, 112, 111.8, 54.7, 20.3, 12.6 ppm; HRMS: measured m/z 408.1415 (theoretical: 408.1417).

(E)-3-[N-((2-Trifluoromethyl)benzyl)benzamide]-alpha-ethylcinnamic acid (15d)

Yield: 0.05 g (50%); $^1$H NMR (DMSO1-$d_6$): δ 12.66 (s, 1H, COOH), 9.22 (t, J=5.8, 1H, OCNH), 8.02-7.47 (m, 8H, OCNH-$Ph_1$+$Ph_1$-OCNH—$CH_2$-$Ph_2$+OCNH-$Ph_1$-CH), 4.73 (d, J=6, 2H, $Ph_1$-OCNH—$CH_2$), 2.54-2.43 (m, 2H, CH—C—$CH_2$), 1.17 (t, J=7.2 Hz, 3H, C—$CH_2$—$CH_3$) ppm; $^{13}$C-NMR (DMSO-$d_6$): 170, 165, 137.5, 137, 136, 135.6, 133.4, 133, 130, 129.4, 128.3, 128.3, 127.2, 127, 124.9, 124.8, 124.1, 38.2, 20.1, 14.2 ppm; HRMS: measured m/z 377.3571 (theoretical: 377.3572).

(E)-4-[N-((2-Trifluoromethyl)benzyl)benzamide]-cinnamic acid (16d)

Yield: 0.07 g (72%); $^1$H NMR (DMSO-$d_6$): δ 12.4 (s, 1H, COOH), 9.1 (t, J=5.5 Hz, 1H, $Ph_2$-OCNH), 7.91-7.38 (m, 9H, OCNH-$Ph_1$+$Ph_1$-OCNH—$CH_2$-$Ph_2$+$Ph_1$-CH), 6.58 (d, J=16 Hz, 1H, H), 4.6 (d, J=5.7 Hz, 2H, $Ph_1$-OCNH—$CH_2$) ppm; $^{13}$C-NMR (DMSO-$d_6$): 169.8, 168.3, 139.3, 137, 136.7, 133.5, 132.1, 128.9, 128.3, 127.9, 127.3, 127.1, 127, 126.9, 126.7, 125.7, 125.6, 40 ppm; HRMS: measured m/z 350.1 (theoretical: 350.1).

(E)-4-[N-((2-Trifluoromethyl)benzyl)benzamide]-alpha-methylcinnamic acid (17d)

Yield: 0.07 g (71%); $^1$H NMR (DMSO-$d_6$): δ 12.62 (s, 1H, COOH), 9.23 (t, J=5.8 Hz, 1H, Phe-OCNH), 8.06-7.51 (m, 9H, OCNH-$Ph_1$+$Ph_1$-OCNH—$CH_2$-$Ph_2$+$Ph_1$-CH), 4.74 (d, J=5.6 Hz, 2H, $Ph_1$-OCNH—$CH_2$), 2.12 (d, J=1.4, 3H, CH—C—$CH_3$) ppm; $^{13}$C-NMR (DMSO-$d_6$): 169.1, 166, 138.6, 137.5, 136.7, 134.9, 133.5, 132.7, 130.2, 130, 130, 129.6, 128.2, 127.5, 127.4, 127.3, 126.8, 41.1, 12.3 ppm; HRMS: measured m/z 364.1158 (theoretical: 364.1155).

(E)-4-[N-((2-Trifluoromethyl)benzyl)benzamide]-alpha-propylcinnamic acid (18d)

Yield: 0.02 g (18%); $^1$H NMR (DMSO-$d_6$): δ 12.67 (s, 1H, COOH), 9.17 (t, J=5.9 Hz, 1H, $Ph_2$-OCNH), 8.05-7.41 (m, 9H, OCNH-$Ph_1$+$Ph_1$-OCNH—$CH_2$-$Ph_2$+$Ph_1$-CH), 4.69 (d, J=5.2 Hz, 2H, $Ph_1$-OCNH—$CH_2$), 2.55-2.33 (m, 2H, CH—C—$CH_2$), 1.6-1.42 (m, 2H, C—$CH_2$—$CH_2$), 0.91 (t, J=7.7 Hz, 3H, $CH_2$—$CH_2$—$CH_3$) ppm; $^{13}$C-NMR (DMSO-$d_6$): 168.9, 166, 138.5, 137.5, 137.4, 136.8, 135.1, 133.8, 133.5, 132.7, 129.3, 129, 128.5, 128.2, 127.6, 127.3, 125.9, 42.1, 29, 18.4, 14 ppm; HRMS: measured m/z 392.1471 (theoretical: 392.1468).

(E)-4-[N-((2-Trifluoromethyl)benzyl)benzamide]-alpha-phenylcinnamic acid (19d)

Yield: 0.02 g (17%); $^1$H NMR (DMSO-$d_6$): δ 8.94 (t, J=5.8 Hz, 1H, $Ph_2$-OCNH), 7.79-6.91 (m, 14H, OCNH-$Ph_1$+$Ph_1$-OCNH—$CH_2$-$Ph_2$+$Ph_1$-CH+C-$Ph_4$), 4.54 (d, J=5.5 Hz, 2H, $Ph_1$-OCNH—$CH_2$) ppm; $^{13}$C-NMR (DMSO-$d_6$): 166.2, 155.5, 129.6, 129.2, 129, 128.9, 128.3, 128.2, 128.1, 128, 128, 128, 127.5, 127.2, 126.9, 126.2, 125.8, 125.8, 126.1, 126, 125.3, 125, 124.6, 41 ppm; HRMS: measured m/z 426.1309 (theoretical: 426.1312).

2-Ethyl 3-[4-(N-((2-trifluoromethyl)benzyl)benzamide)]propionic acid (1c)

Yield: 0.06 g (60%); $^1$H NMR (DMSO-$d_6$): δ 12.2 (s, COOH), 9.1 (t, J=5.9 Hz, 1H, $Ph_2$-OCNH), 7.93-7.36 (m, 8H, OCNH-$Ph_1$+$Ph_1$-OCNH—$CH_2$-$Ph_2$), 4.72 (d, 2H, J=5.6 Hz, $Ph_1$-OCNH—$CH_2$), 2.98-2.78 (m, 2H, $CH_2$—CH—$CH_2$), 2.59-2.5 (m, 1H, $Ph_1$-$CH_2$—CH), 1.64-1.53 (m, $Ph_1$-$CH_2$), 0.94 (t, J=7.4 Hz, CH—$CH_2$—$CH_3$) ppm. $^{13}$C-NMR (DMSO-$d_6$): 177.6, 168.9, 144.1, 137.1, 132.1, 131.9, 128.8, 128.1, 127, 127.4, 125.7, 125.6, 125.5, 125.4, 122.8, 49, 39.8, 37.6, 24.9, 10.5 ppm; HRMS: m/z 380.1469 (theoretical: 380.1468).

2-Ethyl 3-[4-(N-benzylbenzamide)]propionic acid (2c)

Yield: 0.05 g (55%); $^1$H NMR (Methanol-$d_3$): δ 7.83-6.92 (m, 9H, OCNH-$Ph_1$+$Ph_1$-OCNH—$CH_2$-$Ph_2$), 4.46 (s, 2H, $Ph_1$-OCNH—$CH_2$), 2.89-2.67 (m, 2H, $Ph_1$-$CH_2$), 2.51-2.42 (m, 1H, $Ph_1$-$CH_2$—CH), 1.62-1.39 (m, 2H, $Ph_1$-$CH_2$—CH—$CH_2$), 0.85 (t, J=7.6, 3H, CH—$CH_2$—$CH_3$) ppm;

$^{13}$C-NMR (Methanol-$d_3$): 178.2, 168.7, 144.1, 138.9, 132.1, 128.8, 128.8, 128.1, 128.1, 127.1, 127.1, 127, 127, 126.7, 49.5, 43.1, 37.8, 25.2, 10.7 ppm; HRMS: measured m/z 312.1601 (theoretical: 312.1594).

2-Ethyl 3-[4-(N-((2-methyl)benzyl)benzamide)]propionic acid (3c)

Yield: 0.02 g (20%); $^1$H NMR (Methanol-$d_3$): δ 8.01-7.03 (m, 8H, OCNH-$Ph_1$+$Ph_1$-OCNH—$CH_2$-$Ph_2$), 4.47 (s, 2H, $Ph_1$-OCNH—$CH_2$), 2.91-2.69 (m, 2H, $Ph_1$-$CH_2$), 2.55-2.45 (m, 1H, $Ph_1$-$CH_2$—CH), 2.26 (s, 3H, $Ph_2$-$CH_3$), 1.63-1.42 (m, 2H, $Ph_1$-$CH_2$—CH—$CH_2$), 0.86 (t, J=7.4, 3H, CH—$CH_2$—$CH_3$) ppm; $^{13}$C-NMR (DMSO-$d_6$): 176.1, 167.3, 166.1, 145.1, 143.2, 137.3, 135.6, 132.3, 129.8, 129.3, 129, 128.7, 127.3, 126.6, 125.6, 48.1, 37.2, 24.7, 18.5, 11.4 ppm; HRMS: measured m/z 326.1752 (theoretical: 326.1751).

2-Ethyl 3-[4-(N-((2-chloro)benzyl)benzamide)]propionic acid (4c)

Yield: 0.05 g (50%); $^1$H NMR (Methanol-$d_3$): δ 7.68-7.1 (m, 8H, OCNH-$Ph_1$+$Ph_1$-OCNH—$CH_2$-$Ph_2$), 4.46 (s, 2H, $Ph_1$-OCNH—$CH_2$), 2.89-2.69 (m, 2H, $Ph_1$-$CH_2$), 2.54-2.44 (m, 1H, $Ph_1$-$CH_2$—CH), 1.63-1.41 (m, 2H, $Ph_1$-$CH_2$—CH—$CH_2$), 0.86 (t, J=7.6, 3H, CH—$CH_2$—$CH_3$) ppm; $^{13}$C-NMR (Methanol-$d_3$): 177.6, 168.7, 143.8, 138.9, 132.2, 128.8, 128.8, 128.1, 128.1, 127.1, 127, 126.9, 126.8, 126.5, 49, 43.1, 37.5, 25, 10.6 ppm; HRMS: measured m/z 346.1206 (theoretical: 346.1205).

2-Ethyl 3-[4-(N-((2-bromo)benzyl)benzamide)]propionic acid (5c)

Yield: 0.05 g (51%); $^1$H NMR (DMSO-$d_6$): δ 12.12 (s, 1H, COOH), 8.96 (t, J=6.1 Hz, 1H, $Ph_2$-OCNH), 7.81-7.19 (m, 8H, OCNH-$Ph_1$+$Ph_1$-OCNH—$CH_2$-$Ph_2$), 4.46 (d, J=6.1, 2H, $Ph_1$-OCNH—$CH_2$), 2.9-2.71 (m, 2H, $Ph_1$-$CH_2$), 2.6-2.5 (m, 1H, $Ph_1$-$CH_2$—CH), 1.6-1.41 (m, 2H, $Ph_1$-$CH_2$—CH—$CH_2$), 0.87 (t, J=7.6, 3H, CH—$CH_2$—$CH_3$) ppm; $^{13}$C-NMR (DMSO-$d_6$): 176.4, 166.5, 143.7, 140.2, 132.7, 129.2, 128.7, 128.1, 128.1, 127.7, 127.6, 126.9, 126.8, 126.5, 48.5, 40.5, 39.7, 25.1, 11.9 ppm; HRMS: measured m/z 390.07 (theoretical: 390.0699).

2-Ethyl 3-[4-(N-((2-trifluoromethoxy)benzyl)benzamide)]propionic acid (6c)

Yield: 0.07 g (66%); $^1$H NMR (DMSO-$d_6$): δ 12.18 (s, 1H, COOH), 9.03 (t, J=6 Hz, 1H, $Ph_2$-OCNH), 7.88-7.26 (m, 8H, OCNH-$Ph_1$+$Ph_1$-OCNH—$CH_2$-$Ph_2$), 4.53 (d, J=6, 2H, $Ph_1$-OCNH—$CH_2$), 2.96-2.76 (m, 2H, $Ph_1$-$CH_2$), 2.63-2.59 (m, 1H, $Ph_1$-$CH_2$—CH), 1.64-1.5 (m, 2H, $Ph_1$-$CH_2$—CH—$CH_2$), 0.9 (t, J=7.6, 3H, CH—$CH_2$—$CH_3$) ppm; $^{13}$C-NMR (DMSO-$d_6$): 177.5, 176.4, 166.5, 143.7, 140.2, 133.1, 132.7, 129.2, 129, 128.7, 127.7, 127.6, 127.1, 126.8, 126.5, 48.5, 40.3, 39.1, 26.5, 11.9 ppm; HRMS: measured m/z 396.1417 (theoretical: 396.1417).

2-Ethyl 3-[4-(N-((4-fluoro)benzyl)benzamide)]propionic acid (7c)

Yield: 0.05 g (50%); $^1$H NMR (Methanol-$d_3$): δ 7.68-6.91 (m, 8H, OCNH-$Ph_1$+$Ph_1$-OCNH—$CH_2$-$Ph_2$), 4.43 (s, 2H, $Ph_1$-OCNH—$CH_2$), 2.89-2.69 (m, 2H, $Ph_1$-$CH_2$), 2.54-2.44 (m, 1H, $Ph_1$-$CH_2$—CH), 1.62-1.41 (m, 2H, $Ph_1$-$CH_2$—CH—$CH_2$), 0.86 (t, J=7.4, 3H, CH—$CH_2$—$CH_3$) ppm; $^{13}$C-NMR (Methanol-$d_3$): 177.6, 168.7, 163.7, 160.5, 143.9, 135, 135, 132.1, 129.1, 129, 129, 127, 114.9, 114.6, 49.1, 42.4, 37.6, 25, 10.6 ppm; HRMS: measured m/z 330.1503 (theoretical: 330.15).

2-Ethyl 3-[4-(N-((4-trifluoromethyl)benzyl)benzamide)]propionic acid (8c)

Yield: 0.05 g (53%); $^1$H NMR (Methanol-$d_3$): δ 7.7-7.1 (m, 8H, OCNH-$Ph_1$+$Ph_1$-OCNH—$CH_2$-$Ph_2$), 4.61 (s, 2H, $Ph_1$-OCNH—$CH_2$), 3.03-2.82 (m, 2H, $Ph_1$-$CH_2$), 2.66-2.56 (m, 1H, $Ph_1$-$CH_2$—CH), 1.76-1.53 (m, 2H, $Ph_1$-$CH_2$—CH—$CH_2$), 0.99 (t, J=8.3, 3H, CH—$CH_2$—$CH_3$) ppm; $^{13}$C-NMR (Methanol-$d_3$): 177.5, 168.8, 144, 132.5, 132.2, 132.1, 131.1, 129.1, 129, 127.5, 127, 125, 125, 124.9, 124.6, 49, 47.4, 37.5, 25, 10.6 ppm; HRMS: measured m/z 380.1467 (theoretical: 380.1468).

2-Ethyl 3-[4-(N-((4-trifluoromethoxy)benzyl)benzamide)]propionic acid (9c)

Yield: 0.06 g (60%); $^1$H NMR (Methanol-$d_3$): δ 7.82-7.24 (m, 8H, OCNH-$Ph_1$+$Ph_1$-OCNH—$CH_2$-$Ph_2$), 4.61 (s, 2H, $Ph_1$-OCNH—$CH_2$), 3.03-2.82 (m, 2H, $Ph_1$-$CH_2$), 2.66-2.56 (m, 1H, $Ph_1$-$CH_2$—CH), 1.76-1.53 (m, 2H, $Ph_1$-$CH_2$—CH—$CH_2$), 0.99 (t, J=8.3, 3H, CH—$CH_2$—$CH_3$) ppm; $^{13}$C-NMR (Methanol-$d_3$): 178, 175.6, 168.7, 148.1, 144.1, 138.3, 132, 128.8, 128.7, 128.5, 127, 125.3, 125.2, 125.1, 120.7, 49.3, 47, 37.6, 25, 10.6 ppm; HRMS: measured m/z 396.1416 (theoretical: 396.1417).

2-Ethyl 3-[4-(N-((4-methoxy)benzyl)benzamide)]propionic acid (10c)

Yield: 0.06 g (62%); $^1$H NMR (DMSO-$d_6$): δ 12.19 (s, 1H, COOH), 8.95 (t, J=6.7 Hz, 1H, $Ph_2$-OCNH), 7.86-6.91 (m, 8H, OCNH-$Ph_1$+$Ph_1$-OCNH—$CH_2$-$Ph_2$), 4.45 (d, J=5.8, 2H, $Ph_1$-OCNH—$CH_2$), 3.78 (s, 3H, $Ph_2$-O—$CH_3$), 2.96-2.77 (m, 2H, $Ph_1$-$CH_2$), 2.63-2.6 (m, 1H, $Ph_1$-$CH_2$—CH), 1.64-1.49 (m, 2H, $Ph_1$-$CH_2$—CH—$CH_2$), 0.93 (t, J=7.6, 3H, CH—$CH_2$—$CH_3$) ppm; $^{13}$C-NMR (DMSO-$d_6$): 176.4, 166.4, 158.6, 143.6, 132.8, 132.2, 129.1, 129, 127.6, 127, 125.3, 125.2, 125.1, 114.1, 55.5, 42.4, 40.8, 37.5, 25.1, 11.9 ppm; HRMS: measured m/z 342.17 (theoretical: 342.17).

2-Ethyl 3-[4-(N-((4-chloro)benzyl)benzamide)]propionic acid (11c)

Yield: 0.05 g (50%); $^1$H NMR (DMSO-$d_6$): δ 12.13 (s, 1H, COOH), 8.97 (t, J=6 Hz, 1H, $Ph_2$-OCNH), 7.83-7.27 (m, 8H, OCNH-$Ph_1$+$Ph_1$-OCNH—$CH_2$-$Ph_2$), 4.53 (d, J=6.4, 2H, $Ph_1$-OCNH—$CH_2$), 2.9-2.71 (m, 2H, $Ph_1$-$CH_2$), 2.57-2.52 (m, 1H, $Ph_1$-$CH_2$—CH), 1.58-1.43 (m, 2H, $Ph_1$-$CH_2$—CH—$CH_2$), 0.88 (t, J=7.1, 3H, CH—$CH_2$—$CH_3$) ppm; $^{13}$C-NMR (DMSO-$d_6$): 176.4, 166.7, 146.6, 143.9, 132.4, 132.4, 129.6, 129.2, 129.1, 128, 127.7, 125.2, 125.1, 121.1, 48.5, 39.4, 37.5, 25.1, 11.9 ppm; HRMS: measured m/z 346.1206 (theoretical: 346.1205).

2-Ethyl 3-[4-(N-((4-phenoxy)benzyl)benzamide)]propionic acid (12c)

Yield: 0.03 g (30%); $^1$H NMR (Methanol-$d_3$): δ 7.69-6.82 (m, 13H, OCNH-$Ph_1$+$Ph_1$-OCNH—$CH_2$-$Ph_2$), 4.44 (s, 2H, $Ph_1$-OCNH—$CH_2$), 2.89-2.69 (m, 2H, $Ph_1$-$CH_2$), 2.54-2.44

(m, 1H, $Ph_1$-$CH_2$—CH), 1.62-1.41 (m, 2H, $Ph_1$-$CH_2$—CH—$CH_2$), 0.85 (t, J=7.6, 3H, CH—$CH_2$—$CH_3$) ppm; $^{13}$C-NMR (Methanol-$d_3$): 177.5, 168.6, 157.4, 156.4, 133.9, 132.4, 132.2, 129.4, 128.8, 128.7, 127, 126.9, 126.8, 125.3, 123.1, 122.9, 121.5, 118.5, 118.3, 118, 47.6, 42.2, 37.5, 25, 10.6 ppm; HRMS: measured m/z 404.1858 (theoretical: 404.1856).

2-Ethyl 3-[4-(N-(4-fluoro(2-trifluoromethyl)benzyl) benzamide)]propionic acid (13c)

Yield: 0.05 g (50%); $^1$H NMR (Methanol-$d_3$): δ 7.84-7.18 (m, 7H, OCNH-$Ph_1$+$Ph_1$-OCNH—$CH_2$-$Ph_2$), 4.64 (s, 2H, $Ph_1$-OCNH—$CH_2$), 2.91-2.71 (m, 2H, $Ph_1$-$CH_2$), 2.55-2.45 (m, 1H, $Ph_1$-$CH_2$—CH), 1.64-1.42 (m, 2H, $Ph_1$-$CH_2$—CH—$CH_2$), 0.86 (t, J=7.6, 3H, CH—$CH_2$—$CH_3$) ppm; $^{13}$C-NMR (Methanol-$d_3$): 177.5, 168.9, 159.7, 144.8, 143.1, 133.1, 131.8, 131, 131, 128.8, 127.1, 118.8, 118.6, 112.9, 112.9, 60, 46.7, 37.5, 25, 10.6 ppm; HRMS: measured m/z 398.137 (theoretical: 398.1374).

2-Ethyl 3-[4-(N-(4-methoxy(2-trifluoromethyl)benzyl)benzamide)]propionic acid (14c)

Yield: 0.7 g (79%); $^1$H NMR (DMSO-$d_6$): δ 12.15 (s, $CH_2$—CH—COOH), 8.97 (t, J=5.6 Hz, 1H, $Ph_2$-OCNH), 7.87-7.2 (m, 8H, OCNH-$Ph_1$+$Ph_1$-OCNH—$CH_2$-$Ph_2$), 4.58 (d, 2H, J=5.5, $Ph_1$-OCNH—$CH_2$), 3.81 (s, 3H, $Ph_2$-O—$CH_3$), 2.94-2.72 (m, 2H, $CH_2$—CH—$CH_2$), 2.9-2.72 (m, 1H, $Ph_1$-$CH_2$—CH), 1.57-1.46 (m, $Ph_1$-$CH_2$), 0.9 (t, J=7.5 Hz, CH—$CH_2$—$CH_3$) ppm. $^{13}$C-NMR (DMSO-$d_6$): 176.8, 166.8, 158.5, 144.3, 132.4, 130.8, 129.6, 129.3, 128, 127.8, 127.4, 126.5, 122.8, 118.2, 112.1, 56.3, 50.5, 48.4, 37.5, 25.1, 11.8 ppm; HRMS: m/z 410.1572 (theoretical: 410.1573).

2-Ethyl 3-[13-(N-((2-trifluoromethyl)benzyl)benzamide)]propionic acid (15c)

Yield: 0.06 g (60%); $^1$H NMR (DMSO-$d_6$): δ 12.15 (s, COOH), 9.13 (t, J=5.5 Hz, 1H, $Ph_2$-OCNH), 7.85-7.43 (m, 8H, OCNH-$Ph_1$+$Ph_1$-OCNH—$CH_2$-$Ph_2$), 4.72 (d, 2H, J=5.1 Hz, $Ph_1$-OCNH—$CH_2$), 2.99-2.78 (m, 2H, $CH_2$—CH—$CH_2$), 2.66-2.6 (m, 1H, $Ph_1$-$CH_2$—CH), 1.66-1.5 (m, $Ph_1$-$CH_2$), 0.95 (t, J=7.3 Hz, CH—$CH_2$—$CH_3$) ppm. $^{13}$C-NMR (DMSO-$d_6$): 176.5, 167, 140.5, 138.2, 134.4, 133.1, 132.4, 128.7, 128.7, 128.2, 127.7, 126.2, 126.1, 125.6, 122.8, 48.7, 39.4, 37.6, 25.1, 11.9 ppm, HRMS: measured m/z 380.1473 (theoretical: 380.1468).

3-[4-(N-((2-trifluoromethyl)benzyl)benzamide)]propionic acid (16c)

Yield: 0.05 g (50%); $^1$H NMR (DMSO-$d_6$): δ 12.21 (s, 1H, COOH), 9.04 (t, J=6.8 Hz, 1H, OCNH), 7.86-7.34 (m, 8H, OCNH-$Ph_1$+$Ph_1$-OCNH—$CH_2$-$Ph_2$), 4.65 (d, J=5.6 Hz, 2H, $Ph_1$-OCNH—$CH_2$), 2.88 (t, J=8, 2H, $Ph_1$-$CH_2$), 2.57 (t, J=8.6 Hz, 2H, $Ph_1$-$CH_2$—$CH_2$) ppm; $^{13}$C-NMR (DMSO-$d_6$): 174, 166.7, 145, 138.3, 135.4, 133.1, 132.2, 129.7, 129.1, 128.8, 127.8, 126.3, 125.5, 125.4, 123.4, 50.7, 39.8, 35.5 ppm; HRMS: measured m/z 352.1156 (theoretical: 352.1155).

2-Methyl 3-[4-(N-((2-trifluoromethyl)benzyl)benzamide)]propionic acid (17c)

Yield: 0.05 g (50%); $^1$H NMR (DMSO-$d_6$): δ 12.17 (s, 1H, COOH), 9.04 (t, J=6.2 Hz, 1H, OCNH), 7.86-7.3 (m, 8H, OCNH-$Ph_1$+$Ph_1$-OCNH—$CH_2$-$Ph_2$), 4.65 (d, J=6.6 Hz, 2H, $Ph_1$-OCNH—$CH_2$), 3-2.9 (m, 1H, $Ph_1$-$CH_2$—CH), 2.73-2.64 (m, 2H, $Ph_1$-$CH_2$), 1.05 (d, J=6.4, 3H, $CH_2$—CH—$CH_3$) ppm; $^{13}$C-NMR (DMSO-$d_6$): 177.1, 166.7, 143.9, 140.5, 133.2, 132.4, 131.5, 129.4, 129.3, 128.6, 127.7, 126.5, 125.4, 125.4, 124.8, 50.7, 40.8, 39.1, 17.2 ppm; HRMS: measured m/z 366.1314 (theoretical: 366.1312).

2-Propyl 3-[4-(N-((2-trifluoromethyl)benzyl)benzamide)]propionic acid (18c)

Yield: 0.02 g (20%); $^1$H NMR (DMSO-$d_6$): δ 12.47 (s, 1H, CCOH), 9.04 (t, J=4.7 Hz, 1H, OCNH), 7.85-7.29 (m, 8H, OCNH-$Ph_1$+$Ph_1$-OCNH—$CH_2$-$Ph_2$), 4.65 (d, J=5.5 Hz, 2H, $Ph_1$-OCNH—$CH_2$), 2.91-2.71 (m, 2H, $Ph_1$-$CH_2$), 2.65-2.45 (m, 1H, $Ph_1$-$CH_2$—CH), 1.59-1.2 (m, 4H, $Ph_1$-$CH_2$—CH—$CH_2$+$CH_2$—CH—$CH_2$—$CH_2$), 1.35-0.85 (t, J=7.1 Hz, 3H, CH—$CH_2$—$CH_2$—$CH_3$) ppm; $^{13}$C-NMR (DMSO-$d_6$): 176.6, 167.1, 144, 138.4, 133.2, 132.4, 131.5, 129.4, 129.2, 128.1, 127.7, 126.2, 125.9, 125.4, 124.9, 38, 34.6, 34.1, 20.3, 14.5 ppm; HRMS: measured m/z 394.1623 (theoretical: 394.1625).

2-Phenyl 3-[4-(N-((2-trifluoromethyl)benzyl)benzamide)]propionic acid (19c)

Yield: 0.2 g (16%); $^1$H NMR (DMSO-$d_6$): δ 12.47 (s, 1H, COOH), 9.08 (t, J=6.9 Hz, 1H, OCNH), 7.87-7.27 (m, 13H, OCNH-$Ph_1$+$Ph_1$-OCNH—$CH_2$-$Ph_2$+$CH_2$—CH-$Ph_4$), 4.7 (d, J=5.4 Hz, 2H, $Ph_1$-OCNH—$CH_2$), 3.45-3.05 (m, 2H, $Ph_1$-$CH_2$), 4 (t, J=7.8, 1H, $Ph_1$-$CH_2$—CH) ppm; $^{13}$C-NMR (DMSO-$d_6$): 174.7, 166.9, 143.7, 139.4, 138.2, 138.1, 133.2, 132.2, 129.3, 128.8, 128.6, 128.3, 127.7, 127.7, 127.7, 126.6, 126.5, 126.6, 126.2, 126.1, 125.7, 125, 124.6, 52.7 ppm; HRMS: measured m/z 428.1465 (theoretical: 428.1468).

(E)-N-Methoxy-N-methyl 3-[4-(N-((2-trifluoromethyl)benzyl)benzamide)]but-2-enamide (20)

To a solution of 1 g (3.3 mmol) 4-formyl-N-(2-(trifluoromethyl)benzyl)benzamide (1) in 20 ml chloroform under argon atmosphere was added 1.3 g (3.6 mmol) N-Methoxy-N-methyl(triphenylphosphoranylidene)acetamide. After 16 h the solvent was evaporated under reduced pressure. The crude product was purified by flash chromatography with solvent mixture of EE/Hex in the ratio 1:1. A white solid remained as pure product. Yield: 0.6 g (47%); $^1$H NMR (DMSO-$d_6$): δ 9.2 (t, J=5.8 Hz, 1H, $Ph_1$-OCNH), 8-7.2 (m, 10H, OCNH-$Ph_1$+OCNH—$CH_2$-$Ph_2$+$Ph_1$-CH+$Ph_1$-CH—CH), 4.7 (d, J=5.4 Hz, 2H, $Ph_1$-OCNH—$CH_2$), 3.78 (s, 3H, OCN—O—$CH_3$), 3.25 (s, 3H, OCN—$CH_3$) ppm. MS-ESI: m/z 393 [M+$H^+$].

N-Methoxy-N-methyl 3-[4-(N-((2-trifluoromethyl) benzyl)benzamide)]cyclopropanecarboxamide (21)

To a solution of 561 mg (2.6 mmol) trimethylsulfoniumiodide in 3.15 ml dry DMSO under argon atmosphere was added 97 mg (2.55 mmol) NaH in small portions. After the reaction mixture was stirred for 1 h, a solution of 500 mg (1.3 mmol) (E)-N-methoxy-N-methyl 3-[4-(N-((2-trifluoromethyl)benzyl)benzamide)]but-2-enamide (20) in 1.05 ml dry DMSO was injected. The reaction was quenched with 10 ml saturated $NH_4Cl$ solution after 6 h. The product was extracted three times with 5 ml DCM. The collected organic layers were washed once with 4 ml brine and dried over $MgSO_4$. The solvent was removed under reduced pressure. The pure product was recrystallized from a EE/Hex mixture and occurred as white solid. Yield: 0.62 g (60%); $^1$H NMR (DMSO-$d_6$): δ 9.06 (t, J=5.4 Hz, 1H, OCNH), 7.88-7.31 (m, 8H, OCNH-$Ph_1$+$Ph_1$-OCNH—$CH_2$-$Ph_2$), 4.67 (d, J=5.4 Hz, 2H, $Ph_1$-OCNH—$CH_2$), 3.66 (s, 3H, OCN—O—$CH_3$), 3.16 (s, 3H, OCN—$CH_3$), 2.57-2.36 (m, 2H, $Ph_1$-CH+$Ph_1$-CH—CH), 1.54-1.4 (m, 2H, $Ph_1$-CH—$CH_2$) ppm; $^{13}$C-NMR (DMSO-$d_6$): 167.4, 143.8, 135.7, 130.8, 130.6, 126.9, 126.4, 126.2, 126.1, 125.7, 124.6, 124.3, 123, 122.3, 122, 38.5, 37.4, 32, 27.8, 24, 20.6 ppm; HRMS: measured m/z 407.1578 (theoretical: 407.1577).

2-[4-(N-((2-trifluoromethyl)benzyl)benzamide)]cyclopropan carboxylic acid (22)

To solution of 100 mg (0.25 mmol) N-methoxy-N-methyl 3-[4-(N-((2-trifluoromethyl)benzyl)benzamide)]cyclopropanecarboxamide (21) in 3 ml EtOH was added 3 ml KOH solution (10%). The reaction mixture was refluxed for 24 h. EtOH was removed from the reaction solution under reduced pressure and the remaining aqueous solution was washed three times with DEE. The aqueous solution pH was adjusted at 1 with 12 M HCl solution. The pure white product precipitated and was collected by filtration. Yield: 0.05 g (55%); $^1$H NMR (DMSO-$d_6$): δ 12.27 (s, 1H, COOH), 8.99 (t, J=5.4 Hz, 1H, OCNH), 7.8-7.2 (m, 8H, OCNH-$Ph_1$+$Ph_1$-OCNH—$CH_2$-$Ph_2$), 4.59 (d, J=5.5 Hz, 2H, $Ph_1$-OCNH—$CH_2$), 2.3-2.4 (m, 1H, $Ph_1$-CH), 1.86-1.8 (m, 1H, $Ph_1$-CH—CH), 1.44-1.31 (m, 2H, $Ph_1$-CH—$CH_2$) ppm; $^{13}$C-NMR (DMSO-$d_6$): 173.7, 166.2, 144.2, 137.7, 137.1, 132.6, 132.2, 131.8, 128.1, 128, 127.4, 127.3, 125.9, 125.9, 125.8, 39.7, 37.4, 25.1, 24.5 ppm; HRMS: measured m/z 364.1158 (theoretical: 364.1155).

4-[N-(2-(trifluoromethyl)benzyl))benzamid]-(E)-4-methyl(o-(benzylhydroxyl)imin) (23)

250 mg (0.8 mmol) 4-formyl-N-(2-(trifluoromethyl)benzyl)benzamid (1), 195 mg (1.2 mmol) o-benzylhydroxylamine hydrochloride and 213 μL (1.2 mmol) DIPEA were solved in 4 ml MeOH and stirred for 12 h. The solvent was evaporated under reduced pressure and the crude product was recrystallized from a EE/Hex mixture. A white solid remained as pure product. Yield: 0.25 g (74%); $^1$H NMR (DMSO-$d_6$): δ 9.17 (t, J=5.5 Hz, 1H, OCNH), 8.37 (s, 1H, $Ph_1$-CH), 7.98-7.29 (m, 13H, OCNH-$Ph_1$+$Ph_1$-OCNH—$CH_2$-$Ph_2$+$Ph_1$-CH—N—O—$CH_2$-$Ph_5$), 5.2 (s, 2H, $Ph_1$-CH—N—O—$CH_2$), 4.65 (d, J=5.7 Hz, 2H, $Ph_1$-OCNH—$CH_2$) ppm; $^{13}$C-NMR (DMSO-$d_6$): 166, 137.4, 135, 135, 132.7, 131.5, 128.6, 128.4, 128.3, 128.2, 127.9, 127.6, 127.4, 127.3, 126.8, 126.6, 126.3, 126.1, 126, 125.9, 125.7, 125, 124.6, 50 ppm; HRMS: measured m/z 413.1473 (theoretical: 413.1471).

General Procedure for the Preparation of the Compounds 25 & 26, Using the Example of 4-[N-(2-(trifluoromethyl)benzyl))benzamide]-(1,1'-biphenyl)-4-acid (25)

250 mg (1.5 mmol) 4-carboxybenzenboronic acid, 555 mg (1.4 mmol) 4-Iodo-[N-(2-(trifluoromethyl)benzyl))benzamid] (24), 9.2 mg (0.04 mmol) palladium(II)acetat and 568 mg (4.1 mmol) $K_2CO_3$ were solved in a mixture of acetone/$H_2O$ in the ratio 1:1. The reaction was stirred for 1 h at 65° C. The mixture was then filtered through celite and acetone was evaporated under reduced pressure. After acidifying the aqueous layer with 12 M HCl solution the product precipitated. A white solid remained and no further purification was needed. Yield: 0.36 g (66%); $^1$H NMR (DMSO-$d_6$): δ 13.03 (s, 1H, COOH), 9.21 (t, J=6.1 Hz, 1H, OCNH), 8.09-7.48 (m, 12H, OCNH-$Ph_1$+$Ph_1$-OCNH—$CH_2$-$Ph_2$+$Ph_1$-$Ph_7$), 4.71 (d, J=5.5 Hz, 2H, $Ph_1$-OCNH—$CH_2$) ppm; $^{13}$C-NMR (DMSO-$d_6$): 167, 166, 162.4, 143.2, 142.1, 141.8, 137.9, 134.7, 133.5, 132.7, 130.2, 130, 128.9, 128.2, 127.4, 127.3, 127.1, 127.1, 127, 125.1, 125, 48.1 ppm; HRMS: measured m/z 400.1156 (theoretical: 400.1155).

4-[N-(2-(trifluoromethyl)benzyl))benzamide]-(1,1'-biphenyl)-3-carboxylic acid (26)

Yield: 0.37 g (67%); $^1$H NMR (DMSO-$d_6$): δ 13.08 (s, 1H, COOH), 9.14 (t, J=5.7 Hz, 1H, OCNH), 8.2-7.39 (m, 12H, OCNH-$Ph_1$+$Ph_1$-OCNH—$CH_2$-$Ph_2$+$Ph_1$-$Ph_7$), 4.63 (d, J=5.5 Hz, 2H, $Ph_1$-OCNH—$CH_2$) ppm; $^{13}$C-NMR (DMSO-do): 168.1, 166, 144, 143.1, 142.1, 140.8, 136.8, 134.8, 133.4, 132.9, 130, 130, 128.8, 128.1, 127.7, 127.5, 127.1, 126.1, 126, 125.1, 124, 49.1 ppm; HRMS: measured m/z 400.1155 (theoretical: 400.1155).

[N-(2-(Trifluoromethyl)benzyl)benzamid]-4-(1H-tetrazole) (28)

100 mg (0.3 mmol) 4-cyano-[N-(2-(trifluoromethyl)benzyl))benzamide] (27), 43 mg (0.7 mmol) NaN3 and 23 mg (0.4 mmol) $NH_4Cl$ were solved in 2 ml dry DMF under argon atmosphere and stirred for 12 h at 150° C. After the reaction mixture reached room temperature 1 ml $H_2O$ was added. To the aqueous layer 12 M HCl solution was added and the product precipitated. Through filtration the slightly yellow solid, which did not need further purification, was collected. Yield: 0.11 g (92%); $^1$H NMR (DMSO-$d_6$): δ 9.35 (t, J=5.6 Hz, 1H, OCNH), 8.25-7.54 (m, 8H, OCNH-$Ph_1$+$Ph_1$-OCNH—$CH_2$-$Ph_2$), 4.76 (d, J=5.6 Hz, 2H, $Ph_1$-OCNH—$CH_2$) ppm; $^{13}$C-NMR (DMSO-$d_6$): 166.6, 160.3, 137.9, 136.9, 135.5, 132.7, 132.3, 129.2, 128.6, 128.2, 127.7, 127.2, 126.7, 125.5, 125.1, 125, 48.2 ppm; HRMS: measured m/z 348.1067 (theoretical: 348.1067).

sEH Activity Assay

The $IC_{50}$ values of the compounds were determined by a fluorescence based assay system of 96-well format. As substrate non-fluorescent PHOME (3-phenyl-cyano-(6-methoxy-2-naphthalenyl)methyl ester-2-oxirane-acetic acid, Cayman Chemicals) was used, which can be hydrolyzed by the sEH to the fluorescent 6-methoxynaphtaldehyde[112]. The formation of the product can be measured ($\lambda_{em}$=330 nm, $\Delta_{ex}$=465 nm) by a Tecan Infinite F200 Pro plate reader. The assay was performed adopted to the literature[67]. Therefore, recombinant human sEH[90] (2 μg/well) in Bis-Tris buffer pH 7 with 0.1 mg/ml BSA containing a final concentration of 0.01% Triton-X 100. 100 μl of protein were incubated with different concentrations of compounds (DMSO with final concentration of 1%) for 30 min. at room temperature. After that 10 μl of substrate were added (final concentration 50 μM). The hydrolysed substrate was measured for 30 min. (one point every minute). A blank control (no protein and no compound) as well as a positive control (no compound) was executed. All measurements were performed in triplicates.

PPAR Activity Assay[113].

Cell Culture

COS-7 cells (PPAR) were grown in DMEM high glucose, supplemented with 10% fetal calf serum (FCS), 1% sodium pyruvate (SP) and 1% penicillin/streptomycin (PS) at 37° C.

and 5% CO2. Used plasmids for PPAR transactivation assay are shown under supporting informations.

PPAR Transactivation Assay

The day before transfection, COS-7 cells were seeded in 96-well plates with a density of 30,000 cells per well. Transient transfection was carried out using Lipofectamine LTX reagent (Invitrogen, Carlsbad, Calif., USA) according to the manufacturer's protocol with pFR-Luc (Stratagene), pRL-SV40 (Promega) and the Gal4-fusion receptor plasmids (pFA-CMV-hPPAR-LBD) of the respective PPAR subtype. 5 h after transfection, medium was changed to DMEM without phenol red and 10% FCS, supplemented with 1% SP, 1% PS and 1% L-glutamine, now additionally containing 0.1% DMSO and the respective test compound or 0.1% DMSO alone as untreated control. Each concentration was tested in triplicate wells and each experiment was repeated independently at least three times. Following overnight incubation with the test compounds, cells were assayed for luciferase activity using Dual-Glo™ Luciferase Assay System (Promega) according to the manufacturer's protocol. Luminescence was measured with an Infinite m200 luminometer (Tecan Deutschland GmbH). Each concentration of the compounds was tested in triplicate wells. Normalization for transfection efficacy and cell growth was done by division of the firefly luciferase data by *renilla* luciferase data resulting in relative light units. Activation factors were obtained by dividing by DMSO control. $EC_{50}$ and standard deviation values were calculated by mean values of at least three determinations by SigmaPlot 2001 (Systat Software GmbH, Erkrath, Germany) using a four-parameter logistic regression. All compounds were evaluated by comparison of the achieved maximum effect to that of the reference compound (pioglitazone for PPARγ, GW7647 for PPARα, and L165041 for PPARδ each with 1 μM). Data are expressed as mean±SE; n≥3.

WST-Cytotoxicity Assay

The WST-1 assay (Roche Diagnostic GmbH, Mannheim, Germany) was used to determine the cell viability after treatment with the compounds. For this purpose, Hela and HepG2 cells were seeded each in 96-well plates at a density of $1\times10^4$ per well in DMEM with Phenolred and in prescence of 10% FCS. After 24 hours the medium was changed. Fresh DMEM with 10% FCS was added and the cells were treated with the compounds for 48 hours. Cell viability was assessed according to the manufacturer's protocol using a microplate reader (infinity M200, Tecan Group Ltd., Crailsheim, Germany). All experiments were performed at least in triplicate.

Water Solubility Approximation

PBS at pH 7.4 with 0.01% Polysorbate 20 (Tween) was combined with 1% of a DMSO solution of the inquired compound in a 96-well transparent flat bottom microtiter plate. Precipitation of the compound was measured at 650 nm with a Tecan Infinite 200 (Tecan Group Ltd, Mannedorf, Switzerland).

In Vitro Drug Metabolism in Rat Liver Microsomes

A solution of the test compound (1 mM) was prepared in 100% DMSO. 432 μl phosphate buffer (0.1 M, pH 7.4) together with 50 μl NADPH-regenerating system (30 mM glucose-6-phosphate, 4 U/ml glucose-6-phosphate dehydrogenase, 10 mM NADP, 30 mM $MgCl_2$) and 5 μl of the corresponding test compound were pre-incubated at 37° C. The final concentration of the investigated compound is 10 μM. After 5 min the reaction was started by the addition of 13 μl microsome mix from the liver of Sprague-Dawley rats (Gibco®, Darmstadt, Germany; 20 mg protein/ml in 0.1 M phosphate buffer). The incubation was performed in a shaking water bath at 37° C. The reaction was stopped by the addition of 500 μl ice-cold methanol at 0, 15, 30 and 60 min. The samples were centrifuged at 10 000 g for 5 min at 4° C. The supernatants were analysed and quantified by HPLC. Control samples were always performed to check the stability of the compounds in the reaction mixture. First control was without NADPH, which is needed for the enzymatic activity of the microsomes. Second control was with inactivated microsomes (microsomes that were incubated for 20 min at 90° C.). Third control was without test compounds (to determine the baseline). As positive control, a solution of 7-ethoxycoumarin (1 mM) was used. The final concentration of the control compound, under assay conditions, was again 10 μM. The amounts of the test compounds were quantified by an external calibration curve.

Differentiation of Murine 3T3-L1 Cells

3T3-L1 cells were subcultured in DMEM containing 10% newborn calf serum in a humidified atmosphere at 37° C., 5% $CO_2$. Cells were differentiated into adipocytes for 14 days according to the method of Zebisch et al.[114]. Briefly, cells were seeded in 6-well plates ($2.5\times10^6$/well). Differentiation was started at day 3 by addition of 1 μg/ml insulin, 0.25 μM dexamethasone and 0.5 mM isobutylmethylxanthine in DMEM supplemented with 10% fetal calf serum. At day 5 medium was replaced by medium containing only insulin for 2 more days. After this, cells were kept for lipid droplet accumulation in basal medium without additions until day 15. Rosiglitazone (2 μM) and N-cyclohexyl-N'-(iodophenyl)urea (CIU) (10 μM) were used as PPARγ and sEH positive controls, respectively. Differentiation of 3T3-L1 cells was confirmed by Oil Red O staining. Cells were washed with PBS and subsequently fixed for 60 minutes with a formaldehyde solution (4% in PBS). After this, cells were rinsed with 60% isopropanol and incubated with Oil Red O solution (0.3%) for 120 minutes.

Quantitative Polymerase Chain Reaction (qPCR)

3T3-L1 cells or homogenized mouse tissues were lysed using TRIzol® reagent (Ambion, life technologies, Carlsbad, USA) and mRNA was isolated following the manufacturers protocol. DNA contaminations were digested using DNAse (DNase I, RNase-free Kit; Thermo Scientific, Waltham, USA) and mRNA concentrations were measured with a NANODROP2000 spectrophotometer (Thermo Scientific, Waltham, USA). Subsequently, reverse transcription was performed using the High Capacity RNA-to-cDNA Kit (Applied Biosystems, Foster City, USA). PCR was performed using specific primers for GLUT-4, FABP-4, LPL, adiponectin and CD36 (shown under supporting informations) with a StepOnePlus Real-Time PCR System (Applied Biosystems, Foster City, USA). NoNo (3T3-L1) and β-Actin (mouse tissue) were used as reference genes. All samples were measured in triplicates and were analyzed using the ΔΔCT method.

Both mouse PK studies were performed by Pharmacelsus GmbH (Saarbrucken, Germany), a commercial research organization, and are described under supporting informations. The sEH PD data was generated through determination of epoxyeicosatrienoicacids (EETs) and their metabolites dihydroxyepoxyeicosatrienoicacids (DHETs) by LC/MS-MS[115]. The used method and instrumental details are described under supporting informations.

Abbreviations

ABCA1, ATP binding cassette transporter 1; ADME, absorption, distribution, metabolism, and excretion; AMI, acute myocardial infarction; aP2, human adipocyte fatty acid binding protein; ASCVD, arteriosclerotic cardiovascular diseases; ATP, adenosintriphosphat; AUC 0→∞, area under the concentration-time curve extrapolated to infinity; bis-tris, 2-[Bis(2-hydroxyethyl)amino]-2-(hydroxymethyl)-1,3-propanediol; —Br, bromine substituent; BSA, bis(trimethylsilyl)acetamide; Bw, body weight; CD36, fatty acid translocase; —$CH_3$, methyl substituent; CIU, N-cyclohexyl-N'-iodophenyl urea; —Cl, chlorine substituent; Cl/f, total body clearance (normalized to bioavailability); $C_{max}$, maximal concentration; CNS, central nervous system; compd., compound; COST, CV-1 (simian) in Origin, and carrying the SV40 genetic material; CVD, cardiovascular diseases; DCM, dichloromethane; DEE, diethyl ether; DHETs, dihydroxyepoxyeicosatrienoic acids; DIPEA, diisopropylethylamine; DMAP, 4-dimethylaminopyridine; DMEM, dulbecco's Modifizierte Medien; DMF, dimethylformamide; DMSO-$d_6$, deuterated dimethyl sulfoxide; DNA, deoxyribonucleic acid; $EC_{50}$, half maximal effective concentration; EDC, 1-ethyl-3-(3-dimethylaminopropyl)carbodiimide; EE, ethylacetat; EETs, epoxyeicosatrienoic acids; $E_{max}$-%, Maximum activation in percent; EPCs, endothelial progenitor cells; ESI, electrospray ionization; EtOH, ethanol; —F, fluorine substituent; FABP4, fatty acid binding protein 4; FATP, fatty acid transporter protein; FCS, fetal calf serum; FFA, free fatty acid; FFA1/GPR40, free fatty acid receptor 1; GLUT-4, glucose transporter type 4; GSIS, Glucose Stimulated Insulin Secretion; GSK1997132B, (R)-1-((3,5-difluoropyridin-2-yl)methyl)-2-methyl-N-(1-phenylpropyl)-1H-benzo[d]imidazole-5-carboxamide; GSK2188931B, (N-({4-bromo-2-[(trifluoromethyl)oxy]phenyl}methyl)-1-[4-methyl-6-(methylamino)-1,3,5-triazin-2-yl]-4-piperidinecarboxamide); GW7647, 2-(4-(2-(1-Cyclohexanebutyl)-3-cyclohexylureido)ethyl)-phenyl-thio)-2-methyl-propionic acid; —H, hydrogen substituent; $H_2O$, water; HCl, hydrochloric acid; HDL, high density lipoprotein; HDL-C, high density lipoprotein cholesterol; HepG2, hepatocyte carcinoma; Hex, hexan; HMG CoA, 3-hydroxy-3-methylglutaryl coenzyme A; HPLC, high-performance liquid chromatography; HRMS, high resolution mass spectrometry; i.a., inactive; IBCF, isobutylchloroformiat; $IC_{50}$, half maximal inhibitory concentration; $K_2CO_3$, potassium carbonate; KCL, (S)-2-(4-methoxy-3-((4-(trifluoromethyl) benzyl)carbamoyl)benzyl)butanoic acid; KOH, potassium hydroxide; L165041, [4-[3-(4-Acetyl-3-hydroxy-2-propylphenoxy)propoxy]phenoxy]acetic acid; LBD, ligand binding domain; LC-MS, liquid chromatography-mass spectrometry; LC-MS/MS, liquid chromatography-mass spectrometry/mass spectrometry; LDL-C, low density lipoprotein cholesterol; LPL, lipoprotein lipase; M, molar; m/z, mass to charge ratio; MALDI, matrix-assisted laser desorption/ionization; $Me_3SO^+I^-$, trimethylsulfoxoniumiodid; MeOH, Methanol; Methanol-$d_3$, deuterated methanol; MetS, metabolic syndrome; $MgCl_2$, magnesium chloride; $MgSO_4$, magnesium sulfate; mRNA, messenger ribonucleic acid; MW, microwave; n.t., not tested; NADPH, nicotinamide adenine dinucleotide phosphate; NaH, sodium hydride; $NaN_3$, sodium azide; NaOH, sodium hydroxide; $NH_4Cl$, ammonium chloride; NMR, nuclear magnetic resonance spectrometry; —$OCF_3$, trifluoromethoxy substituent; —O—$CH_3$, methoxy substituent; —O— phenyl, oxophenyl substituent; p.o., per oral; P/S, penicillin/streptomycin; PBS, phosphate buffer system; $Pd(AcO)_2$, Palladium (II) acetate; PEPCK, phosphoenolpyruvat-carboxykinase; PHOME, (3-phenyl-cyano-(6-methoxy-2-naphthalenyl)methyl ester-2-oxirane-acetic acid; PK/PD, pharmacokinetic/pharmacodynamics; PPAR, peroxisome proliferator-activated receptor; PPARγ, peroxisome proliferator-activated receptor alpha; PPARγ, peroxisome proliferator-activated receptor gamma; qPCR, real-time polymerase chain reaction; RCT, reverse cholesterol transport; RP, reversed phase; RXR, retionid X receptor; SAR, structure activity relation; sEH, soluble epoxide hydrolase; sEH-KO, sEH knockout; SHROB, spontaneous hypertensive obese; SP, sodium pyruvate; STZ, streptozocin; T2D, type 2 diabetes; t-AUCB, trans-4-[4-(3-adamantan-1-yl-ureido)-cycloh exyloxy]-benzoic acid; TG, triglyceride; THF, tetrahydrofuran; TLC, thin-layer chromatography; $t_{max}$, time to reach the maximum concentration; TNFα, tumor necrosis factor α; TZD, thiazolidinedione; UV, ultra violate; $V_z$/f, volume of distribution (normalized to bioavailability); w.s., water solubility; WAT, white adipose tissue; WST-1, water soluble tetrazolium/(4-[3-(4-Iodophenyl)-2-(4-nitrophenyl)-2H-5-tetrazolio]-1,3-Benzol-Disulfonat).

Additional Materials and Methods a. Plasmids Used in the PPAR Transactivation Assay The Gal4-fusion receptor plasmids pFA-CMV-PPARγ-LBD, pFA-CMV-PPARγ-LBD and pFA-CMV-PPARγ-LBD containing the hinge region and ligand binding domain (LBD) for each of the PPAR subtypes, respectively, were constructed by integrating cDNA fragments obtained from PCR amplification of human monocytes into the SmaI/XbaI cleavage site of the pFA-CMV vector (Stratagene, La Jolla, Calif., USA) and have already been published. The cDNA fragments consist of bps 499-1407 (NM_005 036), bps 412-1323 (NM_006 238) and bps 610-1518 (NM_015 869) for PPARα, PPARδ and PPARγ, respectively. Frame and sequence of the fusion receptors were verified by sequencing. pFR-Luc (Stratagene) was used as reporter plasmid and pRL-SV40 (Promega) for normalization of transfection efficacy and cell growth.

b. Differentiation of Human Preadipocytes, RNA Isolation and Analysis

Preparation of Primary Human Preadipocytes and Differentiation

Human primary preadipocytes were obtained from stromal vascular fraction of subcutaneous fat from anonymous donors undergoing elective cosmetic surgery. Adipose tissue was digested by collagenase solution (0.3 U/ml in 1% BSA/PBS) for 45 min at 37° C. with constant shaking. Floating mature adipocytes were removed and the pellet containing the stromal vascular fraction was resuspended in erythrocyte lysis buffer. After consecutive filtration through 100 μm, 70 μm and 40 μm cell strainers preadipocytes were seeded in DMEM/Ham's F12 (1:1) nutrient mixture supplemented with 10% FCS, 33 μM biotin and 17 μM pantothenate. The following day, culture media was changed to QuickDiff medium (DMEM/Ham's F12 supplemented with 33 μM biotin, 17 μM pantothenate, 0.01 mg/ml transferrin, 20 nM insulin, 100 nM cortisol, 200 pM T3, 25 nM dexamethasone, 250 μM IBMX and 2 μM rosiglitazone). After 4 days the medium was changed to 3FC medium (QuickDiff medium without dexamethasone, IBMX and rosiglitazone). Adipocytes were cultured for additional 14 days before medium was changed to basal medium consisting of DMEM/Ham's F12 with biotin and panthotenate. This investigation conforms to the ethical principles outlined in the Declaration of Helsinki and was approved by the university ethics committee (Ethik-Kommission des Fachbereichs Medizin der Goethe-Universitat Frankfurt am Main). Total RNA was isolated using PeqGold RNAPure (Peqlab) according to manufacturer's instructions and was transcribed to cDNA using Maxima First Strand cDNA synthesis kit (Thermo Scientific), following manufacturer's instructions. Quantitative PCR was performed with iQ SYBR green Supermix (Bio-Rad) using a CFX96 (Bio-Rad) system. Expression was normalized to actin RNA.

c. In Vivo PK Studies po PK Mouse Study 9 male RjOrl:Swiss (CD-1) mice (28-42 g body weight, purchased from Janvier Labs, France) were used in the present study. The animals were housed in a temperature-controlled room (20-24° C.) and maintained in a 12h light/12h dark cycle. Food and water were available ad libitum. 30 mg/kg bw of compound 1b & 1c were applicate via gavage with 0.5% methylcellulose at an injection volume of 10 ml/kg in two different studies. Blood was sampled 15 min, 30 min, 1 h, 2 h, 4 h and 8 h after test item application and only 8 h after vehicle application. Each drug treated mouse was sampled twice (0.25 and 0.5 h, 1 and 2 h, 4 and 8 h) via retro orbital puncture. Blood was collected in tubes containing lithium-heparin, stored on ice and subsequently centrifuged at 6000 rpm for 10 minutes at 4° C. (Heraeus biofuge fresco). The plasma was prepared within 45 min after sampling and kept at −20° C. until being assayed. For further kinetic and dynamic analysis the tissues (brain, liver, abdominal fat) were collected 30 min, 2h and 8 h post dose, after the second plasma sampling of each drug treated mouse. Tissue of the vehicle group was sampled only once, 8 h post dose. A volume of 40 μl acetonitrile containing the internal standard (300 ng/ml Diazepam) was added to 20 μl of mouse plasma sample, plasma calibration standard and plasma QC samples. Samples were vigorously shaken and centrifuged for 10 minutes at 6000 g and 20° C. The particle free supernatant was diluted 1:1 with water. An aliquot was transferred to 200 μl sampler vials and subsequently subjected to LC MS with an injection volume of 20 μl. The brain samples were homogenized in PBS (1+1, w/v) using the Precellys 24/Dual homogenizer. A volume of 20 μl of the brain homogenate was mixed (1+1 v/v/) with 20 μl mouse blank plasma. Then 80 μl acetonitrile containing the internal standard (300 ng/ml Diazepam) were added. Samples were vigorously shaken and centrifuged for 10 minutes at 6000 g and 20° C. The particle free supernatant was diluted 1:1 with water. An aliquot was transferred to 200 μl sampler vials and subsequently subjected to LC MS with an injection volume of 20 μl. Mass spectrometry was performed on a TSQ Quantum Discovery Max triple quadrupole mass spectrometer equipped with an electrospray (ESI) interface (Thermo Fisher Scientific, USA) connected to a PC running the standard software Xcalibur 2.0.7. The HPLC pump flow rate was set to 600 μl/min and the test item was separated on a Kinetex Phenyl-Hexyl, 2.6 μm, 50×2.1 mm (Phenomenex, Germany) analytical column with a precolumn. Gradient elution with water/0.1% formic acid as aqueous phase (A) and acetonitrile/0.1% formic acid as organic phase (B) was used: % B (t (min)), 5(0-0.1)-97(0.8-1.7)-5(1.8-2.5).

2 Week Drinking Water PK Mouse Study 9 male C57BL/6JRj mice (23-27 g body weight, purchased from Janvier Labs, France) were used in the present study. The animals were housed in a temperature-controlled room (20-24° C.) and maintained in a 12h light/12h dark cycle. Food and water were available ad libitum. 14c was not soluble in plain drinking water. For this reason, different cosolvents were used for different time periods of the study. A 3 mg/ml stock solution of 14c was prepared by dissolution of 283.4 mg 14c in 94.46 ml ethanol. A volume of 10 ml of this stock solution was added to 190 ml tap water in a drinking bottle to obtain a final concentration of 0.15 mg/ml (estimated target dose of 30 mg/kg). This was provided to the mice from the afternoon of day 1 until the afternoon of day 5. No precipitates were observed in this mixture when it was removed from the cage on day 5. A 1.5 mg/ml stock solution of 14c was prepared mixing 100 mg 14c in 66.7 ml 1% Tween 80. As the test item was not completely dissolved, the mixture was subjected to sonication at 37° C. By mistake, a volume of 10 ml of the resulting slightly opaque suspension was added to 190 ml instead of 90 ml tap water in a drinking bottle and provided to the mice from the afternoon of day 5 until the afternoon of day 7. This corresponds to a final concentration of only 0.075 mg/ml (estimated dose of 15 mg/kg 14c in 0.05% Tween 80) A few precipitates were observed in this mixture when it was removed from the cage on day 7. The 1.5 mg/ml stock solution of 14c of 20.9.2014 was again subjected to sonication at 37° C. and a volume of 10 ml of the resulting slightly opaque suspension was added to 90 ml tap water in a drinking bottle and provided to the mice from the afternoon of day 7 until the afternoon of day 10. This corresponds to a final concentration of 0.15 mg/ml (estimated dose of 30 mg/kg 14c in 0.1% Tween 80). A few precipitates were observed in this mixture when it was removed from the cage on day 10. A fresh 1.5 mg/ml stock solution of 14c was prepared mixing 29.77 mg 14c in 19.85 ml 1% Tween 80. The mixture was subjected to sonication at 37° C. A volume of 10 ml of the resulting slightly opaque suspension was added to 90 ml tap water in a drinking bottle and provided to the mice from the afternoon of day 10 until the afternoon of day 14. This corresponds to a final concentration of 0.15 mg/ml (estimated dose of 30 mg/kg 14c in 0.1% Tween 80). A few precipitates were observed in this mixture when it was removed from the cage on day 14. The test item was dissolved in drinking water freshly every 2-4 days and provided to the animals for a total duration of 14 days. Water intake was recorded per cage, every time before provision of the fresh solution. Water intake was recorded per cage, every time before provision of the fresh solution. The corresponding final concentration was 0.15 mg/ml (estimated dose of 30 mg/kg 14c in 0.1% Tween 80). Blood was sampled on day 7 and 10, collected from the retrobulbar venous plexus of each mouse under short isoflurane anesthesia, in tubes containing lithium-heparin. Blood was stored on ice and subsequently centrifuged at 6000 rpm for 10 minutes at 4° C. (Heraeus biofuge fresco). The plasma was prepared within 45 min after sampling and was kept at −20° C. until being assayed. After 14 days plasma and tissue (complete liver, both kidneys, pancreas, abdominal fat) was sampled for further dynamic studies. The whole plasma was collected as described bevor. For tissue collection, mice were sacrificed by cervical dislocation. Tissues were immediately frozen in liquid nitrogen and stored at −80° C. until analyzed. Concentration of the test item was only determined in plasma due the same method described under section PO PK mouse study.

d. EET/DHET Ratio Analysis: Determination of Epoxyeicosatrienoicacids (EETs) and their Metabolites Dihydroxyepoxyeicosatrienoicacids (DHETs) by LC/MS-MS 5.6 EET, 8.9 EET, 11.12 EET, 14.15 EET and their further dehydro metabolites content of the extracted samples were analyzed employing liquid chromatography tandem mass spectroscopy (LC-MS/MS). The LC/MS-MS system comprised an API 5500 QTrap (AB Sciex, Darmstadt, Germany), equipped with a Turbo-V-source operating in negative ESI mode, an Agilent 1200 binary HPLC pump and degasser (Agilent, Waldbronn, Germany) and an HTC Pal autosampler (Chromtech, Idstein, Germany) fitted with a 25 μL LEAP syringe (Axel Semrau GmbH, Sprockhovel, Germany). High purity nitrogen for the mass spectrometer was produced by a NGM 22-LC/MS nitrogen generator (cmc Instruments, Eschborn, Germany). All substances were obtained from Cayman Chemical, Ann Arbor, Mich., USA. Stock solutions with 2500 ng/ml of all analyte were prepared in methanol. Working standards were obtained by further dilution with a concentration range of 0.1-250 ng/ml for epoxyeicosatrienoicacid and their dehydrometabolites respectively. Sample extraction was performed with liquid-liquid-extraction. Therefore 150 μl of matrix homogenates were gently mixed with 20 μl of internal standard (5.6 EET-d11, 8.9 EET-d8, 11.12 EET-d8 and 14.15 EET-d8 all with a concentration of 200 ng/ml in methanol), and were extracted twice with 600 μL of ethyl acetate. Samples for standard curve and quality control were prepared similarly, instead of 150 μl of matrix homogenates, 150 PBS were added further 20 μL methanol 20 μL working standard and 20 μL internal standard were added. The organic phase was removed at a temperature of 45° C. under a gentle stream of nitrogen. The residues were reconstituted with 50 μL of methanol/water/(50:50, v/v), centrifuged for 2 minutes at 10,000 g and then transferred to glass vials (Macherey-Nagel, Düren, Germany) prior to injected into the LC-MS/MS system. For the chromatographic separation a Gemini NX C18 column and precolumn were used (150 mm×2 mm i. d., Sum particle size and 110 Å pore size from Phenomenex, Aschaffenburg, Germany). A linear gradient was employed at a flow rate of 0.5 ml/min mobile phase with a total run time of 17.5 minutes. Mobile phase was A water/ammonia (100:0.05, v/v) and B acetonitrile/ammonia (100:0.05, v/v). The gradient started from 85% A to 10% within 12 min this was held for 1 min at 10% A. Within 0.5 min the mobile phase shifted back to 85% A and was held for 3.5 min to equilibrate the column for the next sample. The injection volume of samples was 20 μL. Quantification was performed with Analyst Software V 1.5.1 (Applied Biosystems, Darmstadt, Germany) employing the internal standard method (isotope-dilution mass spectrometry). Ratios of analyte peak area and internal standard area (y-axis) were plotted against concentration (x-axis) and calibration curves were calculated by least square regression with 1/concentration2 weighting.

e. Method of IP1 (Inositolmonophosphate) Measurement Cell Culture

Stably transfected Flp-In™ T-REx™ 293 cells (Invitrogen) were cultured in Dulbecco's modified Eagles's medium (DMEM) containing 10% (v/v) fetal bovine serum (FBS), penicillin (100 U/mL), streptomycin (100 μg/mL), Hygromycin B (100 μg/mL) and Blasticidin (15 μg/mL) at 37° C. and 5% $CO_2$. All experiments were carried out after inducing receptor expression with 1 μg/mL doxycycline for approximately 18 hours, according to manufacturer's instructions (Invitrogen).

IP1 Measurement

Compound activity on the Gq coupled FFA1 receptor constructs was assessed by measuring intracellular level of inositolmonophosphate (IP1) using the HTRF®-IP-One kit (Cisbio International) according to manufacturer's instructions. Briefly, 10,000 receptor expressing cells were seeded into a 384 well microplate and incubated 20 minutes at 37° C. The cells were then stimulated with agonist for 30 minutes and IP levels were quantified using the HTRF®-IP-One kit and the Mithras LB 940 multimode reader (Berthold Technologies) using emission/excitation filter of 665 nm/620 nm. Data analysis and nonlinear regression curve fitting were carried out using the GraphPad Prism® software v5.04 (Graphpad Software).

Reference (1) Christiansen, E.; Due-Hansen, M. E.; Urban, C.; Grundmann, M.; Schmidt, J.; Hansen, S. V. F.; Hudson, B. D.; Zaibi, M.; Markussen, S. B.; Hagesaether, E.; Milligan, G.; Cawthorne, M. a.; Kostenis, E.; Kassack, M. U.; Ulven, T. Discovery of a Potent and Selective Free Fatty Acid Receptor 1 Agonist with Low Lipophilicity and High Oral Bioavailability. *Journal of Medicinal Chemistry* 2013, 56, 982-992.

Example 2: In Vivo Studies in the Spontaneously Hypertensive Obese Rat (SHROB) Model The inventors hypothesized that the dual soluble epoxide inhibitor and PPARg agonist, RB394 (identified as compound 14c elsewhere), would provide synergistic actions to decrease blood pressure, decrease insulin resistance, and prevent end organ damage in spontaneously hypertensive obese rats (SHROB). SHROB were treated with RB394 (10 mg/kg/d, p.o.; n=6) for 8-weeks. Blood pressure increased in SHROB and failed to increase in SHROB treated with RB394. Insulin glucose tolerance testing revealed improved insulin sensitivity in the RB394 treated SHROB group. Albuminuria was increased in SHROB and was significantly decreased by RB394. Heart function assessed by echocardiography was improved in SHROB treated with RB394 (see FIGS. 16, 17, 18, 19, and 20 respectively). These results indicate that RB394 has beneficial effects in cardiometabolic syndrome SHROB rats.

There are a number of drugs on the market for the treatment of diabetes, obesity, hypertension, and end organ damage such as chronic kidney disease and heart failure. Drugs to treat diabetes include insulin, metformin, thaizolidinediones, dipeptidyl inhibitors, megalitinides, and alpha glucosidase inhibitors. The noradrenergic agent, phentermine/topiramate and the selective serotonin receptor agonist, loracaserin are drugs for treating obesity that were FDA approved in 2012. But birth defects and tachycardia are side effects of phentermine/topiramate. There is risk of valvulopathy in obese type 2 diabetics associated with loracaserin. Hypertension drugs include renin-angiotensin system blockers, diuretics, and beta-blockers. For chronic kidney disease analysis has revealed that competition among marketed products is weak. There are more than 12 marketed products for chronic kidney disease that are moderately effective with serious adverse side effects that have resulted in the discontinuation of therapies amongst humans. Patients with diabetes, obesity, hypertension and chronic kidney disease are also prescribed lipid lowering agents and anti-platelet agents to prevent end-organ damage and mortality. In spite of the use of multidrug regimens in these patient populations, the prevalence of end organ damage is increasing, and mortality in these patient populations remains a serious health problem. RB394 based soluble epoxide hydrolase inhibitor/PPARg agonists are a unique therapeutic approach because RB394 demonstrates great promise as an anti-hypertensive, decreased insulin resistance and decreased end organ damage in spontaneously hypertensive obese rats.

RB394 is identified elsewhere herein as Compound 14c.

Figure 21:
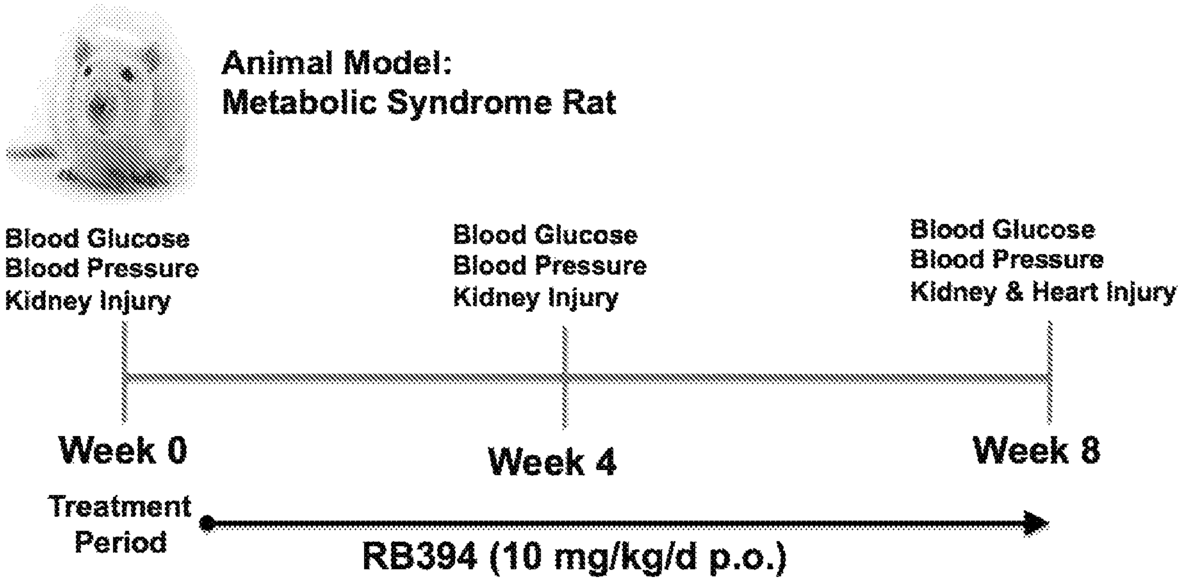
FIG. 21 depicts the MetS rat model and RB394 assay time course.

Example 3: RB394 Improves Insulin Resistance and Diabetes, Decreases Blood Pressure, Decreases Renal Injury in Spontaneously Hypertensive Obese (SHROB) Rats and ZSF1 (fa-Fa$^{cp}$) Rats Metabolic syndrome (MetS) is a cluster of symptoms including hypertension, hyperglycemia, hypertriglyceridemia and obesity. Due to the complexity of this syndrome, patients are often prescribed numerous medications, leading to an increased risk of negative drug interactions and higher drug cost. The inventors hypothesized that the development of a dual modulator (a drug that combines two pharmacophores) could treat more than one symptom of MetS and prevent renal injury. Soluble epoxide hydrolase (sEH) inhibitors and PPAR-γ agonists have therapeutic potential in MetS. The inventors synthesized a novel dual sEH inhibitor-PPAR-γ agonist (sEHi/PPAR-γ), RB394 and investigated its efficacy in a rat model of MetS (see FIG. 21). Three groups of rats were utilized; Group 1: Wister Kyoto (WKY)+Vehicle (n=6); Group 2: Spontaneously Hypertensive Obese (SHROB)+Vehicle (n=5); Group 3: SHROB+RB394 (10 mg/kg/d p.o.; n=5). RB394 or vehicle treatments were administered for 56 days, blood pressure measured, and urine and kidney tissues collected at the end of treatment period. The SHROB rats were hypertensive (187±7 mmHg) compared to WKY rats (137±5 mmHg, P<0.05), and RB394 markedly reduced hypertension in SHROB rats (144±4 mmHg, P<0.05). Kidney injury was assessed from albuminuria, and also from histopathological analysis of renal tubular cast formation, collagen formation and glomerular injury using Periodic Acid Schiff and Picro Sirius Red staining. The SHROB rats developed renal damage with marked albuminuria (243±18 mg/d) compared to WKY (1.0±0.1 mg/d, P<0.05), and RB394 decreased it by reducing albuminuria (59±11 mg/d, P<0.05). The kidney of SHROB rats had markedly elevated protein cast and collagen, and RB394 reduced the cast and collagen formation by 40-50%. Glomerular injury was also prominent in SHROB rats and RB394 reduced it by 45%. The SHROB rats also had marked renal inflammation with infiltrating immune cells in the kidney, and RB394 reduced it by 20%. Overall, our results demonstrate that a dual sEHi/PPAR-γ, RB394, prevented renal injury in SHROB MetS rats. These results indicate an exciting opportunity for a new way to more effectively treat patients with MetS.

Materials and Methods

Animal Groups

The Medical College of Wisconsin Institutional Animal Care and Use Committee according to the National Institutes of Health Guidelines for Care and Use of Laboratory Animals approved all animal studies. Eight to nine-week-old male Wistar-Kyoto (WKY), and SHROB were purchased from Charles River Laboratories (Wilmington, Mass., USA). Animals were housed in the Biomedical Resource Center at Medical College of Wisconsin with a 12 hour light-dark cycle and free access to tap water along with rat chow. WKY rats (n=6) were used as a control group as a comparison for disease progression. SHROB rats were divided into 2 groups. Group 1 received vehicle (n=5) and Group 2 received RB394 (10 mg/kg/d p.o.; n=5) for 8 weeks. Rats were weighed and systolic blood pressure was measured by tail-cuff plethysmography.

Glucose Tolerance Test

Intra-peritoneal glucose tolerance test was carried out during the 8-week treatment protocol in rats that were fasted overnight and injected with glucose (2 g/kg i.p.). Blood samples were collected from the tail vein before and at different time points after glucose injection. The tail vein blood glucose levels were measured using a glucometer LifeScan (Miltipas, Calif., USA).

Urine and Plasma Biochemical Analysis

During the experimental period rat urine was collected from rats housed in metabolic cages for 24 h. Urinary biochemical analysis was done using commercially available ELISA kits; albumin and from Exocell (Philadelphia, Pa.). Rats were anesthetized using isoflorane and plasma collected from the artery. Triglyceride, cholesterol, protein and creatinine assay kits were from Cayman (Ann Arbor, Mich., USA), and free fatty acids from Zen-Bio Inc. (Research Triangle Park, N.C.). Blood glucose levels from the tail vein were measured using a glucometer.

Histopathological Analysis

The kidney was excised and immersion-fixed in 10% neutral buffered formalin and paraffin embedded. The embedded kidney and pancreas sections were cut into 4 μm slices for use in histology. Formalin-fixed paraffin-embedded tissue slices were deparaffinized, re-hydrated, and kidney tissue slices were stained with Periodic Acid-Schiff (PAS) and Masson's Trichorme. Glomerulosclerosis and mesangial matrix expansion were blindly scored from kidney sections stained with PAS staining using the following numeric scale: 0=no damage; +1=very mild; +2=mild; +3=moderate and +4=severe. Two observers in a blinded fashion conducted histological analysis at a magnification of ×200 using Nikon NIS Elements Software (Nikon Instruments Inc., Melville, N.Y., USA). Proteinaceous cast in the kidney was also determined in PAS stained kidney sections at magnification of ×200 using Nikon NIS Elements Software. The percentage area positive for proteinaceous cast was calculated from the mean of eight cortical and five medullary fields for each animal. Fibrosis in the kidney was determined in kidney sections stained with Masson's Trichorme at a magnification of ×200. The percentage area positive for collagen was calculated as fibrotic area from the mean of eight cortical and five medullary fields for each animal. Renal tubular cast and collagen positive fibrotic areas in the kidney sections were determined by two blinded observers. The pancreas slices were stained with Hematoxylin and Eosin staining and gross histological features of the pancreas were studied in different experimental groups in blinded fashion.

Immunohistopathological Analysis

Formalin-fixed paraffin-embedded kidney slices were deparaffinized, re-hydrated, and subjected to immunohistochemistry. Kidney sections were immunostained with anti-CD68 (1:100; Serotec, Raleigh, N.C., USA) to determine macrophage/monocyte infiltration in the kidney. Biotinylated rat anti-mouse secondary antibody (1:200) was used for development with avidin-biotinylated HRP complex (Vectastain ABC Elite kit, Vector Laboratories, Burlingame, Calif., USA) followed by counterstaining with hematoxylin and mounted for image capturing. Stained sections were visualized by light microscopy at 400× magnification and digital images of the stained kidney were taken for analysis using Nikon NIS Elements Software (Nikon Instruments Inc., Melville, N.Y., USA). Macrophage/monocyte infiltration was determined by point counting CD68-positive cells by two experienced blinded reviewers. The number of positive cells per picture was divided by the metric area of the image to obtain the number of positive cells per $mm^2$.

Results

Body Weight, Blood Pressure, Blood Glucose, Triglyceride, Cholesterol, and Free Fatty Acids Mean body weight was measured in all experimental groups at baseline and throughout the study. Body weight, systolic blood pressure and blood glucose are shown in Table 5. At the end of the 8-week study body weights were significantly higher in the SHROB compared to the WKY. Body weight in SHROB treated with RB394 gained approximately 40 g more than vehicle treated SHROB. Systolic blood pressure in the RB394 treatment group was approximately 44 mmHg lower than vehicle treated SHROB. SHROB did not have an increase in fasting blood glucose compared to the WKY. Table displays the results of plasma biochemical analysis for triglycerides, cholesterol, and free fatty acids. Triglycerides, cholesterol and free fatty acid levels were significantly increased in the vehicle treated SHROB compared to the normotensive WKY group. SHROB had significant improvement of triglycerides when treated with RB394. Cholesterol levels in RB394 treated SHROB groups decreased over the 8-week treatment period. Plasma free fatty acid levels decreased in SHROB treated with RB394.

Table 5

| Measurements | WKY + Vehicle | SHROB + Vehicle | SHROB + RB394 |
|---|---|---|---|
| Body Weight (g) | 351 ± 4 | *562 ± 7 | 600 ± 8 |
| Systolic Blood Pressure (mmHg) | 137 ± 7 | *187 ± 9 | #143 ± 9 |
| Fasting Blood Glucose (mg/dL) | 90 ± 3 | 89 ± 4 | 83 ± 7 |
| Triglyceride (mg/dL) | 29 ± 4.2 | *313 ± 50 | #133 ± 18 |
| Serum Cholesterol (mM) | 2.5 ± 0.2 | *10.0 ± 0.5 | #4.0 ± 0.7 |
| Serum LDL (mg/mL) | 35 ± 3 | *72 ± 7 | #44 ± 6 |
| Free fatty Acid (μM) | 152 ± 27 | *732 ± 121 | #322 ± 24 |

Insulin Resistance

Figure 22:
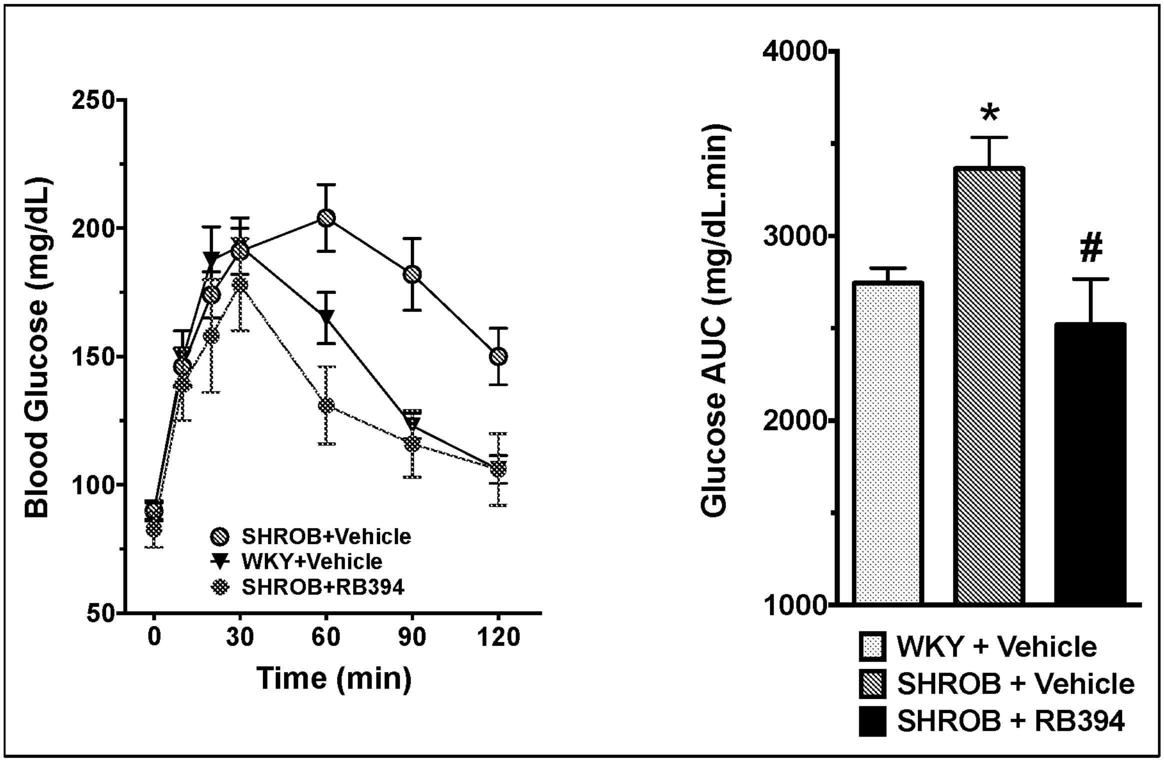
FIG. 22 illustrates blood glucose and glucose AUC data.

The SHROB rats were insulin resistant compared to WKY rats. RB394 did not alter fasting blood glucose but and improved glucose tolerance in SHROB rats. The SHROB rats also had insulin resistance with a higher glucose area under the curve compared to WKY rats, and RB394 reduced insulin resistance in the SHROB rats. See FIG. 22

Kidney Injury

Figure 23:
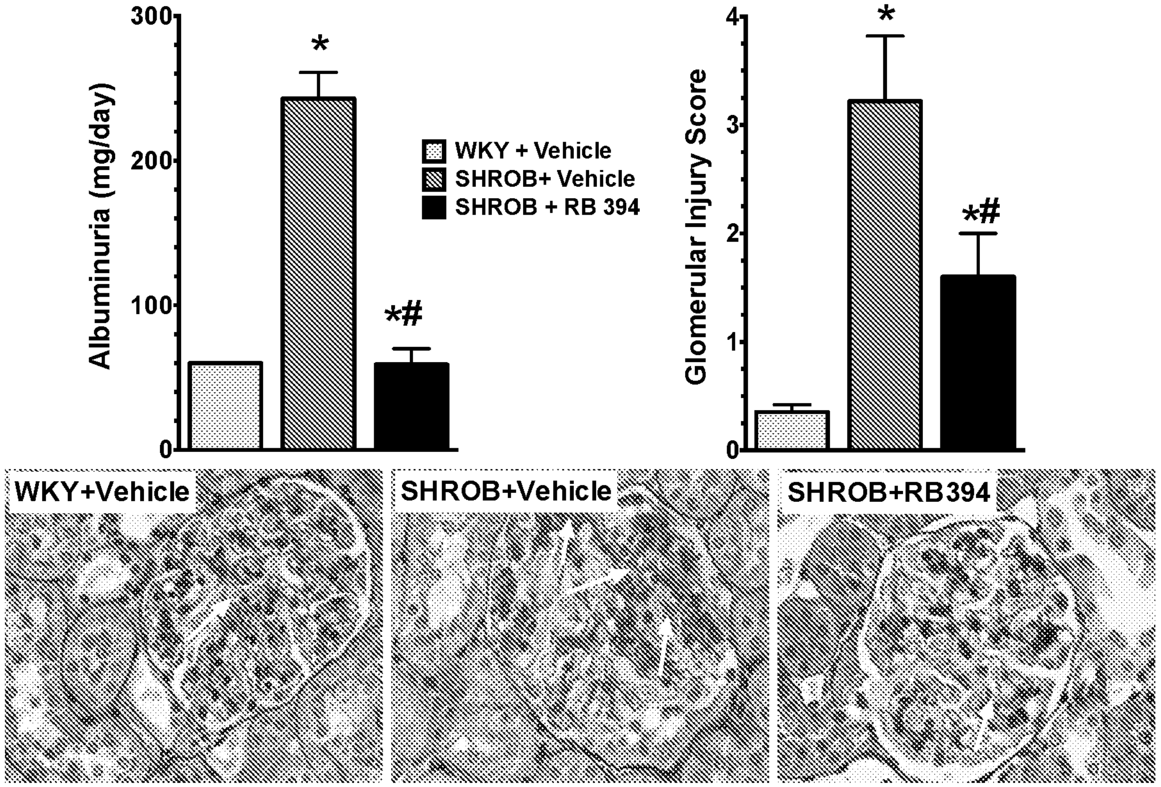
FIG. 23 illustrates albuminuria and glomerular injury score.
Figure 24:
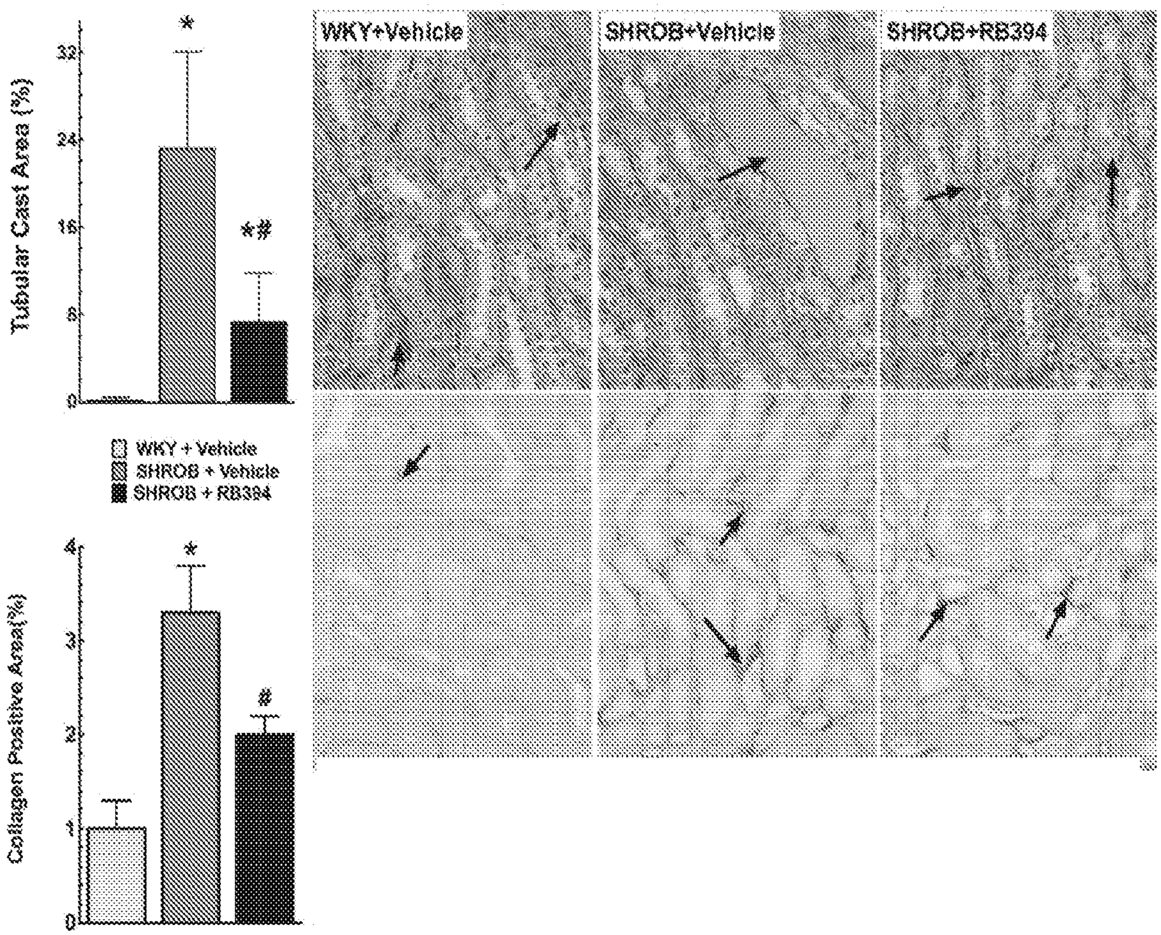
FIG. 24 shows Peridic-Acid Schiff staining (×200) depicting tubular cast (upper panel) and Picrosirus Red staining (×200) depicting fibrosis (lower panel) formation (arrows) in the kidney. *P<0.05, WKY+Vehicle vs. SHROB+Vehicle, #P<0.05, SHROB+Vehicle vs. SHROB+RB394.

Urinary albumin excretion levels were analyzed to assess the degree of renal injury in SHROB. Albumin excretion significantly increased in the SHROB compared to WKY and RB394 decreased albumin levels. Renal injury was further evaluated semi-quantitatively by scoring a sampling of 100 glomeruli per kidney from histological sections. Glomerular injury was minimal in the WKY and vehicle treated SHROB demonstrate a significantly higher glomerular injury score. The vehicle treated SHROB demonstrated mesangial expansion and damage to the glomerular basement membrane that is consistent with the albumin excretion rates. SHROB treated with RB394 demonstrated a reduction in glomerular injury. (See FIG. 23) Additionally, RB394 significantly reduced intra-tubular proteinaceous cast formation in the cortical and medullary areas of the kidney. (See FIG. 24) Taken together, these findings demonstrate that RB394 decreased renal injury.

Renal Inflammation

Figure 25:
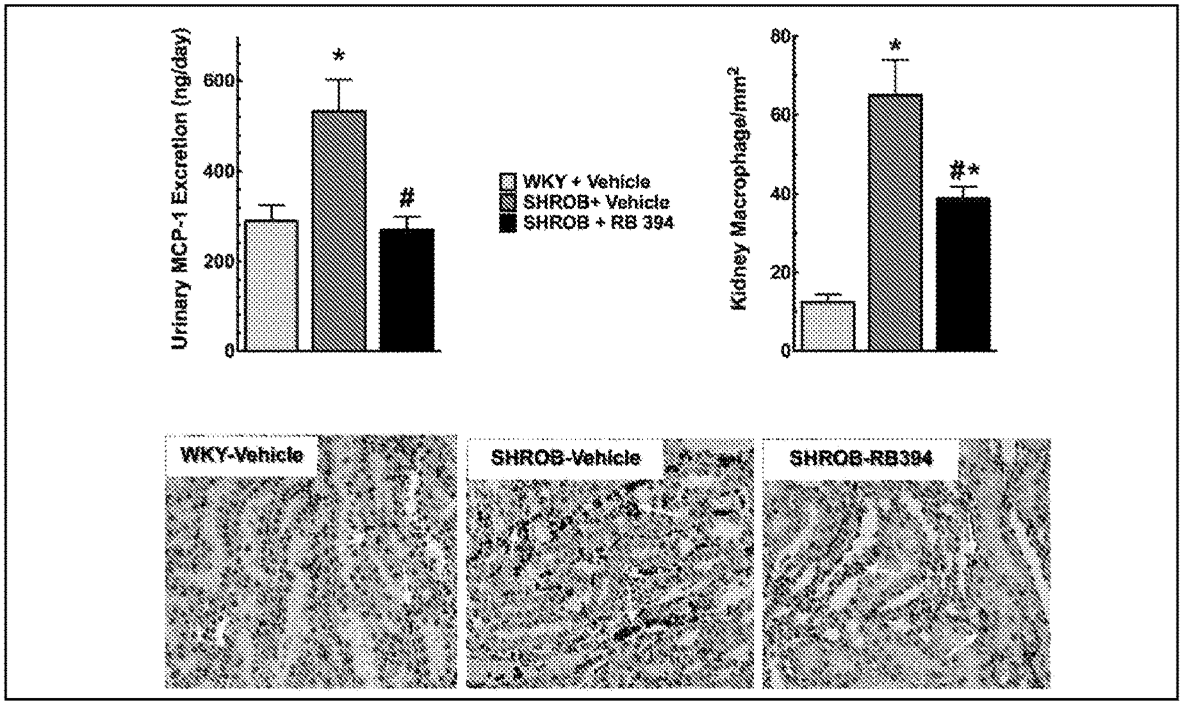
FIG. 25 shows inflammatory markers MCP-1 excretion (Upper left), semi-quantitative scoring of renal macrophage infiltration (Upper Right) and representative photomicrographs (Bottom) showing macrophage infiltration in the kidney (×200; arrows) of WKY and SHROB after 8 weeks of vehicle or RB394 treatment. *P<0.05, WKY+Vehicle vs. SHROB+Vehicle; #P<0.05, SHROB+Vehicle vs. SHROB+RB394.

FIG. 25 presents urinary MCP-1 excretion and representative analysis and pictures of macrophage infiltration in the kidney sections immunostained with anti-CD68, a glycoprotein that is expressed in monocytes and macrophages. MCP-1 levels were significantly elevated in SHROB compared to WKY group. RB394 decreased urinary MCP-1 excretion in SHROB. Consistent with the MCP-1 data, the SHROB vehicle group had an increase in renal macrophage infiltration compared to WKY group. SHROB treated with RB394 had a significant reduction in macrophage infiltration. These data indicate that RB394 treatment reduced renal inflammation in SHROB.

Figure 26:
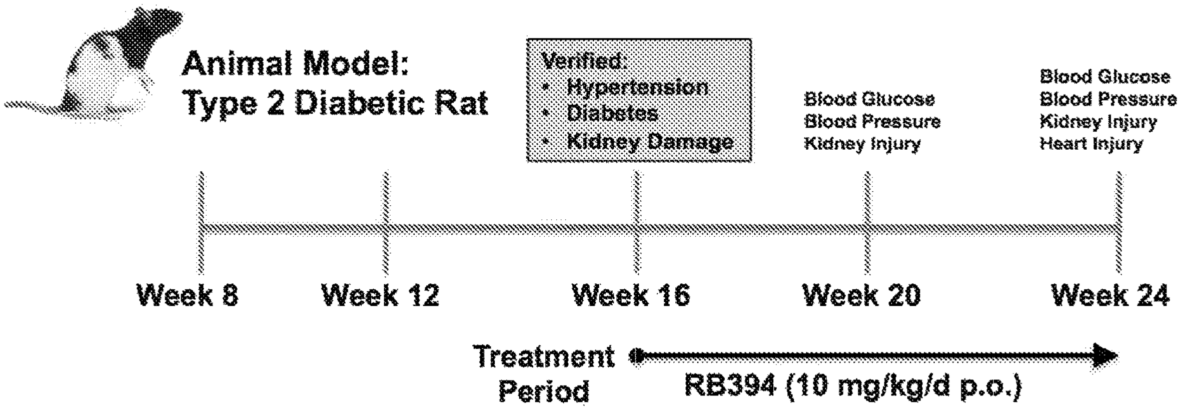
FIG. 26 depicts the Type 2 diabetic rat model and methodology used by the inventors.

ZSF1 methodology is similar to SHROB study. See FIG. 26. Hypertension, diabetes, kidney damage were verified by measuring blood pressure, fasting blood glucose, and urinary protein in ZSF1 obese rats at 16 weeks of age. RB394 treatment was started in ZSF1 obese rats at 16 weeks of age and continued for 8 weeks. Initial graphs for blood pressure, glucose tolerance, and urinary protein are presented.

Results

Blood Pressure

Figure 27:
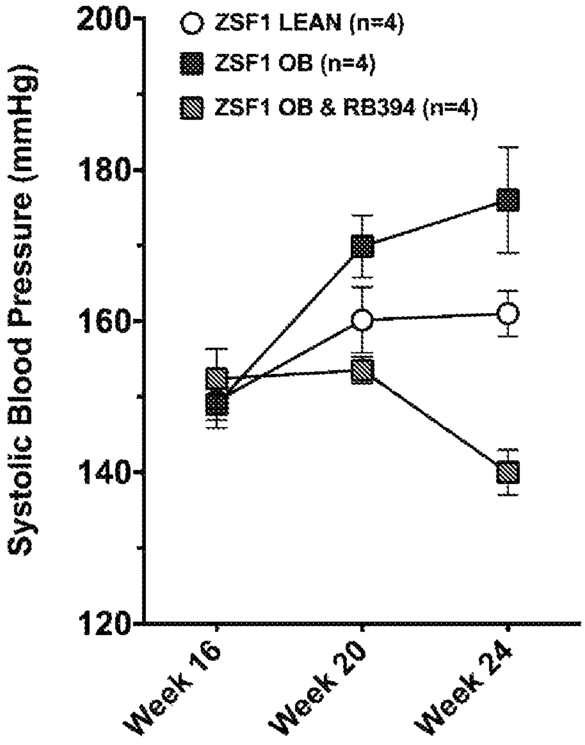
FIG. 27 illustrates systolic blood pressure data for ZSF1 rats.

ZSF1 obese rats had a rise in systolic blood pressure from week 16 of age to week 24 of age. See FIG. 27. RB394 treatment was started at week 16 of age and continued for 8 weeks to week 24 of age. Treatment with RB394 for 8 weeks lowered systolic blood pressure in ZSF1 obese rats.

Blood Glucose

Figure 28:
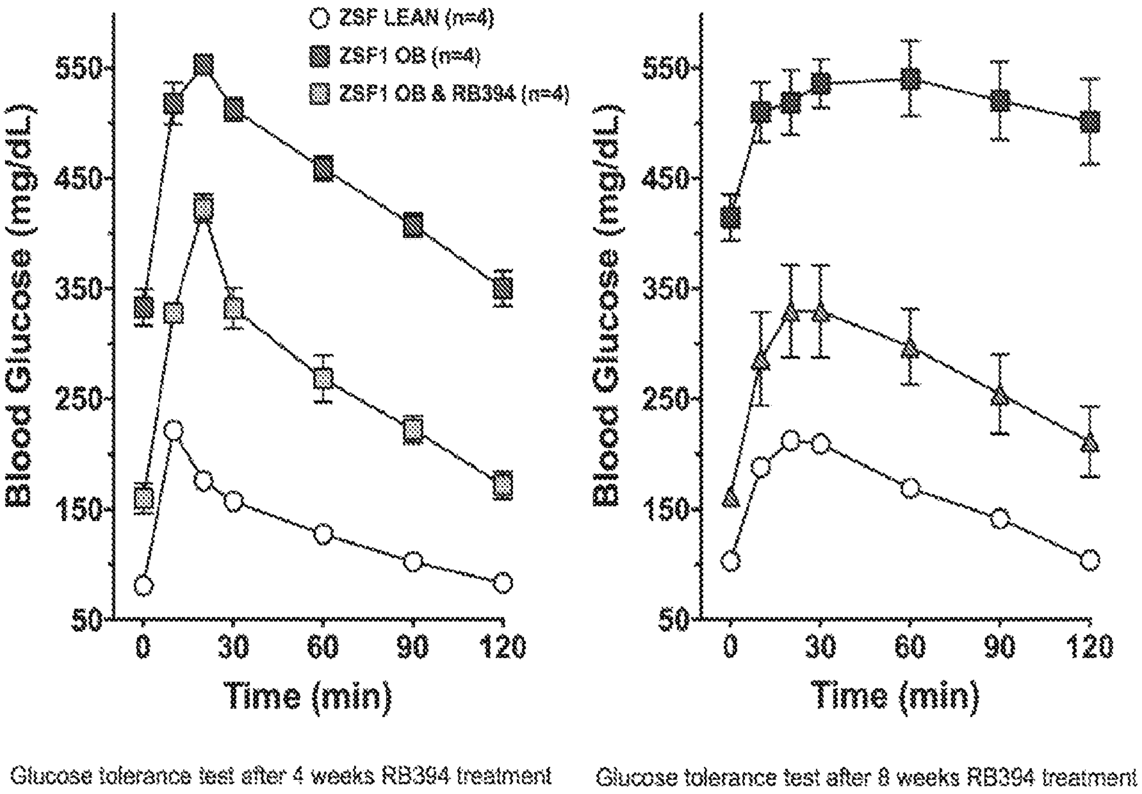
FIG. 28 depicts blood glucose data for ZSF1 rats.

As shown in FIG. 28, ZSF1 obese rats have elevated fasting blood glucose and impaired glucose tolerance at 20 weeks (left panel) and 24 weeks (right panel) of age compared to ZSF lean rats. RB394 treatment was started at week 16 of age and continued for 8 weeks to week 24 of age. Treatment with RB394 for 4 weeks (left panel) or 8 weeks (right panel) lowered fasting blood glucose levels and improved glucose tolerance in ZSF1 obese rats.

Kidney Injury—Proteinuria

Figure 29:
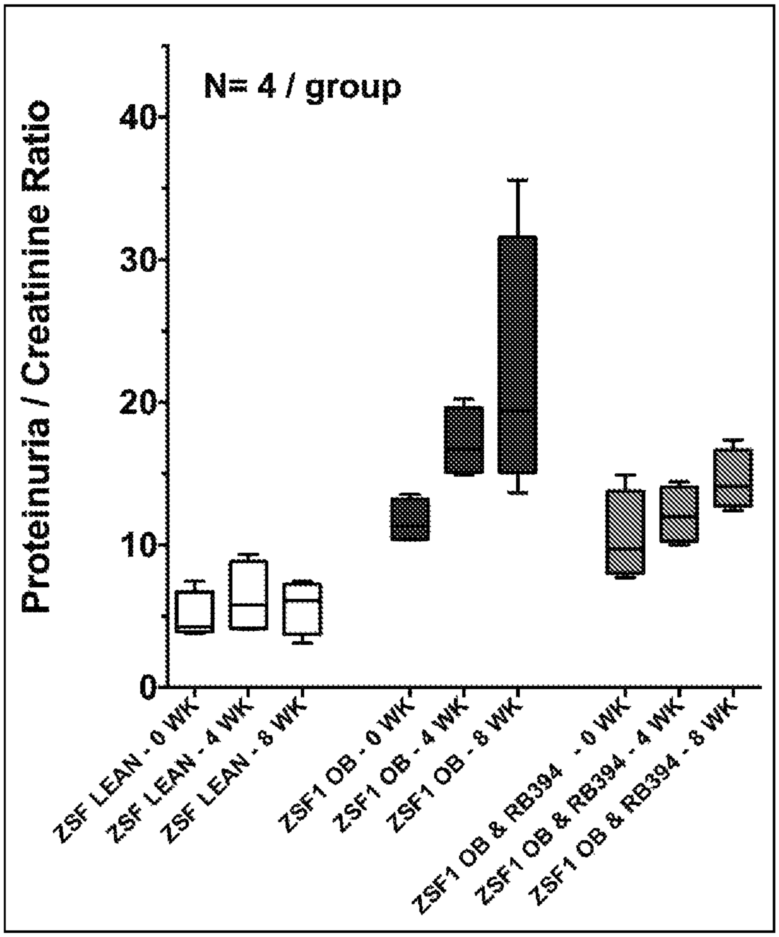
FIG. 29 illustrates proteinuria/creatiniue ratio data for ZSF1 rats.

As shown in FIG. 29, ZSF1 obese rats have increased urinary protein excretion at 16 weeks of age (0 WK) compared to ZSF1 lean rats. Urinary protein excretion was further increased at 20 weeks (4 WK) and 24 weeks (8 WK) of age in untreated ZSF1 obese rats. RB394 treatment was started at 16 weeks of age and prevented the increase in urinary protein excretion in ZSF1 obese rats.

Each reference identified in the present application is herein incorporated by reference in its entirety. While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

References (1) Scott M. Grundy, H. Bryan Brewer, Jr, James I. Cleeman, Sidney C. Smith, J. and C. L. Definition of Metabolic Syndrome: Report of the National Heart, Lung, and Blood Institute/American Heart Association Conference on Scientific Issues Related to Definition. *Arterioscler Thromb Vasc Biol. Journal of the American Heart Association* 2004, 24, 433-438.

(2) Antonova, P.; Jacobs, D. I.; Bojar, M.; Černý, R.; Ciharová, K.; Frick, M. A.; Fintel, B.; Dehovitz, J.; Bennett, C. L. The Metabolic Syndrome. *the lancet* 2009, 375, 181-183.

(3) Grundy, S. M. Drug Therapy of the Metabolic Syndrome: Minimizing the Emerging Crisis in Polypharmacy. *Nature reviews. Drug discovery* 2006, 5 (4), 295-309.

(4) Aydin, S.; Aksoy, A.; Suna Aydin, Mehmet Kalayci, Musa Yilmaz, T. K.; Citil, Cihan, Z. C. Today'S and Yesterday'S of Pathophysiology: Biochemistry of Metabolic Syndrome and Animal Models. *Nutrition* 2014, 30 (1), 1-9.

(5) Javed, S.; Petropoulos, I. N.; Alam, U.; Malik, R. A. Treatment of Painful Diabetic Neuropathy. *Therapeutic Advances in Chronic Disease* 2015, 6(1) 15-2, 15-28.

(6) Chan, G. C. W.; Tang, S. C. W. Diabetic Nephropathy: Landmark Clinical Trials and Tribulations. *Nephrol Dial Transplant* 2015, 1-10.

(7) Grundy, S. M.; Cleeman, J. I.; Daniels, S. R.; Donato, K. A.; Eckel, R. H.; Franklin, B. A.; Gordon, D. J.; Krauss, R. M.; Savage, P. J.; Smith, S. C.; Spertus, J. A.; Costa, F. Diagnosis and Management of the Metabolic Syndrome. *Circulation* 2006, 112, 285-290.

(8) National Heart Lung and Blood Institute; National Institutes of Health (NIH) National Heart, Lung, and Blood Institute, N. *Clinical Guidelines on the Identification, Evaluation, and Treatment of Overweight and Obesity in Adults. The Evidence Report, NIH Publication No.* 98-4083.; 1998; Vol. 158, p 51S-209S.

(9) Buse, R. K. J.; Stern, E. F. M. The Metabolic Syndrome: Time for a Critical Appraisal Joint Statement from the American Diabetes Association and the European. *Diabetologia* 2005, 48, 1684-1699.

(10) Nawrocki, A. R.; Scherer, P. E. Keynote Review: The Adipocyte as a Drug Discovery Target. *Drug Discovery Today* 2005, 10 (18), 1219-1230.

(11) George, M.; Rajaram, M.; Shanmugam, E. New and Emerging Drug Molecules Against Obesity. *Journal of Cardiovascular Pharmacology* and Therapeutics 2013, 19 (1), 65-76.

(12) Sp, A.; Ss, S.; Jm, W. Lipid-Lowering Efficacy of Rosuvastatin (Review). *the cochrane libary* 2014, No. 11.

(13) Sahebkar, A.; Watts, G. F. Fibrate Therapy and Circulating Adiponectin Concentrations: Asystematic Review and Meta-Analysis of Randomized Placebo-Controlled Trials. *Atherosclerosis* 2013, 230 (1), 110-120.

(14) Azimova, K.; Juan, Z. S.; Mukherjee, D. Cardiovascular Safety Profile of Currently Available Diabetic Drugs. *The Ochsner Journa* 2014, 14, 616-632.

(15) Pollare, T.; Lithell, H.; Selinus, I.; Berne, C. Sensitivity to Insulin during Treatment with Atenolol and Metoprolol: A Randomised, Double Blind Study of Effects on Carbohydrate and Lipoprotein Metabolism in Hypertensive Patients. *BMJ* (*Clinical research ed.*) 1989, 298 (April), 1152-1157.

(16) Khan, M. Z. Mechanism Linking Diabetes Mellitus and Obesity. *Diabetes, Metabolic Syndrom and Obesity: Targets and Therapy* 2014, 587-591.

(17) Gustafson, B.; Hedjazifar, S.; Gogg, S.; Hammarstedt, A.; Smith, U. Insulin Resistance and Impaired Adipogenesis. *Trends in Endocrinology & Metabolism* 2015, 1-8.

(18) Tran, L.; Zielinski, a.; Roach, a. H.; Jende, J. a.; Householder, a. M.; Cole, E. E.; Atway, S. a.; Amornyard, M.; Accursi, M. L.; Shieh, S. W.; Thompson, E. E. The Pharmacologic Treatment of Type 2 Diabetes: Oral Medications. *Annals of Pharmacotherapy* 2015, No. 119.

(19) Stumvoll, M.; Nurjhan, N.; Perriello, G.; Dailey, G.; Gerich, J. E. Metabolic Effects of Metformin in Non-Insulin-Dependent Diabetes Mellitus. *The New England journal of medicine* 1995, 333, 550-554.

(20) Beck-Nielsen, H.; Hother-Nielsen, O.; Staehr, P. Is Hepatic Glucose Production Increased in Type 2 Diabetes Mellitus? *Curr Diab Rep* 2002, 2, 231-236.

(21) Morphy, R.; Rankovic, Z. Designed Multiple Ligands. An Emerging Drug Discovery Paradigm. *Journal of medicinal chemistry* 2005, 48 (21), 6523-6543.

(22) Lefebvre, P.; Shankaranarayanan, P.; Lera, A. R. De; Bourguet, W. Editorial Current Advances In Therapeutic Applications of Nuclear Receptors. *Current topics in medicinal chemistry* 2012, 12, 484-485.

(23) Tontonoz, P.; Spiegelman, B. M. Fat and beyond: The Diverse Biology of PPAR Gamma. *Annual review of biochemistry* 2008, 77, 289-312.

(24) Chaudhary, S.; Dube, A.; Kothari, V.; Sachan, N.; Upasani, C. D. NS-1: A Novel Partial Peroxisome Proliferator-Activated Receptor Gamma Agonist to Improve Insulin Sensitivity and Metabolic Profile. *European Journal of Pharmacology* 2012, 684, 154-160.

(25) Tontonoz, P.; Nagy, L.; Alvarez, J. G. a; Thomazy, V. a.; Evans, R. M. PPAR Gamma Promotes Monocyte/macrophage Differentiation and Uptake of Oxidized LDL. *Cell* 1998, 93, 241-252.

(26) Tontonoz, P.; Hu, E.; Devine, J.; Beale, E. G.; Spiegelman, B. M. PPAR Gamma 2 Regulates Adipose Expression of the Phosphoenolpyruvate Carboxykinase Gene. *Molecular and cellular biology* 1995, 15 (1), 351-357.

(27) Tontonoz, P.; Hu, E.; Graves, R. A.; Budavari, A. I.; Spiegelman, B. M. mPPARgamma2: Tissue-Specific Regulator of an Adipocyte Enhancer. *Genes & Development* 1994, 4, 1224-1234.

(28) Martin, G.; Schoonjans, K.; Lefebvre, a M.; Staels, B.; Auwerx, J. Coordinate Regulation of the Expression of the Fatty Acid Transport Protein and Acyl-CoA Synthetase Genes by PPARalpha and PPARgamma Activators. *The Journal of biological chemistry* 1997, 272 (45), 28210-28217.

(29) Schoonjans, K.; Peinado-Onsurbe, J.; Lefebvre, a M.; Heyman, R. a; Briggs, M.; Deeb, S.; Staels, B.; Auwerx, J. PPARalpha and PPARgamma Activators Direct a Distinct Tissue-Specific Transcriptional Response via a PPRE in the Lipoprotein Lipase Gene. *The EMBO* journal 1996, 15 (19), 5336-5348.

(30) Ken Kishida, Iichiro Shimomura, Hitoshi Nishizawa, Norikazu Maeda, Hiroshi Kuriyama, Hidehiko Kondo, Morihiro Matsuda, Hiroyuki Nagaretani, Noriyuki Ouchi, Kikuko Hotta, Shinji Kihara, Takashi Kadowak, Tohru Funahashi, and Y. M. PPARγ-Induced Transcriptinal Activation of AQPap. *The american society of Biochemistry and Molecular Biology* 2001.

(31) Yamauchi, T.; Kamon, J.; Waki, H.; Terauchi, Y.; Kubota, N.; Hara, K.; Mori, Y.; Ide, T.; Murakami, K.; Tsuboyama-Kasaoka, N.; Ezaki, O.; Akanuma, Y.; Gavrilova, O.; Vinson, C.; Reitman, M. L.; Kagechika, H.; Shudo, K.; Yoda, M.; Nakano, Y.; Tobe, K.; Nagai, R.; Kimura, S.; Tomita, M.; Froguel, P.; Kadowaki, T. The Fat-Derived Hormone Adiponectin Reverses Insulin Resistance Associated with Both Lipoatrophy and Obesity. *Nature medicine* 2001, 7, 941-946.

(32) Yamauchi, T.; Kamon, J.; Minokoshi, Y.; Ito, Y.; Waki, H.; Uchida, S.; Yamashita, S.; Noda, M.; Kita, S.; Ueki, K.; Eto, K.; Akanuma, Y.; Froguel, P.; Foufelle, F.; Ferre, P.; Carling, D.; Kimura, S.; Nagai, R.; Kahn, B. B.; Kadowaki, T. Adiponectin Stimulates Glucose Utilization and Fatty-Acid Oxidation by Activating AMP-Activated Protein Kinase. *Nature medicine* 2002, 8 (11), 1288-1295.

(33) Berg, A. H.; Combs, T. P.; Scherer, P. E. ACRP30/adiponectin: An Adipokine Regulating Glucose and Lipid Metabolism. *Trends in Endocrinology and Metabolism* 2002, 13 (2), 84-89.

(34) Hu, E.; Liang, P.; Spiegelman, B. M. AdipoQ Is a Novel Adipose-Specific Gene Dysregulated in Obesity. *Journal of Biological Chemistry* 1996, 271 (18), 10697-10703.

(35) Steppan, C. M.; Bailey, S. T.; Bhat, S.; Brown, E. J.; Banerjee, R. R.; Wright, C. M.; Patel, H. R.; Ahima, R. S.; Lazar, M. a. The Hormone Resistin Links Obesity to Diabetes. *Nature* 2001, 409, 307-312.

(36) Banerjee, R. R.; Rangwala, S. M.; Shapiro, J. S.; Rich, a S.; Rhoades, B.; Qi, Y.; Wang, J.; Rajala, M. W.; Pocai, A.; Scherer, P. E.; Steppan, C. M.; Ahima, R. S.; Obici, S.; Rossetti, L.; Lazar, M. a. Regulation of Fasted Blood Glucose by Resistin. *Science* (New York, N.Y.) 2004, 303 (1997), 1195-1198.

(37) Leiter, L. a. Beta-Cell Preservation: A Potential Role for Thiazolidinediones to Improve Clinical Care in Type 2 Diabetes. *Diabetic medicine: a journal of the British Diabetic Association* 2005, 22, 963-972.

(38) Anny H. Xiang, Ruth K. Peters, Sin L. Kjos, Aura Marroquin, Jose Goico, Cesar Ochoa, Miwa Kawakubo, and T. A. B. Effect of Pioglitazone on Pancreatic B-Cell Function and Diabetes Risk in Hispanic Women With Prior Gestational Diabetes. *Diabetes* 2006, 55 (2), 517-522.

(39) Kahn, S. E.; Lachin, J. M.; Zinman, B.; Haffner, S. M.; Aftring, R. P.; Paul, G.; Kravitz, B. G.; Herman, W. H.; Viberti, G.; Holman, R. R.; Jones, N.; O'Neill, C. Effects of Rosiglitazone, Glyburide, and Metformin on B-Cell Function and Insulin Sensitivity in ADOPT. *Diabetes* 2011, 60 (May), 1552-1560.

(40) Sripalakit, P.; Maphanta, S.; Neamhom, P.; Saraphanchotiwitthaya, A.; Polnok, S.; Yokubol, D. Comparative Study on the Bioequivalence of Two Formulations of Pioglitazone Tablet in Healthy Thai Male Volunteers. *Drug development and industrial pharmacy* 2007, 33, 1362-1368.

(41) GlaxoSmithKline. Avandia Tablets-Medication Guide. 2014, 1-42.

(42) STEPHEN ARONOFF, SID ROSENBLATT, SUSAN BRAITHWAITE, J. W. E. Pioglitazone Hydrochloride Monotherapy Improves Glycemic Control in the Treatment of Patients With Type 2 Diabetes. *Diabetes Care* 2000, 23 (11), 1605-1611.

(43) Lawrence S. Phillips, George Grunberger, Elizabeth Miller, R. P. Rosiglitazone Improves Glycemic Control in Patients With Type 2 Diabetes. *Diabetes Care* 2001, 24 (2), 308-315.

(44) Ahmadian, M.; Suh, J. M.; Hah, N.; Liddle, C.; Atkins, A. R.; Downes, M.; Evans, R. M. PPARγ Signaling and Metabolism: The Good, the Bad and the Future. *Nature Medicine* 2013, 99 (5), 557-566.

(45) Rohatgi, A.; McGuire, D. K. Effects of the Thiazolidinedione Medications on Micro- and Macrovascular Complications in Patients with Diabetes—Update 2008. *Cardiovascular Drugs and Therapy* 2008, 22, 233-240.

(46) Vivian Fonseca, Md. Julio Rosenstock, Md. Rita Patwardhan, PhD Alan Salzman, MD, P. Effect of Metformin and Rosiglitazone Combination Therapy in Patients With Type 2 Diabetes Mellitus. *JAMA* 2000, 283 (13), 1695-1703.

(47) Einhorn, D.; Rendell, M.; Rosenzweig, J.; Egaq, J. W.; Mathisen, A. L.; Schneider, R. L.; Study, P. Pioglitazone Hydrochloride in Combination with Metformin in the Treatment of Qpe 2 Diabetes Mellitus: A Randomized, Placebo-Controlled Study. *Clinical Therapeutics* 2000, 22 (12), 1395-1409.

(48) Lebovitz, H. E.; Dole, J. F.; Patwardhan, R.; Rappaport, E. B.; Freed, M. I. Rosiglitazone Monotherapy Is Effective in Patients with Type 2 Diabetes. *The Journal of clinical endocrinology and metabolism* 2001, 86 (1), 280-288.

(49) Taeye, B. M. De; Morisseau, C.; Coyle, J.; Covington, J. W.; Yang, J.; Murphy, S. B.; Friedman, D. B.; Hammock, B. B.; Vaughan, E. Expression and Regulation of Soluble Epoxide Hydrolase in Adipose Tissue. *Obesity* (Silver Spring) 2011, 18 (3), 489-498.

(50) Imig, J. D.; Hammock, B. D. Soluble Epoxide Hydrolase as a Therapeutic Target for Cardiovascular Diseases. *Nature reviews. Drug discovery* 2009, 8 (10), 794-805.

(51) Huang, A.; Sun, D.; Jacobson, A.; Carroll, M. a.; Falck, J. R.; Kaley, G. Epoxyeicosatrienoic Acids Are Released to Mediate Shear Stress-Dependent Hyperpolarization of Arteriolar Smooth Muscle. *Circulation Research* 2005, 96, 376-383.

(52) Archer, S. L.; Gragasin, F. S.; Wu, X.; Wang, S.; McMurtry, S.; Kim, D. H.; Platonov, M.; Koshal, A.; Hashimoto, K.; Campbell, W. B.; Falck, J. R.; Michelakis, E. D. Endothelium-Derived Hyperpolarizing Factor in Human Internal Mammary Artery Is 11,12-Epoxyeicosatrienoic Acid and Causes Relaxation by Activating Smooth Muscle BKCa Channels. *Circulation* 2003, 107, 769-776.

(53) Todd R. Harris, Ning Li, Nipavan Chiamvimonvat, and B. D.; Hammock. The Potential of Soluble Epoxide Hydrolase Inhibition in the Treatment of Cardiac Hypertrophy. *Congest Heart Fail.* 2008, 14 (4), 219-224.

(54) Shen, L.; Peng, H.; Peng, R.; Fan, Q.; Zhao, S.; Xu, D.; Morisseau, C.; Chiamvimonvat, N.; Hammock, B. D. Inhibition of Soluble Epoxide Hydrolase in Mice Promotes Reverse Cholesterol Transport and Regression of Atherosclerosis. *Atherosclerosis* 2015, 239, 557-565.

(55) Wagner, K.; Inceoglu, B.; Dong, H.; Yang, J.; Hwang, S. H.; Jones, P.; Morisseau, C.; Hammock, B. D. Comparative Efficacy of 3 Soluble Epoxide Hydrolase Inhibitors in Rat Neuropathic and Inflammatory Pain Models. *European Journal of Pharmacology* 2013, 700 (1-3), 93-101.

(56) Wagner, K.; Yang, J.; Inceoglu, B.; Hammock, B. D. Soluble Epoxide Hydrolase Inhibition Is Antinociceptive in a Mouse Model of Diabetic Neuropathy. *Journal of Pain* 2013, 1-8.

(57) Lee, K. S. S.; Liu, J.-Y.; Wagner, K. M.; Pakhomova, S.; Dong, H.; Morisseau, C.; Fu, S. H.; Yang, J.; Wang, P.; Ulu, A.; Mate, C. a; Nguyen, L. V; Hwang, S. H.; Edin, M. L.; Mara, A. a; Wulff, H.; Newcomer, M. E.; Zeldin, D. C.; Hammock, B. D. Optimized Inhibitors of Soluble Epoxide Hydrolase Improve in Vitro Target Residence Time and in Vivo Efficacy. *Journal of medicinal chemistry* 2014.

(58) Kim, J.; Yoon, S. P.; Toews, M. L.; Imig, J. D.; Hwang, S. H.; Hammock, B. D.; Padanilam, B. J. Pharmacological Inhibition of Soluble Epoxide Hydrolase Prevents Renal Interstitial Fibrogenesis in Obstructive Nephropathy. *AJP: Renal Physiology* 2014, 308 (35), F131-F139.

(59) Liu, Y.; Zhang, Y.; Schmelzer, K.; Lee, T.-S.; Fang, X.; Zhu, Y.; Spector, A. A.; Gill, S.; Morisseau, C.; Hammock, B. D.; Shyy, J. Y.-J. The Antiinflammatory Effect of Laminar Flow: The Role of PPARgamma, Epoxyeicosatrienoic Acids, and Soluble Epoxide Hydrolase. *Proceedings of the National Academy of Sciences of the U.S. Pat. No.* 2,005,102 (46), 16747-16752.

(60) Xu, D. Y.; Davis, B. B.; Wang, Z. H.; Zhao, S. P.; Wasti, B.; Liu, Z. L.; Li, N.; Morisseau, C.; Chiamvimonvat, N.; Hammock, B. D. A Potent Soluble Epoxide Hydrolase Inhibitor, T-AUCB, Acts through PPARγ to Modulate the Function of Endothelial Progenitor Cells from Patients with Acute Myocardial Infarction. *International Journal of Cardiology* 2013, 167 (4), 1298-1304.

(61) Hammock, Bruce D. Ahmet Bora Inceoglu, S. L. J. Alleviating Neurophatic Pain with EETs and sEH Inhibition (Patent), 2010.

(62) Lee, K. S. S.; Liu, J.-Y.; Wagner, K. M.; Pakhomova, S.; Dong, H.; Morisseau, C.; Fu, S. H.; Yang, J.; Wang, P.; Ulu, A.; Mate, C. a; Nguyen, L. V; Hwang, S. H.; Edin, M. L.; Mara, A. a; Wulff, H.; Newcomer, M. E.; Zeldin, D. C.; Hammock, B. D. Optimized Inhibitors of Soluble Epoxide Hydrolase Improve in Vitro Target Residence Time and in Vivo Efficacy. *Journal of medicinal chemistry* 2014, 57, 7016-7030.

(63) Luo, P.; Chang, H.-H.; Zhou, Y.; Zhang, S.; Hwang, S. H.; Morisseau, C.; Wang, C.-Y.; Inscho, E. W.; Hammock, B. D.; Wang, M.-H. Inhibition or Deletion of Soluble Epoxide Hydrolase Prevents Hyperglycemia, Promotes Insulin Secretion, and Reduces Islet Apoptosis. *The Journal of pharmacology and experimental therapeutics* 2010, 334 (2), 430-438.

(64) Imig, J. D. Epoxides and Soluble Epoxide Hydrolase in Cardiovascular Physiology. *Physiological Reviews* 2012, 92, 101-130.

(65) Capdevila, J. H.; Falck, J. R.; Imig, J. D. Roles of the Cytochrome P450 Arachidonic Acid Monooxygenases in the Control of Systemic Blood Pressure and Experimental Hypertension. *Kidney international* 2007, 72, 683-689.

(66) Imig, J. D.; Walsh, K. a; Hye Khan, M. A.; Nagasawa, T.; Cherian-Shaw, M.;

Shaw, S. M.; Hammock, B. D. Soluble Epoxide Hydrolase Inhibition and Peroxisome Proliferator Activated Receptor F Agonist Improve Vascular Function and Decrease Renal Injury in Hypertensive Obese Rats. *Experimental biology and medicine* (Maywood, N.J.) 2012, 237, 1402-1412.

(67) La Buscato, E.; Blocher, R.; Lamers, C.; Klingler, F.-M.; Hahn, S.; Steinhilber, D.; Schubert-Zsilavecz, M.; Proschak, E. Design and Synthesis of Dual Modulators of Soluble Epoxide Hydrolase and Peroxisome Proliferator-Activated Receptors. *Journal of medicinal chemistry* 2012, 55 (23), 10771-10775.

(68) Sime, M.; Allan, A. C.; Chapman, P.; Fieldhouse, C.; Giblin, G. M. P.; Healy, M. P.; Lambert, M. H.; Leesnitzer, L. M.; Lewis, A.; Merrihew, R. V.; Rutter, R. a.; Sasse, R.; Shearer, B. G.; Wilson, T. M.; Xu, R. X.; Virley, D. J. Discovery of GSK1997132B a Novel Centrally Penetrant Benzimidazole PPARγ Partial Agonist. *Bioorganic and Medicinal Chemistry Letters* 2011, 21 (18), 5568-5572.

(69) Thalji, R. K.; McAtee, J. J.; Belyanskaya, S.; Brandt, M.; Brown, G. D.; Costell, M. H.; Ding, Y.; Dodson, J. W.; Eisennagel, S. H.; Fries, R. E.; Gross, J. W.; Harpel, M. R.; Holt, D. a.; Israel, D. I.; Jolivette, L. J.; Krosky, D.; Li, H.; Lu, Q.; Mandichak, T.; Roethke, T.; Schnackenberg, C. G.; Schwartz, B.; Shewchuk, L. M.; Xie, W.; Behm, D. J.; Douglas, S. a.; Shaw, A. L.; Marino, J. P. Discovery of 1-(1,3,5-Triazin-2-Y1)piperidine-4-Carboxamides as Inhibitors of Soluble Epoxide Hydrolase. *Bioorganic and Medicinal Chemistry Letters* 2013, 23, 3584-3588.

(70) Nomura, M.; Tanase, T.; Ide, T.; Tsunoda, M.; Suzuki, M.; Uchiki, H.; Murakami, K.; Miyachi, H. Design, Synthesis, and Evaluation of Substituted Phenylpropanoic Acid Derivatives as Human Peroxisome Proliferator Activated Receptor Activators. Discovery of Potent and Human Peroxisome Proliferator Activated Receptor Alpha Subtype-Selective Activators. *Journal of medicinal chemistry* 2003, 46 (Chart 1), 3581-3599.

(71) Schmitt, M. L.; Hauser, A. T.; Carlino, L.; Pippel, M.; Schulz-Fincke, J.; Metzger, E.; Willmann, D.; Yiu, T.; Barton, M.; Schille, R.; Sippl, W.; Jung, M. Nonpeptidic Propargylamines as Inhibitors of Lysine Specific Demethylase 1 (LSD1) with Cellular Activity. *Journal of Medicinal Chemistry* 2013, 56, 7334-7342.

(72) Valeur, E.; Bradley, M. PS-IIDQ: An Efficient Polymer-Supported Amide Coupling Reagent. *Chemical communications* (Cambridge, England) 2005, No. Table 1, 1164-1166.

(73) La Ferla, B.; Orsato, A.; Zona, C.; Cervi, G.; Papeo, G.; Felder, E. R.; Nicotra, F. Synthesis of a Beta-Carboline Scaffold Properly Functionalized for the Generation of Libraries of Bioactive Compounds. *Synthesis* 2010, 601-604.

(74) Hieke, M.; Ness, J.; Steri, R.; Greiner, C.; Werz, O.; Schubert-Zsilavecz, M.; Weggen, S.; Zettl, H. SAR Studies of Acidic Dual Gamma-secretase/PPARgamma Modulators. *Bioorganic and Medicinal Chemistry* 2011, 19 (18), 5372-5382.

(75) Proschak, E.; Sander, K.; Zettl, H.; Tanrikulu, Y.; Rau, O.; Schneider, P.; Schubert-Zsilavecz, M.; Stark, H.; Schneider, G. From Molecular Shape to Potent Bioactive Agents II: Fragment-Based de Novo Design. *ChemMedChem* 2009, 4 (1), 45-48.

(76) Giannetti, A. M.; Zheng, X.; Skelton, N. J.; Wang, W.; Bravo, B. J.; Bair, K. W.; Baumeister, T.; Cheng, E.; Crocker, L.; Feng, Y.; Gunzner-toste, J.; Ho, Y.; Hua, R.; Liederer, B. M.; Liu, Y.; Ma, X.; Brien, T. O.; Oeh, J.; Sampath, D.; Shen, Y.; Wang, C.; Wang, L.; Wu, H.; Xiao, Y.; Yuen, P.; Zak, M.; Zhao, G.; Zhao, Q.; Dragovich, P. S. Fragment-Based Identi Fi Cation of Amides Derived from Trans-2-(Pyridin-3-Y1)cyclopropanecarboxylic Acid as Potent Inhibitors of Human Nicotinamide Phosphoribosyltransferase (NAMPT). *Journal of medicinal chemistry* 2014.

(77) Toy, P. H.; Dhanabalasingam, B.; Newcomb, M.; Hanna, I. H.; Hollenberg, P. F. A Substituted Hypersensitive Radical Probe for Enzyme-Catalyzed Hydroxylations: Synthesis of Racemic and Enantiomerically Enriched Forms and Application in a Cytochrome P450-Catalyzed Oxidation. *J. Org. Chem.* 1997, 62 (11), 9114-9122.

(78) Reichelt, A.; Gaul, C.; Frey, R. R.; Kennedy, A.; Martin, S. F. Design, Synthesis, and Evaluation of Matrix Metalloprotease Inhibitors Bearing Cyclopropane-Derived Peptidomimetics as P1' and P2' Replacements. *Journal of Organic Chemistry* 2002, 67 (c), 4062-4075.

(79) Johnson, S. M.; Petrassi, H. M.; Palaninathan, S. K.; Mohamedmohaideen, N. N.; Purkey, H. E.; Nichols, C.; Chiang, K. P.; Walkup, T.; Sacchettini, J. C.; Sharpless, K. B.; Kelly, J. W. Bisaryloxime Ethers as Potent Inhibitors of Transthyretin Amyloid Fibril Formation. *Journal of Medicinal Chemistry* 2005, 48, 1576-1587.

(80) Henderson, T. J.; Cullinan, D. B. Purity Analysis of Hydrogen Cyanide, Cyanogen Chloride and Phosgene by Quantitative (13)C NMR Spectroscopy. *Magnetic resonance in chemistry: MRC* 2007, 45 (March), 954-961.

(81) Miyaura, N.; Suzuki, A. Palladium-Catalyzed Cross-Coupling Reactions of Organoboron Compounds. *Chemical Reviews* 1995, 95 (1), 2457-2483.

(82) Morini, G.; Comini, M.; Rivara, M.; Rivara, S.; Bordi, F.; Plazzi, P. V.; Flammini, L.; Saccani, F.; Bertoni, S.; Ballabeni, V.; Barocelli, E.; Mor, M. Synthesis and Structure-Activity Relationships for Biphenyl H3 Receptor Antagonists with Moderate Anti-Cholinesterase Activity. *Bioorganic and Medicinal Chemistry* 2008, 16 (23), 9911-9924.

(83) Zhao, H. The Synthesis and Structures of Deuterium-Labeled 5-Substituted 1H-Tetrazoles. *Journal of Labelled Compounds and Radiopharmaceuticals* 2008, 51 (December 2007), 293-296.

(84) Pillarisetti, S.; Khanna, I. Targeting Soluble Epoxide Hydrolase for Inflammation and Pain—an Overview of Pharmacology and the Inhibitors. *Inflammation & allergy drug targets* 2012, 11 (2), 143-158.

(85) Xing, L.; McDonald, J. J.; Kolodziej, S. a; Kurumbail, R. G.; Williams, J. M.; Warren, C. J.; O'Neal, J. M.; Skepner, J. E.; Roberds, S. L. Discovery of Potent Inhibitors of Soluble Epoxide Hydrolase by Combinatorial Library Design and Structure-Based Virtual Screening. *Journal of medicinal chemistry* 2011, 54 (5), 1211-1222.

(86) Lamers, C.; Schubert-Zsilavecz, M.; Merk, D. Therapeutic Modulators of Peroxisome Proliferator-Activated Receptors (PPAR): A Patent Review (2008-Present). *Expert opinion on therapeutic patents* 2012, 22 (7), 803-841.

(87) Ohashi, M.; Nakagome, I.; Kasuga, J. I.; Nobusada, H.; Matsuno, K.; Makishima, M.; Hirono, S.; Hashimoto, Y.; Miyachi, H. Design, Synthesis and in Vitro Evaluation of a Series of Alpha-Substituted Phenylpropanoic Acid PPARgamma Agonists to Further Investigate the Stereochemistry-Activity Relationship. *Bioorganic and Medicinal Chemistry* 2012, 20 (21), 6375-6383.

(88) Gomez, G. A.; Morisseau, C.; Hammock, B. D.; Christianson, D. W. Human Soluble Epoxide Hydrolase: Structural Basis of Inhibition by 4-(3-Cyclohexylureido)-Carboxylic Acids. *Protein science: a publication of the Protein Society* 2006, 15 (1), 58-64.

(89) Pirat, C.; Farce, A.; Lebegue, N.; Renault, N.; Furman, C.; Millet, R.; Yous, S.; Speca, S.; Berthelot, P.; Desreumaux, P.; Chavatte, P. Targeting Peroxisome Proliferator-Activated Receptors (PPARs): Development of Modulators. *Journal of Medicinal Chemistry* 2012, 55, 4027-4061.

(90) Hahn, S.; Achenbach, J.; Buscato, E.; Klingler, F.-M.; Schroeder, M.; Meirer, K.; Hieke, M.; Heering, J.; Barbosa-Sicard, E.; Loehr, F.; Fleming, I.; Doetsch, V.; Schubert-Zsilavecz, M.; Steinhilber, D.; Proschak, E. Complementary Screening Techniques Yielded Fragments That Inhibit the Phosphatase Activity of Soluble Epoxide Hydrolase. *ChemMedChem* 2011, 6 (12), 2146-2149.

(91) Thieme, T. M.; Steri, R.; Proschak, E.; Paulke, A.; Schneider, G.; Schubert-Zsilavecz, M. Rational Design of a Pirinixic Acid Derivative That Acts as Subtype-Selective PPARgamma Modulator. *Bioorganic and Medicinal Chemistry Letters* 2010, 20 (8), 2469-2473.

(92) Ishiyama, M.; Tominaga, H.; Shiga, M.; Sasamoto, K.; Ohkura, Y.; Ueno, K. A Combined Assay of Cell Viability and in Vitro Cytotoxicity with a Highly Water-Soluble Tetrazolium Salt, Neutral Red and Crystal Violet. *Biological & pharmaceutical bulletin* 1996, 19, 1518-1520.

(93) Morisseau, C.; Goodrow, M. H.; Newman, J. W.; Wheelock, C. E.; Dowdy, D. L.;
Hammock, B. D. Structural Refinement of Inhibitors of Urea-Based Soluble Epoxide Hydrolases. *Biochemical pharmacology* 2002, 63 (9), 1599-1608.

(94) Morin, C.; Sirois, M.; Échavé, V.; Albadine, R.; Rousseau, E. 17,18-Epoxyeicosatetraenoic Acid Targets PPARγ and p38 Mitogen-Activated Protein Kinase to Mediate Its Anti-Inflammatory Effects in the Lung Role of Soluble Epoxide Hydrolase. *American Journal of Respiratory Cell and Molecular Biology* 2010, 43 (21), 564-575.

(95) Guan, Y. Peroxisome Proliferator-Activated Receptors (PPARs): Novel Therapeutic Targets in Renal Disease. *Kidney international* 2001, 61, 354-355.

(96) Choi, J. H.; Banks, A. S.; Estall, J. L.; Kajimura, S.; Bostrom, P.; Laznik, D.; Ruas, J. L.; Chalmers, M. J.; Kamenecka, T. M.; Blither, M.; Griffin, P. R.; Spiegelman, B. M. Anti-Diabetic Drugs Inhibit Obesity-Linked Phosphorylation of PPARgamma by Cdk5. *Nature* 2010, 466 (July), 451-456.

(97) Choi, J. H.; Banks, A. S.; Kamenecka, T. M.; Busby, S. a.; Chalmers, M. J.; Kumar, N.; Kuruvilla, D. S.; Shin, Y.; He, Y.; Bruning, J. B.; Marciano, D. P.; Cameron, M. D.; Laznik, D.; Jurczak, M. J.; Schilrer, S. C.; Vidović, D.; Shulman, G. I.; Spiegelman, B. M.; Griffin, P. R. Antidiabetic Actions of a Non-Agonist PPARγ Ligand Blocking Cdk5-Mediated Phosphorylation. *Nature* 2011, 477, 477-481.

(98) Min Lu, David A. Sarruf, Saswata Talukdar, Shweta Sharma, Pingping Li, Gautam Bandyopadhyay, Sarah Nalbandian, WuQiang Fan, Jiaur R. Gayen, S. K.; Mahata, Nicholas J. Webster, Michael W. Schwartz2,4, and J. M. O. Brain PPARγ Promotes Obesity and Is Required for the Insulin—Sensitizing Effect of Thiazolidinediones. *Nat Med.* 2012, 127 (5), 358-366.

(99) Karen K. Ryan, Bailing Li, Bernadette E. Grayson, Emily K. Matter, Stephen C. Woods, and R. J. S. A Role for CNS PPAR F in the Regulation of Energy Balance. *Nat Med.* 2011, 17 (5), 623-626.

(100) Higgins, L. S.; Depaoli, A. M. Selective Peroxisome Proliferator-Activated Receptor G (PPAR Gamma) Modulation as a Strategy for Safer Therapeutic PPAR G Activation 1-3. *The American journal of clinical nutrition* 2010, 91, 267-272.

(101) Sun, Y.; Zhang, X.; Lu, T.; Yuan, Y.; Ding, Q.; Lu, C. A Study on the PK and BA Profiles in the Mouse Body for Leonurine O/O Microemulsion with Determination by the LC-MS/MS Method. European Journal of Drug Metabolism and Pharmacokinetics 2015.

(102) Hwang, S. H.; Wecksler, A. T.; Zhang, G.; Morisseau, C.; Nguyen, L. V.; Fu, S. H.; Hammock, B. D. Synthesis and Biological Evaluation of Sorafenib- and Regorafenib-like sEH Inhibitors. *Bioorganic and Medicinal Chemistry Letters* 2013, 23 (13), 3732-3737.

(103) Hwang, S. H.; Wagner, K. M.; Morisseau, C.; Liu, J.-Y.; Dong, H.; Wecksler, A. T.; Hammock, B. D. Synthesis and Structure-Activity Relationship Studies of Urea-Containing Pyrazoles as Dual Inhibitors of Cyclooxygenase-2 and Soluble Epoxide Hydrolase. *Journal of medicinal chemistry* 2011, 54 (8), 3037-3050.

(104) Jones, P. D.; Tsai, H.-J.; Do, Z. N.; Morisseau, C.; Hammock, B. D. Synthesis and SAR of Conformationally Restricted Inhibitors of Soluble Epoxide Hydrolase. *Bioorganic & medicinal chemistry letters* 2006, 16, 5212-5216.

(105) Li, H. Y.; Jin, Y.; Morisseau, C.; Hammock, B. D.; Long, Y. Q. The 5-Substituted Piperazine as a Novel Secondary Pharmacophore Greatly Improving the Physical Properties of Urea-Based Inhibitors of Soluble Epoxide Hydrolase. *Bioorganic and Medicinal Chemistry* 2006, 14, 6586-6592.

(106) Huang, S. X.; Li, H. Y.; Liu, J. Y.; Morisseau, C.; Hammock, B. D.; Long, Y. Q. Incorporation of Piperazino Functionality into 1,3-Disubstituted Urea as the Tertiary Pharmacophore Affording Potent Inhibitors of Soluble Epoxide Hydrolase with Improved Pharmacokinetic Properties. *Journal of Medicinal Chemistry* 2010, 53 (FIG. 1), 8376-8386.

(107) Miyachi, H.; Nomura, M.; Tanase, T.; Suzuki, M.; Murakami, K.; Awano, K. Enantio-Dependent Binding and Transactivation of Optically Active Phenylpropanoic Acid Derivatives at Human Peroxisome Proliferator-Activated Receptor Alpha. *Bioorganic and Medicinal Chemistry Letters* 2002, 12, 333-335.

(108) Miyachi, H.; Nomura, M.; Tanase, T.; Takahashi, Y.; Ide, T.; Tsunoda, M.; Murakami, K.; Awano, K. Design, Synthesis and Evaluation of Substituted Phenylpropanoic Acid Derivatives as Peroxisome Proliferator-Activated Receptor (PPAR) Activators: Novel Human PPARalpha-Selective Activators. *Bioorganic & medicinal chemistry letters* 2002, 12, 77-80.
(109) Tang, W. H. W.; Maroo, A. PPARgamma Agonists: Safety Issues in Heart Failure. *Diabetes, obesity & metabolism* 2007, 9, 447-454.
(110) Yang, T.; Soodvilai, S. Renal and Vascular Mechanisms of Thiazolidinedione-Induced Fluid Retention. *PPAR research* 2008, 2008.
(111) Hwang, S. H.; Wecksler, a. T.; Wagner, K.; Hammock, B. D. Rationally Designed Multitarget Agents against Inflammation and Pain. *Current medicinal chemistry* 2013, 20, 1783-1799.
(112) Wolf, N. M.; Morisseau, C.; Jones, P. D.; Hock, B.; Hammock, B. D. Development of a High-Throughput Screen for Soluble Epoxide Hydrolase Inhibition. *Analytical biochemistry* 2006, 355 (1), 71-80.
(113) Rau, O.; Wurglics, M.; Paulke, A.; Zitzkowski, J.; Meindl, N.; Bock, A.; Dingermann, T.; Abdel-Tawab, M.; Schubert-Zsilavecz, M. Carnosic Acid and Carnosol, Phenolic Diterpene Compounds of the Labiate Herbs Rosemary and Sage, Are Activators of the Human Peroxisome Proliferator-Activated Receptor Gamma. *Planta medica* 2006, 72 (10), 881-887.
(114) Zebisch, K.; Voigt, V.; Wabitsch, M.; Brandsch, M. Protocol for Effective Differentiation of 3 T3-L1 Cells to Adipocytes. *Analytical Biochemistry* 2012, 425 (1), 88-90.
(115) Sisignano, M.; Park, C.-K.; Angioni, C.; Zhang, D. D.; von Hehn, C.; Cobos, E. J.; Ghasemlou, N.; Xu, Z.-Z.; Kumaran, V.; Lu, R.; Grant, A.; Fischer, M. J. M.; Schmidtko, A.; Reeh, P.; Ji, R.-R.; Woolf, C. J.; Geisslinger, G.; Scholich, K.; Brenneis, C. 5,6-EET Is Released upon Neuronal Activity and Induces Mechanical Pain Hypersensitivity via TRPA1 on Central Afferent Terminals. *The Journal of neuroscience: the official journal of the Society for Neuroscience* 2012, 32 (18), 6364-6372.

What is claimed is:

1. A compound having the structure:

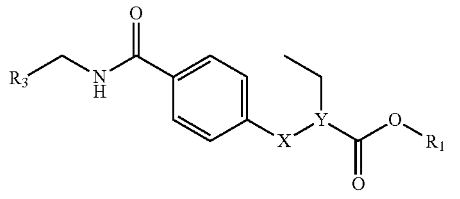

wherein: X—Y is CH═C or $CH_2$—CH; $R_1$ is $CH_2CH_3$, $CH_3$ or H; and $R_3$ is a fluoro-substituted aryl group; or a salt thereof wherein the compound is able to simultaneously inhibit soluble epoxide hydrolase (sEH) and selectively exhibit agonist activity toward peroxisome proliferator-activated receptor gamma (PPARγ) as compared to both peroxisome proliferator-activated receptor alpha (PPARα) and peroxisome proliferator-activated receptor alpha (PPARδ) to treat metabolic syndrome in a subject.

2. The compound according to claim 1, wherein the fluoro-substituted aryl group at $R_3$ is a trifluoromethyl- or trifluoromethoxy substituted phenyl group.

3. The compound according to claim 2, wherein the trifluoromethyl- or trifluoromethoxy-substitution is at said phenyl group's ortho position.

4. The compound according to claim 1, wherein $R_3$ is:

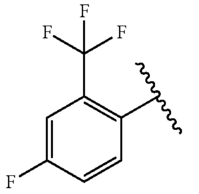

or

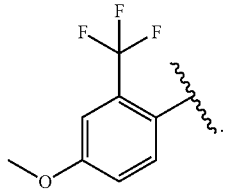

5. The compound of claim 1, wherein $R_3$ is:

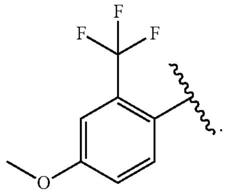

6. The compound according to claim 1, wherein X—Y is $CH_2$—CH and $R_1$ is $CH_2CH_3$.

7. A compound having the structure:

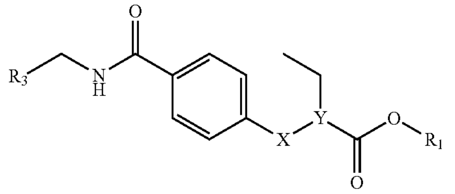

wherein: X—Y is CH═C; $R_1$ is $CH_2CH_3$; and $R_3$ is a fluoro-substituted aryl group; or a salt thereof.

8. The compound according to claim 1, wherein X—Y is $CH_2$—CH and $R_1$ is H.

9. A compound having the structure:

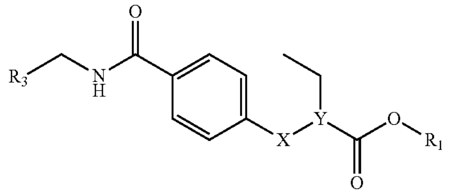

wherein: X—Y is $CH_2$—CH; $R_1$ is H; and $R_3$ is a fluoro-substituted aryl group; or a salt thereof.

10. The compound according to claim 1, wherein the compound exhibits a half maximal inhibitory concentration ($IC_{50}$) for soluble epoxide hydrolase (sEH) and a half maximal effective concentration ($EC_{50}$) for peroxisome proliferator-activated receptor gamma (PPARγ) that are less than 1.0 micromolar when administered to a subject, wherein said compound further exhibits half maximal effective concentrations ($EC_{50}$s) for both peroxisome proliferator-activated receptor gamma (PPAPα) and peroxisome proliferator-activated receptor gamma (PPARδ) greater than 10 micromolar.

11. A composition comprising: (a) a compound according to claim 1; and (b) a pharmaceutically acceptable carrier.

12. The composition of claim 11 formulated as an oral dosage.

13. A method of treating metabolic syndrome in a subject, comprising administering to a subject a therapeutically effective amount of a compound according to claim 1, wherein soluble epoxide hydrolase (sEH) and peroxisome proliferator-activated receptor gamma (PPARγ) are simultaneously-modulated by the compound thereby treating metabolic syndrome in said subject.

14. The method of claim 13, wherein said therapeutically effective amount provides a half maximal inhibitory concentration ($IC_{50}$) for sEH and a half maximal effective concentration ($EC_{50}$) for PPARγ that are less than 1.0 micromolar in the subject.

15. A method of treating diabetes in a subject, comprising administering to a subject a therapeutically effective amount of a compound according to claim 1, wherein soluble epoxide hydrolase (sEH) and peroxisome proliferator-activated receptor gamma (PPARγ) are simultaneously-modulated by the compound thereby treating diabetes in said subject.

16. The method of claim 15, wherein said therapeutically effective amount provides a half maximal inhibitory concentration ($IC_{50}$) for sEH and a half maximal effective concentration ($EC_{50}$) for PPARγ that are less than 1.0 micromolar in the subject.

17. A method of simultaneously-modulating soluble epoxide hydrolase (sEH) and peroxisome proliferator-activated receptor gamma (PPARγ) activities in a subject, comprising administering to a subject a therapeutically effective amount of a compound according to claim 1, wherein sEH and peroxisome proliferator-activated receptor gamma PPARγ activities are simultaneously-modulated by the compound in the subject.

18. The method of claim 17, wherein said therapeutically effective amount provides a half maximal inhibitory concentration ($IC_{50}$) for sEH and a half maximal effective concentration ($EC_{50}$) for PPARγ that are less than 1.0 micromolar in the subject.

19. The method of claim 13, wherein X—Y is $CH_2CH$, $R_1$ is H, and $R_3$ is

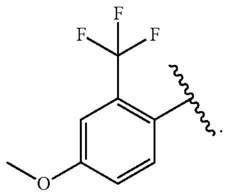

20. The method of claim 15, wherein X—Y is $CH_2CH$, $R_1$ is H, and $R_3$ is

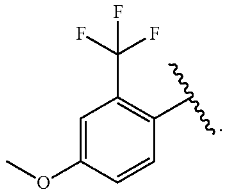 [SMILES: *c1ccc(OC)cc1C(F)(F)F]

21. The method of claim 17, wherein X—Y is $CH_2CH$, $R_1$ is H, and $R_3$ is

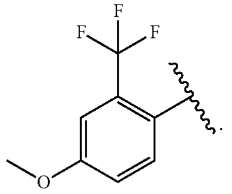

22. The compound of claim 1, wherein X—Y is $CH_2CH$, $R_1$ is H, and $R_3$ is

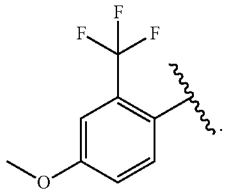 [SMILES: *c1ccc(OC)cc1C(F)(F)F]

* * * * *

UNITED STATES PATENT AND TRADEMARK OFFICE

CERTIFICATE OF CORRECTION

PATENT NO. : 10,927,069 B2
APPLICATION NO. : 15/737970
DATED : February 23, 2021
INVENTOR(S) : Imig It is certified that error appears in the above-identified patent and that said Letters Patent is hereby corrected as shown below:

In the Claims

| | |
|---|---|
| Claim 1<br>Column 79, Line 63 | Delete “alpha” and substitute therefore<br>-- delta --; |
| Claim 10<br>Column 81, Line 1 | Delete “gamma” and substitute therefore<br>-- alpha --; |
| Claim 10<br>Column 81, Line 2 | Delete “gamma” and substitute therefore<br>-- delta --. |

Signed and Sealed this
Thirtieth Day of August, 2022

Katherine Kelly Vidal

Katherine Kelly Vidal
*Director of the United States Patent and Trademark Office*